United States Patent
Kanojia et al.

(10) Patent No.: US 6,809,107 B1
(45) Date of Patent: Oct. 26, 2004

(54) NEUROTROPHIC PYRROLIDINES AND PIPERIDINES, AND RELATED COMPOSITIONS AND METHODS

(75) Inventors: Ramesh M. Kanojia, Bridgewater, NJ (US); Alfonzo D. Jordan, North Wales, PA (US); Allen B. Reitz, Lansdale, PA (US); Mark J. Macielag, Branchburg, NJ (US); Boyu Zhao, Lansdale, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/593,852

(22) Filed: Jun. 14, 2000

Related U.S. Application Data

(60) Provisional application No. 60/143,006, filed on Jul. 9, 1999.

(51) Int. Cl.[7] .................. A61K 31/47; C07D 277/04; C07D 275/02; C07D 261/02; C07D 261/10
(52) U.S. Cl. .................. 514/312; 514/314; 548/188; 548/213; 548/238; 548/240; 548/243; 546/153; 546/165
(58) Field of Search .................. 546/271 H, 94, 546/153, 165; 514/340, 312, 314; 548/188, 213, 238, 240, 243

(56) References Cited

U.S. PATENT DOCUMENTS

| | | |
|---|---|---|
| 5,294,603 A | 3/1994 | Rinehart .................. 514/10 |
| 5,461,146 A | 10/1995 | Lewis et al. |
| 5,614,547 A | 3/1997 | Hamilton et al. |
| 5,621,101 A | 4/1997 | Lewis et al. |
| 5,696,135 A | 12/1997 | Steiner et al. |
| 5,721,256 A | 2/1998 | Hamilton et al. |
| 5,756,494 A | 5/1998 | Lewis et al. |
| 5,795,908 A | 8/1998 | Hamilton et al. |

(List continued on next page.)

OTHER PUBLICATIONS

Martinez–Diaz et. al., "Preparation and enantiomeric purity determination of new chiral C2 building blocks based on the 4–amino–1,2,4–amino–1,2,4–triazole unit", Tetrahedron: Assymetry, 1994, 5(7), 1291–6.*

(List continued on next page.)

*Primary Examiner*—Johann Richter
*Assistant Examiner*—Binta Robinson

(57) ABSTRACT

This invention provides compounds having the following general structures:

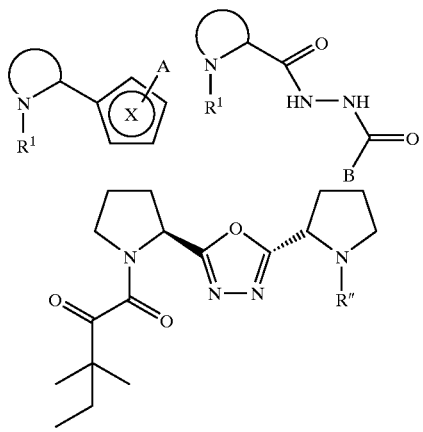

This invention also provides pharmaceutical compositions comprising same and methods of using these compositions to treat and prevent disorders characterized by neuronal damage.

13 Claims, 1 Drawing Sheet

U.S. PATENT DOCUMENTS

| | | |
|---|---|---|
| 5,798,355 A | 8/1998 | Steiner et al. |
| 5,801,187 A | 9/1998 | Li et al. |
| 5,801,197 A | 9/1998 | Steiner et al. |

FOREIGN PATENT DOCUMENTS

| | | | |
|---|---|---|---|
| DE | | 3721534 | * 2/1988 |
| WO | WO 92/19593 | | 11/1992 |
| WO | WO 94/02488 | | 2/1994 |
| WO | WO94/02488 | | 2/1994 |
| WO | WO 94/07858 | | 4/1994 |
| WO | WO94/07858 | | 4/1994 |
| WO | WO 96/06097 | | 2/1996 |
| WO | WO96/06097 | | 2/1996 |
| WO | WO 96/13506 | | 5/1996 |
| WO | WO96/13506 | | 5/1996 |
| WO | WO96/40140 | | 12/1996 |
| WO | WO 96/40140 | | 12/1996 |
| WO | WO 96/40633 | | 12/1996 |
| WO | WO96/40633 | | 12/1996 |
| WO | WO97/16190 | | 5/1997 |
| WO | WO 97/16190 | | 5/1997 |
| WO | WO97/31899 | | 9/1997 |
| WO | WO 97/31899 | | 9/1997 |
| WO | WO 98/13343 | | 4/1998 |
| WO | WO98/13343 | | 4/1998 |
| WO | WO 98/13355 | | 4/1998 |
| WO | WO98/13355 | | 4/1998 |
| WO | WO 98/20893 | | 5/1998 |
| WO | WO 98/25950 | | 6/1998 |
| WO | WO98/25950 | | 6/1998 |
| WO | WO 98/29116 | | 7/1998 |
| WO | WO98/29116 | | 7/1998 |
| WO | WO 98/29117 | | 7/1998 |
| WO | WO98/29117 | | 7/1998 |
| WO | WO 98/35675 | | 8/1998 |
| WO | WO 98/37882 | | 9/1998 |
| WO | WO98/37882 | | 9/1998 |
| WO | WO98/37885 | | 9/1998 |
| WO | WO 98/37885 | | 9/1998 |
| WO | WO 99/14998 | | 4/1999 |
| WO | WO99/45006 | | 9/1999 |
| WO | WO 99/45006 | | 9/1999 |
| WO | WO 99/62879 | | 12/1999 |
| WO | WO 99/62881 | | 12/1999 |
| WO | WO 99/62888 | | 12/1999 |
| WO | WO 00/32588 | | 6/2000 |
| WO | WO 00/46222 | | 8/2000 |
| ZA | | 964852 | 6/1996 |

OTHER PUBLICATIONS

Lancelot, et. al., "Pyrrolo[1,2–d][1,2,4]triazines. I. Pyrrole derivatives", J. Heterocycl. Chem. (1980), 17(4), 625–9.*

CA Reference 122:10548m "Preparation and enantiomeric purity determination of new chiral C2 building blocks based on the 4–amino–1,2–4–triazole unit", Martinez'–Diaz, et. al., p. 1174, vol. 122, 1995.*

Borg, et al.: "Synthesis of 1,2,4–Oxadiazole–, 1,3,4–Oxadiazole–, and 1,2,4–Triazole–Derived Dipeptidomimetics" J. Org. Chem. 1995, vol. 60, pp. 3112–3120.

Liang, G. et al: "An Improved Oxadiazole Synthesis Using Peptide Coupling Reagents" Tetrahedron Letters, vol. 37, pp. 6627–6630, 1996.

Juliano, L. et al: "Amino Acids and Peptides.XVI. Synthesis of Ng–Tosylarginyl Peptide Derivatives–Observation of Lactam Formation of Arginyl Residue" Chem. Pharm. Bull. 35 No. 6 pp. 2250–2553.

Hamilton, et al.: "Neuroimmunophilin Ligands as Novel Therapeutics for the Treatment of Degenerative Disorders of the Nervous System" Current Pharm. Design, Vo.3 No. 4, 1997, pp. 405–428.

Holt, D. A. et al.: "Structure–Activity Studies of Synthetic FKBP Ligands as Peptidyl–Prolyl Isomerase Inhabitors", Bioorganic & Medicinal Chemistry Letters, GB, Oxford, vol. 4, No. 2, 1994, pp. 315–320.

G. S. Hamilton et al. "FKBP12–Binding Domain Analogues of FK506 are Potent, Nonimmunosuppressive Neurotrophic Agents in vitro and and Promote Recovery in a Mouse Model of Parkinson's Disease" Bioorganic & Medicinal Chemistry Letters, GB, Oxford, vol. 7, No. 13, 1997, pp. 1785–1790.

Snyder, S. H. et al.: "Neural Action of Immunophilin Ligands" Trends in Pharmacological Sciences, vol. 19, No. 1, 1998, pp. 21–26.

International Search Report Application No. PCT/US00/16221 dated Mar. 28, 2001.

Roberta Brinton et al. "Advances and Challenges in the Prevention . . . " Pharm. Res. 1998, 15, 386–398.

Rajesh Pahwa et al. "Advances in the Treatment of Parkinson's Disease", Drugs Tody, 1998, 34, 95–105.

Erik Louvel et al., "Therapeutic Advances in Amyotrohic . . . " Trends Pharmacol. Sci 1997, 18, 196–203.

Geert–Jan Biessels et al., "Diabetic Neuropathy: Pathogenesis and Current . . . "Neurosci. Res. Commun., 1997, 20, 1–10.

D.R. Tomlinson et al., "Role of Neurotrophins in Diabetic Neuropathy . . . ", Diabetes, 1997, 46(Suppl. 2) S43–S–49.

Brinton, R.D. and Yamazaki, R.S., *Pharm. Res.*, 1998, 15, 386–398.

Pahwa, R. and Koller, W.C., *Drugs Today*, 1998, 34, 95–105.

Louvel, E., Hugon, J. and Doble, A., *Trends Pharmacol. Sci.*, 1997, 18, 196–203.

Biessels, G. J. and Van Dam, P.S., *Neurosci. Res. Commun.*, 1997, 20, 1–10.

Tomlinson, D.R., Fernyhough, P. and Diemel, L.T., *Diabetes*, 1997, 46(suppl. 2) S43–S–49.

Hamilton, G.S., *Chem. Ind.*, (London) 1998, 4, 127–132.

Ebadi, M., et al., *Neurochem. Int.*, 1997, 30, 347–374.

Lyons, W. E., et al. (*Proc. Natl. Acad.Sci.*, 1994, 91(8), 3191–5).

Holt, Dennis A., et al. (Bioorg. Med Chem., 1998 6(8) 1309–1335.

* cited by examiner

NEUROTROPHIC PYRROLIDINES AND PIPERIDINES, AND RELATED COMPOSITIONS AND METHODS

This application claims the benefit of Provisional application Ser. No. 60/143,006, filed Jul. 9, 1999.

FIELD OF THE INVENTION

This invention relates to novel pyrrolidines and piperidines having neurotrophic activity. These compounds, along with related compositions and methods, are useful in the treatment and prevention of neuronal disorders such as Parkinson's disease, Alzheimer's disease, stroke, multiple sclerosis, amyotrophic lateral sclerosis, diabetic neuropathy and Bell's palsy.

BACKGROUND OF THE INVENTION

Neurodegenerative Diseases

Neurodegenerative diseases constitute a major threat to public health throughout the world. One of the most serious such diseases is Alzheimer's disease ("AD"), a major cause of dementia in aged humans and the fourth most common medical cause of death in the United States. In the U.S., it is estimated that AD afflicts two to three million individuals overall, and more than 5% of the population over the age of 65. Although the exact etiology of AD remains to be defined, the disease is characterized by the presence of a large number of amyloid plaques and neurofibrillary tangles in regions of the brain involved in cognitive function, and degeneration of cholinergic neurons that ascend from the basal forebrain to cortical and hippocampal areas. Currently, there are no effective therapies for AD. Brinton, R. D. and Yamazaki, R. S., *Pharm. Res.*, 1998, 15, 386–398.

Similar to AD, Parkinson's Disease ("PD") is a progressive degenerative disease of the central nervous system ("CNS"). The lifetime incidence of the disease is approximately 2% in the general population. In PD, degeneration of the dopaminergic neurons of the substantia nigra leads to a decrease in dopamine levels in the region of the brain controlling voluntary movement, the corpus striatum. Therefore, standard treatments have focused on the administration of agents, like L-dopa and bromocriptine, which replenish dopamine levels in the affected areas of the brain. Dopaminergic regimens lose their efficacy, however, as nerve cells continue to die and the disease progresses. At the same time the involuntary tremors seen in the early stages of PD advance to periods of difficult movement and, ultimately, to immobility. Therefore, alternative therapies are actively being sought. Pahwa, R. and Koller, W. C., *Drugs Today*, 1998, 34, 95–105.

Neurodegenerative diseases of the somatosensory nervous system also constitute a class of debilitating and potentially lethal conditions. Amyotrophic lateral sclerosis ("ALS") is a fatal disease characterized by progressive degeneration of the upper and lower motor neurons. Although the precise etiology of ALS is unknown, popular theories suggest that excitotoxicity and/or oxidative stress are contributing factors. Riluzole is the first drug approved and marketed for ALS. It possesses antiexcitotoxic properties and has been shown to increase the rate of survival of ALS patients. However, the drug is not a cure, and clinical trials of alternative agents are currently underway. Louvel, E., Hugon, J. and Doble, A., *Trends Pharmacol. Sci.,* 1997, 18, 196–203.

Peripheral neuropathies are secondary to a number of metabolic and vascular conditions. In particular, approximately 30% of patients with diabetes mellitus suffer from some form of peripheral neuropathy that may affect the small myelinated fibers, causing loss of pain and temperature sensation, or the large fibers, causing motor or somatosensory defects. Pharmacotherapeutic intervention tends to be symptomatic, and the best approach to treatment and prevention remains the maintenance of normal blood glucose levels through diet and insulin administration. Biessels, G. J. and Van Dam, P. S., *Neurosci. Res. Commun.,* 1997, 20, 1–10.

A considerable body of evidence now suggests that deficiencies in the levels of certain proteinaceous growth factors, or neurotrophic factors, may play key pathoetiological roles in both peripheral and central neurodegenerative diseases. Tomlinson, D. R., Fernyhough, P. and Diemel, L. T., *Diabetes,* 1997, 46(suppl. 2) S43–S-49; Hamilton, G. S., *Chem. Ind.*, (London) 1998, 4, 127–132; Louvel, E., Hugon, J. and Doble, A., *Trends Pharmacol. Sci.,* 1997, 18, 196–203; Ebadi, M., et al., *Neurochem. Int.,* 1997, 30, 347–374.

These neurotrophic factors can be divided into two structural classes: 1) the neurotrophins, including nerve growth factor ("NGF"); glial cell-derived neurotrophic growth factor ("GDNF"); brain-derived neurotrophic factor ("BDNF"); neurotrophin 3 ("NT-3"); neurotrophin 4/5 ("NT-4/5"); neurotrophin 2 ("NT-2"); and ciliary neurotrophic factor ("CNTF") which is related to the cytokine family of molecules. All neurotrophic factors promote neurite outgrowth, induce differentiation, and suppress programmed cell death or apoptosis in specific subpopulations of peripheral and central neurons. For example, NGF exerts trophic effects on sympathetic and sensory neurons of the dorsal root ganglion and cholinergic neurons of medial septum in the CNS, suggesting potential therapeutic utility in AD. CNTF has trophic actions on a broad cross-section of neurons, including parasympathetic, sensory, sympathetic, motor, cerebellar, hippocampal, and septal neurons. Of particular interest is the fact that CNTF partially prevents the atrophy of skeletal muscle following nerve lesioning but has no effect on innervated muscle, indicating that CNTF is primarily operative in the pathological state. As a result, CNTF is currently being evaluated for its effects in musculoskeletal diseases like ALS.

The clinical utility of proteinaceous neurotrophic agents is severely hampered by their limited bioavailability, especially in the CNS. This necessitates the administration of these agents directly into the brain to induce a therapeutic effect a relatively hazardous and cumbersome route of administration.

Chemical Agents

Lyons, W. E., et al. (*Proc. Natl. Acad. Sci.,* 1994, 91(8), 3191–5) describe the neurotrophic effects of the immunosuppressant drug FK506, which shows neurotrophic activity in cultures of PC12 cells and sensory ganglia:

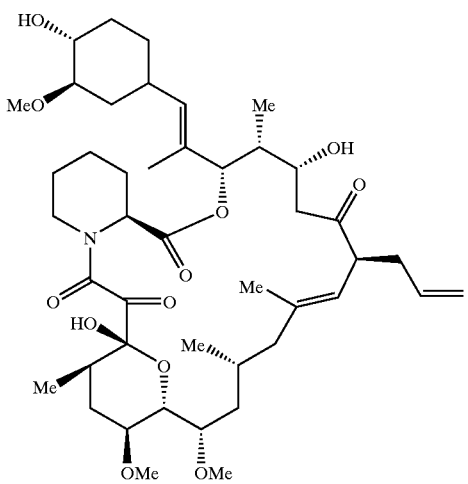

Vertex Pharmaceuticals, Inc. ("Vertex") in South African Application 964852, discloses compounds that are described as useful for inhibiting the rotamase activity of the FKBP12 immunophilin and stimulating neurite outgrowth in cell cultures. These compounds are typified by the following structure:

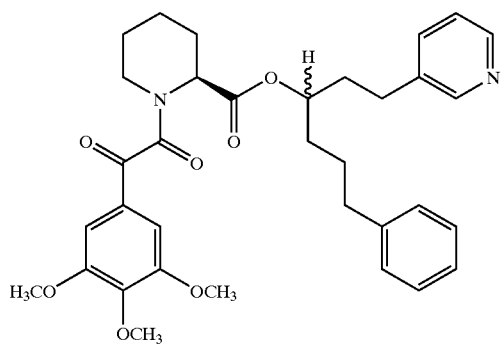

Vertex PCT Application WO 92/19593 discloses a series of compounds that are described as useful for inhibiting the rotamase activity of FK506-binding proteins ("FKBP") and inhibiting T cell activation. These compounds are exemplified by the following structure:

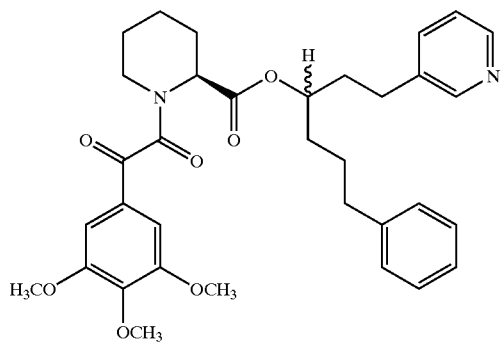

Vertex PCT Application WO 94/07858 discloses a series of compounds that are described as useful multi-drug-resistant cancer cell-sensitizers for maintaining, increasing or restoring the sensitivity of cells to therapeutic or prophylactic agents. The compounds are exemplified by the following structure:

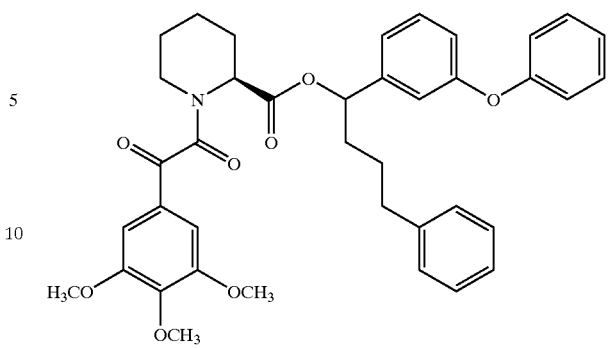

Patents collectively to Guilford Pharmaceuticals, Inc., GPI NIL Holdings, Inc. and Johns Hopkins University School of Medicine (collectively "Guilford") disclose compounds that are described as useful for inhibiting the activity of FKBP-type immunophilins, stimulating neuronal growth and regeneration, and treating neurological disorders.

In particular, Guilford U.S. Pat. No. 5,696,135 and PCT application WO 96/40140 disclose a method of using pipecolic acid derivative compounds, related to FK506 and rapamycin, to treat a neurological disorder in an animal. The compounds therein are described as useful for inhibiting the rotamase activity of an FKBP-type immunophilin, stimulating neuronal growth in chick dorsal root ganglion in vitro, and promoting repair of lesioned sciatic nerves in rats.

Guilford U.S. Pat. No. 5,798,355 discloses a method of using macrocyclic and acyclic pipecolic acid derivatives, which it describes as inhibiting the enzyme activity of FKBP-type immunophilins and stimulating neuronal growth and regeneration.

Guilford U.S. Pat. Nos. 5,614,547 and 5,795,908, and PCT application WO 96/40633, disclose a series of N-glyoxyl-prolyl ester compounds that are described as useful for inhibiting the rotamase activity of the FKBP-12 immunophilin, promoting neuronal growth and regeneration, and treating neurological disorders. The compounds are typified by the following structure:

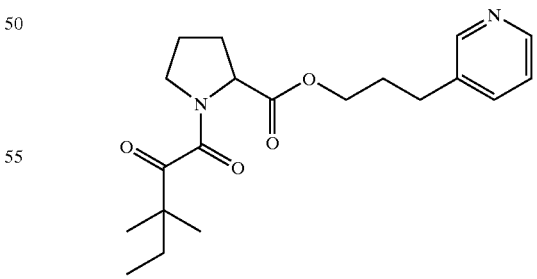

Guilford U.S. Pat. No. 5,801,197 and PCT application WO 97/16190 disclose a series of nonimmunosuppressive pipecolic acid derivatives that are described as useful for the treatment of damaged nerves in animals. The following are representative analogs of the series:

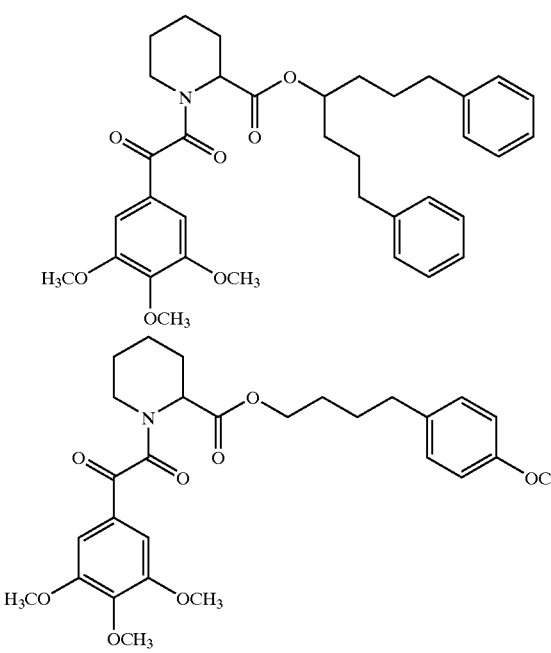

Guilford U.S. Pat. No. 5,721,256 discloses compounds that are described as useful for inhibiting the rotamase activity of FKBP, promoting neuronal growth and regeneration, and effecting neuronal activity in an animal. The series of sulfonamide compounds are typified by the following structure:

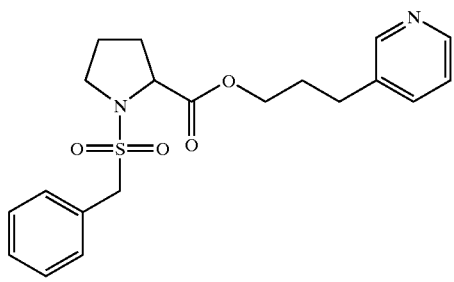

Guilford U.S. Pat. No. 5,801,187 and PCT application WO 98/13355 disclose a series of heterocyclic ester and amide compounds that are described as useful for inhibiting the rotamase activity of FKBP, promoting neuronal growth and regeneration, and effecting neuronal activity in an animal. The compounds are typified by the following structure:

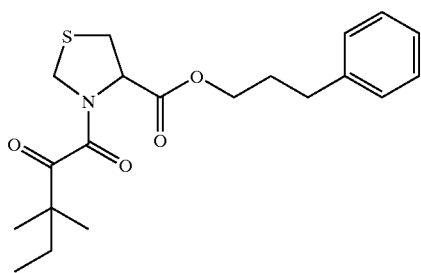

Guilford PCT Application WO 98/13343 discloses a series of heterocyclic thioester and ketone compounds that are described as useful for inhibiting the rotamase activity of FKBP, promoting neuronal growth and regeneration, and effecting neuronal activity in an animal. The compounds are exemplified by the following structure:

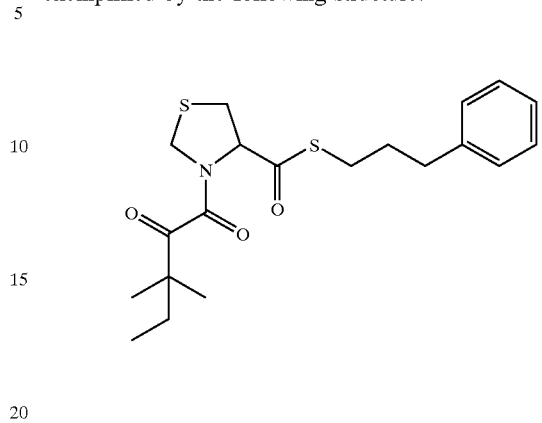

Guilford PCT Application WO 98/29116 discloses a series of N-linked sulfonamide compounds of heterocyclic thioesters that are described as useful for inhibiting the rotamase activity of FKBP, promoting neuronal growth and regeneration, and effecting neuronal activity in an animal. The compounds are typified by the following structure:

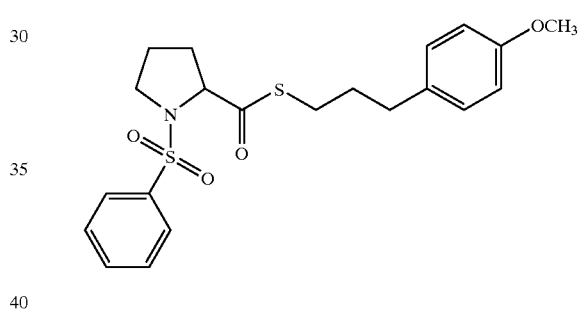

Guilford PCT Application WO 98/29117 discloses a series of N-linked ureas and carbamate compounds of heterocyclic thioesters that are described as useful for inhibiting the rotamase activity of FKBP, promoting neuronal growth and regeneration, and effecting neuronal activity in an animal. The compounds are typified by the following structure:

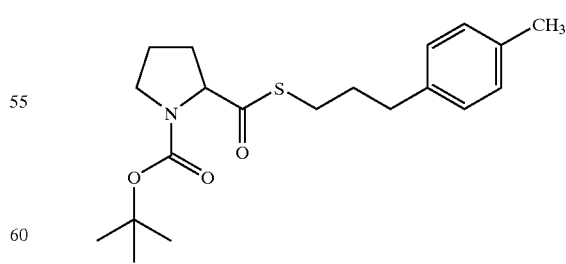

Guilford PCT Application WO 98/37882 discloses a method of using small molecule carbamate and urea com pounds that are described as useful for inhibiting the rotamase activity of FKBP-type immunophilins and stimulating neuronal growth and regeneration. The compounds are typified by the following structure:

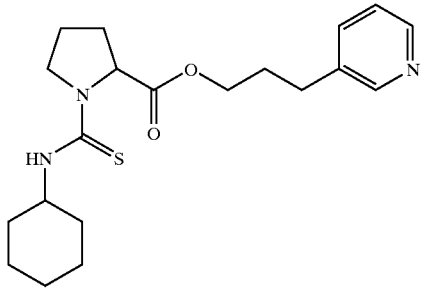

Guilford PCT Application WO 98/37885 discloses a series of N-oxide compounds of heterocyclic esters, amides, thioesters and ketones that are described as useful for inhibiting the rotamase activity of FKBP, promoting neuronal growth and regeneration and treating neurological disorders in an animal. The compounds are typified by the following structure:

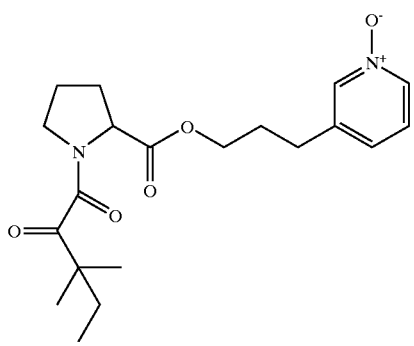

Guilford PCT Application WO 98/25950 discloses a series of tetra- and pentapeptide compounds containing at least two proline residues, which compounds are described as useful for inhibiting the rotamase activity of cyclophilin, promoting neuronal growth and regeneration, and effecting neuronal activity in an animal.

Patents and publications collectively to Ariad Gene Therapeutics, Inc. ("Ariad") disclose agents that are described as useful for multimerizing immunophilins, gene therapy applications, the activation of gene transcription, the actuation of apoptosis, or the triggering of other biological events in engineered cells growing in culture or in whole organisms.

In particular, Ariad PCT Applications WO 96/06097, WO 97/31898, WO 97/31899 and Holt, D. A., et al. (*Bioorg. Med. Chem.*, 1998, 6(8), 1309–1335) disclose compounds that include a series of multimerizing agents represented by the following structure:

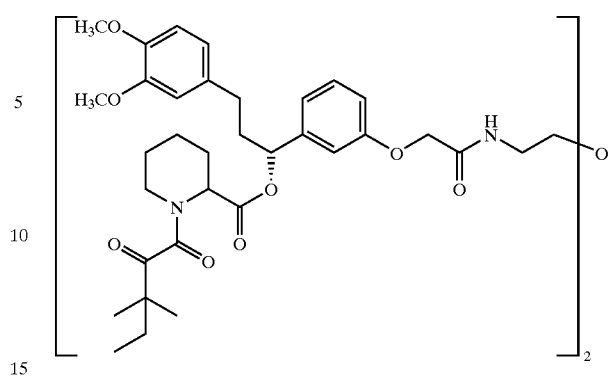

Patents collectively to Cephalon, Inc. and Kyowa Hakko Kogyo Co., Ltd. (collectively "Cephalon") describe small molecule neurotrophic agents with potential clinical utility in the treatment of neurodegenerative diseases.

In particular, Cephalon U.S. Pat. Nos. 5,756,494, 5,621,101 and 5,461,146, and PCT Applications WO 96/13506 and WO 94/02488, disclose a series of indolocarbazole protein kinase inhibitors that are described as having neurotrophic effects in central cholinergic neurons, the dorsal root ganglion and the spinal cord. These compounds are typified by the following structure:

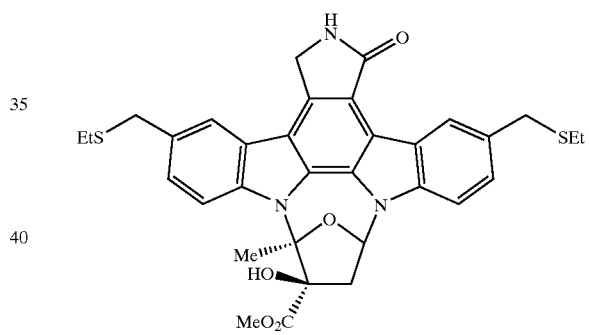

None of the known agents discussed herein has ever been demonstrated having therapeutic or prophylactic efficacy against neurodegenerative disorders in humans. Thus, there exists a strong and unmet need for agents having such efficacy.

SUMMARY OF THE INVENTION

Figure 1:
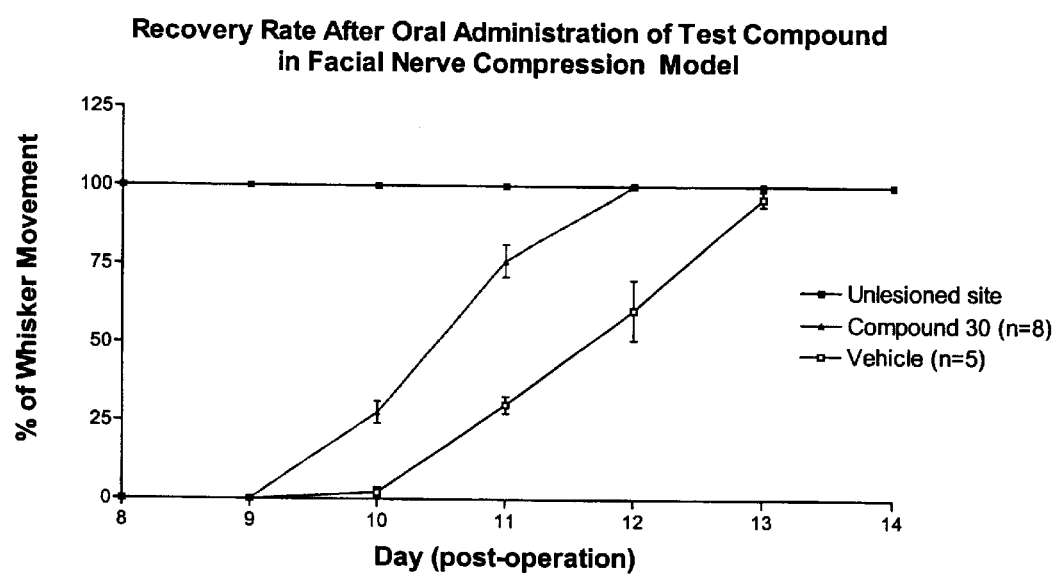
FIG. 1 shows the in vivo biological activity of instant Compound 30 using the rat facial nerve compression model. In this model, compressing the facial nerve causes paralysis of the whisker muscle on that side of the face. The untreated facial nerve on the other side functions as an internal control. Treatment with Compound 30 demonstrated that whisker movement on the paralyzed side was restored more rapidly compared to a vehicle and the internal control. The whisker movement recovery rate on the paralyzed side compared to the vehicle and internal control is shown in this FIGURE.

This invention provides a compound having the structure

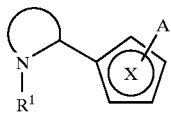

or a pharmaceutically acceptable salt thereof, wherein (a) $R^1$ is selected from the group consisting of H, $COCOR^2$, $COOR^3$ and $SO_2R^3$,
  (i) $R^2$ being selected from the group consisting of $O-C_{1-6}$ straight or branched alkyl, $C_{1-6}$ straight or branched alkyl, $C_{1-6}$ straight or branched alkenyl, $C_{5-7}$ cycloalkyl, 2-thienyl, 3-thienyl or phenyl, the phenyl having one to three substituents independently selected from the group consisting of H, lower alkyl, lower alkoxyl, hydroxyl and halogen, and
  (ii) $R^3$ being phenylalkyl, wherein the phenyl has one to three substituents independently selected from the group consisting of H, lower alkyl, lower alkoxyl, hydroxyl and halogen;

(b)

is a four to six-membered heterocyclic ring, wherein no more than one ring atom is O or S;

(c)

is a five-membered heterocyclic ring having from two to three heteroatoms selected from the group consisting of N, O and S, at least one such heteroatom being N; and (d) A is selected from the group consisting of $COO(CH_2)_mAr$,

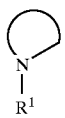

(such $R^1$ being the same as or different than the $R^1$ described in part (a)), $CONR^4(CH_2)_mAr$, $(CH_2)_mO(CH_2)_nAr$ and $(CH_2)_nAr$,
  (i) $R^4$ being H or $C_{1-4}$ alkyl;
  (ii) Ar being selected from the group consisting of 2-pyridyl, 3-pyridyl, 4-pyridyl and phenyl, the phenyl having between one and three substituents independently selected from the group consisting of H, lower alkyl, lower alkoxyl, hydroxyl and halogen;
  (iii) m being 1–4; and
  (iv) n being 0–4.

This invention also provides a compound having the structure

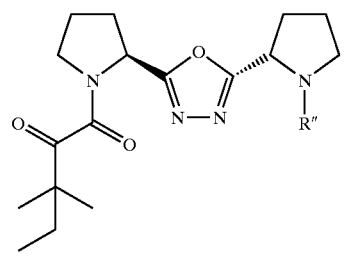

or a pharmaceutically acceptable salt thereof, wherein R" is C(1–4)-straight or branched alkyl.

This invention further provides a compound having the structure

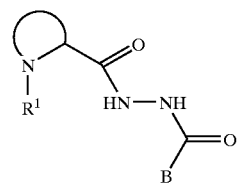

or a pharmaceutically acceptable salt thereof, wherein (a) $R^1$ is selected from the group consisting of H, $COCOR^2$, $COOR^3$ and $SO_2R^3$,
  (i) $R^2$ being selected from the group consisting of $O-C_{1-6}$ straight or branched alkyl, $C_{1-6}$ straight or branched alkyl, $C_{1-6}$ straight or branched alkenyl, C cycloalkyl, 2-thienyl, 3-thienyl or phenyl, the phenyl having one to three substituents independently selected from the group consisting of H, lower alkyl, lower alkoxyl, hydroxyl and halogen, and
  (ii) $R^3$ being phenylalkyl, wherein the phenyl has one to three substituents independently selected from the group consisting of H, lower alkyl, lower alkoxyl, hydroxyl and halogen;

(b)

is a four to six-membered heterocyclic ring, wherein no more than one ring atom is O or S;

(c)

is a five-membered heterocyclic ring having from two to three heteroatoms selected from the group consisting of N, O and S, at least one such heteroatom being N; and (d) B is $(CH_2)_n Ar$ or

wherein n is 0–4.

This invention provides a method of stimulating neuronal growth comprising contacting neurons with an effective amount of one of the instant compounds. This invention also provides a pharmaceutical composition comprising one of the instant compounds and a pharmaceutically acceptable carrier.

This invention further provides a method of treating a subject afflicted with a disorder characterized by neuronal damage caused by disease or trauma, comprising administering to the subject a therapeutically effective amount of the instant pharmaceutical composition. Finally, this invention provides a method of inhibiting in a subject the onset of a disorder characterized by neuronal damage caused by disease, comprising administering to the subject a prophylactically effective amount of the instant pharmaceutical composition.

DETAILED DESCRIPTION OF THE INVENTION

This invention provides novel pyrrolidines and piperidines having surprising neurotrophic activity. These compounds, along with related pharmaceutical compositions and methods, are useful in the treatment and prevention of neuronal disorders such as Parkinson's disease, Alzheimer's disease, stroke, multiple sclerosis, amyotrophic lateral sclerosis, diabetic neuropathy and Bell's palsy.

Specifically, this invention provides a compound having the structure

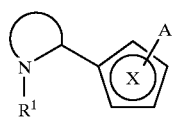

or a pharmaceutically acceptable salt thereof, wherein (a) $R^1$ is selected from the group consisting of H, $COCOR^2$, $COOR^3$ and $SO_2R^3$,
 (i) $R^2$ being selected from the group consisting of $O-C_{1-6}$ straight or branched alkyl, $C_{1-6}$ straight or branched alkyl $C_{1-6}$ straight or branched alkenyl, $C_{5-7}$ cycloalkyl, 2-thienyl, 3-thienyl or phenyl, the phenyl having one to three substituents independently selected from the group consisting of H, lower alkyl, lower alkoxyl, hydroxyl and halogen, and
 (ii) $R^3$ being phenylalkyl, wherein the phenyl has one to three substituents independently selected from the group consisting of H, lower alkyl, lower alkoxyl, hydroxyl and halogen;

(b)

is a four to six-membered heterocyclic ring, wherein no more than one ring atom is O or S;

(c)

is a five-membered heterocyclic ring having from two to three heteroatoms selected from the group consisting of N, O and S, at least one such heteroatom being N; and (d) A is selected from the group consisting of $COO(CH_2)_m Ar$,

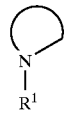

(such $R^1$ being the same as or different than the $R^1$ described in part (a)), $CONR^4(CH_2)_m Ar$, $(CH_2)_m O(CH_2)_n Ar$ and $(CH_2)_n Ar$, (i) $R^4$ being H or $C_{1-4}$ alkyl;
(ii) Ar being selected from the group consisting of 2-pyridyl, 3-pyridyl, 4-pyridyl and phenyl, the phenyl having between one and three substituents independently selected from the group consisting of H, lower alkyl, lower alkoxyl, hydroxyl and halogen;
(iii) m being 1–4; and
(iv) n being 0–4.

In one embodiment, this compound has the following structure, wherein each $R^1$ is either the same as, or different than, the other.

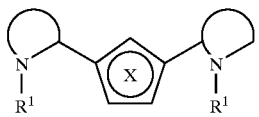

In the preferred embodiment, this compound is selected from the group consisting of instant Compounds 4, 14, 30, 31, 35, 38, 43, 44, 55, 56, 58, 60, 62 and 64.

This invention also provides a compound having the structure

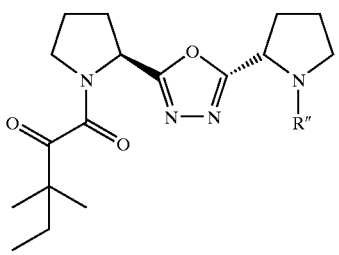

or a pharmaceutically acceptable salt thereof, wherein R" is C(1-4)-straight or branched alkyl.

This invention further provides a compound having the structure

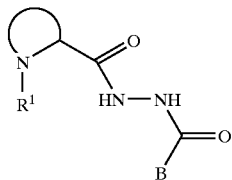

or a pharmaceutically acceptable salt thereof, wherein (a) $R^1$ is selected from the group consisting of H, $COCOR^2$, $COOR^3$ and $SO_2R^3$,
  (i) $R^2$ being selected from the group consisting of O—$C_{1-6}$ straight or branched alkyl $C_{1-6}$ straight or branched alkyl $C_{1-6}$ straight or branched alkenyl, $C_{5-7}$ cycloalkyl, 2-thienyl, 3-thienyl or phenyl, the phenyl having one to three substituents independently selected from the group consisting of H, lower alkyl, lower alkoxyl, hydroxyl and halogen, and
  (ii) $R^3$ being phenylalkyl, wherein the phenyl has one to three substituents independently selected from the group consisting of H, lower alkyl, lower alkoxyl, hydroxyl and halogen;

(b)

is a four to six-membered heterocyclic ring, wherein no more than one ring atom is O or S;

(c)

is a five-membered heterocyclic ring having from two to three heteroatoms selected from the group consisting of N, O and S, at least one such heteroatom being N; and (d) B is $(CH_2)_n Ar$ or

wherein n is 0–4.

In the preferred embodiment, this compound is selected from the group consisting of instant Compounds 24, 26, 37 and 59.

The instant compounds can be isolated and used as free bases. They can also be isolated and used as pharmaceutically acceptable salts. Examples of such salts include hydrobromic, hydroiodic, hydrochloric, perchloric, sulfuric, maleic, fumaric, malic, tartaric, citric, benzoic, mandelic, methanesulfonic, hydroethanesulfonic, benzenesulfonic, oxalic, palmoic, 2-naphthalenesulfonic, p-toluenesulfonic, cyclohexanesulfamic and saccharic.

This invention further provides a method of stimulating neuronal growth comprising contacting neurons with an effective amount of one of the instant compounds. The contacting can be performed, for example, in vitro, ex vivo, or in vivo.

This invention still further provides a pharmaceutical composition comprising one of the instant compounds and a pharmaceutically acceptable carrier.

Pharmaceutically acceptable carriers are well known to those skilled in the art and include, but are not limited to, from about 0.01 to about 0.1 M and preferably 0.05 M phosphate buffer or 0.8% saline. Such pharmaceutically acceptable carriers can be aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, ethanol, alcoholic/aqueous solutions, glycerol, emulsions or suspensions, including saline and buffered media. Oral carriers can be elixirs, syrups, capsules, tablets and the like. The typical solid carrier is an inert substance such as lactose, starch, glucose, methyl-cellulose, magnesium stearate, dicalcium phosphate, mannitol and the like. Parenteral carriers include sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like. All carriers can be mixed as needed with disintegrants, diluents, granulating agents, lubricants, binders and the like using conventional techniques known in the art.

This invention further provides a method of treating a subject afflicted with a disorder characterized by neuronal damage caused by disease or trauma, comprising administering to the subject a therapeutically effective amount of the instant pharmaceutical composition.

As used herein, the term "subject" includes, without limitation, any animal or artificially modified animal. In the preferred embodiment, the subject is a human.

Administering the instant pharmaceutical composition can be effected or performed using any of the various methods known to those skilled in the art. The instant compounds can be administered, for example, intravenously, topically, intramuscularly, orally, subcutaneously, and directly into the cerebrospinal fluid and/or brain. In the preferred embodiment, the instant pharmaceutical composition is administered orally. Additionally, administration can comprise giving the subject a plurality of dosages over a suitable period of time. Such administration regimens can be determined according to routine methods.

Disorders characterized by neuronal damage are numerous and include the following, without limitation: Alzheimer's disease, Pick's disease, diffuse Lewy body disease, progressive supranuclear palsy (Steel-Richardson syndrome), multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohifart-Kugelberg-Welander disease, spastic paraparesis, progressive multifocal leukoencephalopathy, and prion diseases (including Creutzfeldt-Jakob, Gerstmann-Sträussler-Scheinker disease, Kuru and fatal familial insomnia).

Other disorders include, without limitation, diffuse white matter disease (Binswanger's disease), head trauma and diffuse brain damage, spinal cord injury, intracranial and intravertebral lesions (including, but not limited to, contusion, penetration, shear, compression and laceration), stroke resulting from cerebral ischemia or infarction, embolic occlusion and thrombotic occlusion, and intracranial hemorrhage of any type (including, but not limited to, epidural, subdural, subarachnoid and intracerebral).

Further disorders include, without limitation, demyelinating diseases such as multiple sclerosis; polyradiculoneuritis (Guillain-Barre syndrome); subacute demyelinating polyneuropathies; brain lesions induced by acute disseminated encephalomyelitis, acute hemorrhagic leukoencephalitis or systemic lupus erythematosus; Behcet's syndrome associated with multifocal brain lesions, neuropathy and/or myelopathy; sarcoidosis associated with nerve damage or atrophy or myelopathy; bacterial or viral infections resulting in brain, spinal cord, nerve damage, meningoradiculitis, and/or myelopathy; subacute combined degeneration; transverse myelitis; Leber's hereditary neuropathy; subacute necrotic encephalopathy (Leigh's disease); mitochondrial encephalopathy with demyelination; metachromatic leukodystrophy; Krabbe's disease; Fabry's disease; adrenoleukodystrophy; neuromyelitis optica (Devic's syndrome); demyelinating Schwannopathies; cranial and peripheral neuropathies including, but not limited to, Djérine-Soffas neuropathy and its variants; Charcot-Marie-Tooth disease and its variants; hereditary polyneuropathies; sensory and motor neuropathies; axonal neuropathies; adrenomyeloneuropathy; Refsum's disease; neuropathies due to porphyria, acute or chronic toxins/drugs intoxications with either axonal, demyelinating, sensory, motor and/or autonomic involvement; Friedreich's ataxia; ataxia-telangiectasia; and metachromatic leukodystrophy; chronic neuropathies, including, but not limited to, diabetes mellitus and other metabolic dysregulations and dysproteinemias (metabolic neuropathies including those due to alcoholism); and inflammatory/immunological processes (inflammatory neuropathies, herpes zoster-associated neuropathy, and leprous neuritis).

Further disorders include, without limitation, the traumatic neuropathies of the peripheral or cranial nerves, Bell's palsy and other facial nerve neuropathies, trigeminal neuropathy, vestibular neuropathy, accessory nerve neuropathy, vagal neuropathy, glossopharyngeal neuropathy, optic nerve neuropathy, oculomotor nerve neuropathy, multiple cranial nerves palsies, plexopathies, root disorders, idiopathic brachial neuritis, plexitis, multifocal neuropathy, and autonomic nervous system neuropathies.

In one embodiment of this invention, the disorder treated is caused by disease, and is selected from the group consisting of Parkinson's disease, Alzheimer's disease, stroke, multiple sclerosis, amyotrophic lateral sclerosis, diabetic neuropathy and Bell's palsy. In another embodiment, the disorder treated is caused by trauma to the brain, spinal cord, or peripheral nerves.

Finally, this invention provides a method of inhibiting in a subject the onset of a disorder characterized by neuronal damage caused by disease, comprising administering to the subject a prophylactically effective amount of the instant pharmaceutical composition.

In one embodiment, the disorder inhibited is selected from the group consisting of Parkinson's disease, Alzheimer's disease, stroke, multiple sclerosis, amyotrophic lateral sclerosis, diabetic neuropathy and Bell's palsy.

As used herein, a "therapeutically effective dose" of a pharmaceutical composition is an amount sufficient to stop, reverse or reduce the progression of a disorder. A "prophylactically effective dose" of a pharmaceutical composition is an amount sufficient to inhibit the onset of a disorder, i.e., eliminate, ameliorate and/or delay the disorder's onset. Methods are known in the art for determining therapeutically and prophylactically effective doses for the instant pharmaceutical composition. The effective dose for administering the pharmaceutical composition to a human, for example, can be determined mathematically from the results of animal studies.

In one embodiment, the therapeutically and/or prophylactically effective dose is a dose sufficient to deliver from about 0.01 mg/kg to about 200 mg/kg of body weight of the instant compound. In another embodiment, the therapeutically and/or prophylactically effective dose is a dose sufficient to deliver from about 0.1 mg/kg to about 100 mg/kg of body weight. In the preferred embodiment, the therapeutically and/or prophylactically effective dose is a dose sufficient to deliver from about 1 mg/kg to about 30 mg/kg of body weight.

This invention will be better understood by reference to the Experimental Details which follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

Experimental Details

I. General Synthetic Methods

Representative compounds of the present invention can be synthesized in accordance with the general synthetic methods described below and illustrated in the following schemes. In these schemes, Arabic and Roman numerals are used interchangeably to refer to various compounds. Compounds referred to in this section by Arabic numerals are not to be confused with the specific compounds referred to by Arabic numerals in Table 1 and elsewhere herein.

Scheme 1

Compound 1a, of the general formula:

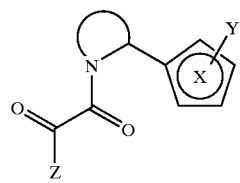

1a

[wherein

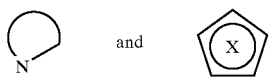

are as used herein; Z is ($C_1$–$C_6$)-straight or branched alkyl, ($C_1$–$C_6$)-straight or branched alkenyl or ($C_5$–$C_7$)cycloalkyl, or phenyl; wherein the phenyl ring has one to three substituents which are independently selected from the group consisting of hydrogen, lower alkyl, lower alkoxy, hydroxy and halogen; Y is A or lower alkoxycarbonyl; and A is as used herein] can be prepared by reacting Compound 1b, of the general formula:

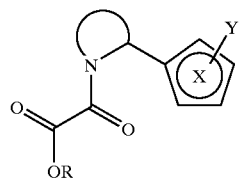

1b

[wherein

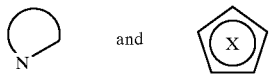

are as used herein; R is ($C_1$–$C_6$)-straight or branched alkyl; Y is A or lower alkoxycarbonyl; and A is as used herein] with a suitably protected Grignard reagent in an inert solvent such as tetrahydrofuran or diethyl ether at temperatures ranging from about −78° C. to about 0° C. for about 2 h to about 6 h, depending on the reactivity of the oxamate.

Scheme 2

Alternatively, Compounds 1a and 1b, [wherein 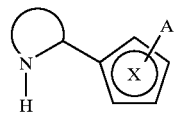 and are as used herein; R is ($C_1$–$C_6$)-straight or branched alkyl; Y is A or lower alkoxycarbonyl; A is as used herein; and Z is ($C_1$–$C_6$)-straight or branched alkyl, ($C_1$–$C_6$)-straight or branched alkenyl or ($C_5$–$C_7$)cycloalkyl, 2-thienyl, 3-thienyl, or phenyl; wherein the phenyl ring has one to three substituents which are independently selected from the group consisting of hydrogen, lower alkyl, lower alkoxy, hydroxy and halogen] can be prepared by reacting Compound 2, of the general formula:

2

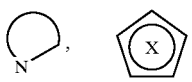

[wherein

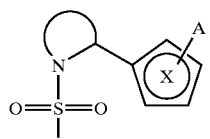

and A are as used herein] with a suitably protected glyoxylic acid chloride or alkyl oxalyl chloride in an inert solvent such as methylene chloride for about 2 h to about 6 h. Generally, the reaction is conducted in the presence of an organic amine such as diisopropylethylamine or triethylamine from about 0° C. to about 37° C.

In the case of Compound 1a, with definitions as above, this transformation can also be effected by the condensation of Compound 2, with definitions as above, with a suitably protected glyoxylic acid in the presence of a coupling agent such as diisopropylcarbodiimide, dicyclohexylcarbodiimide, or benzotriazol-1-yloxytris (dimethylamino)phosphonium hexafluorophosphate (Castro's reagent) in an inert solvent, such as tetrahydrofuran, dimethylformamide, or methylene chloride at temperatures ranging from about 0° C. to about 37° C. for about 2 h to about 24 h.

Scheme 3

Compound 3, of the general formula:

3

[wherein and A are as used herein; and $R^3$ is phenylalkyl; wherein the phenyl ring has one to three substituents which are independently selected from the group consisting of hydrogen, lower alkyl, lower alkoxy, hydroxy and halogen] can be prepared by reacting Compound 2, with definitions as above, with a phenylalkylsulfonyl chloride in an inert solvent such as methylene chloride for about 2 h to about 24 h. Generally, the reaction is conducted in the presence of an organic amine such as diisopropylethylamine or triethylamine at temperatures ranging from about 0° C. to about 37° C.

Scheme 4

Compound 2, with definitions as above, can be prepared from Compound 4, of the general formula:

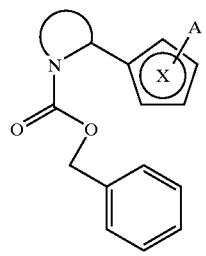

4 with definitions as above, by standard methods for removal of the N-benzyloxycarbonyl group. Such methods include catalytic hydrogenation over a noble metal catalyst such as palladium on carbon in an alcoholic solvent for about 4 h to about 24 h generally at room temperature (RT), or reaction with boron tribromide in an inert solvent such as methylene chloride for about 2 h to about 6 h at temperatures ranging from about −78° C. to about 25° C., or reaction with a strong acid such as hydrobromic acid in acetic acid for about 2 h to about 6 h at temperatures ranging from about 20° C. to about 100° C. In the case of the latter method, the product is frequently isolated as the hydrobromide salt.

Scheme 5

Compound 5a, of the general formula:

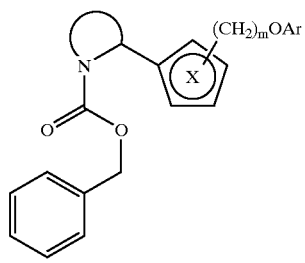

5a

[wherein

m, and Ar are as used herein] can be prepared by reacting Compound 5b, of the general formula:

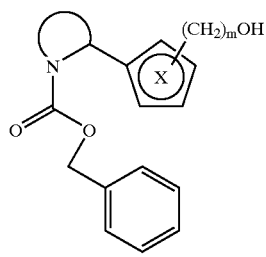

5b with definitions as above, with an aromatic or heteroaromatic alcohol such as 3-hydroxypyridine. The reaction is generally conducted in the presence of an azodicarboxylic acid derivative such as diethyl azodicarboxylate or 1,1′-(azodicarbonyl)dipiperdine and a phosphine derivative such as triphenylphosphine or tri-n-butylphosphine in an inert solvent such as tetrahydrofuran or toluene for about 12 h to about 24 h. The reaction temperature can range from about 20° C. to about 65° C.

Scheme 6

Compounds 6a and 6b, of the general formulae:

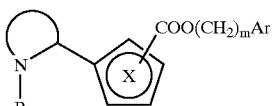

6a

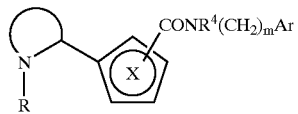

6b

[wherein

$R^4$, m, and Ar are as used herein; R is $COCOR^2$, $COOR^3$ or $SO_2R^3$; and $R^2$ and $R^3$ are as used herein] can be prepared by reacting Compound 6c, of the general formula:

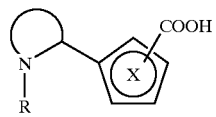

6c

[wherein

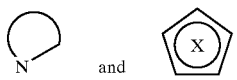

are as used herein; R is $COCOR^2$, $COOR^3$ or $SO_2R^3$; and $R^2$ and $R^3$ are as used herein] with an arylalkylamine or arylalkanol derivative. The reaction is effected through the intermediacy of an acyl azide or mixed anhydride by adding a reagent such as diphenylphosphoryl azide, isopropenylchloroformate, or isobutylchloroformate together with an organic amine base such as triethylamine or diisopropylethylamine in an inert solvent such as tetrahydrofuran or dimethylformamide. An acylation catalyst such as dimethylaminopyridine also may be added. The reaction is generally conducted at temperatures ranging from about 0° C. to about 25° C. for about 12 h to about 24 h.

Scheme 7

Compound 5b can be prepared through reduction of Compound 7, of the general formula:

7

[wherein and m are as used herein; and R is lower alkyl] with a metal hydride reducing agent such as lithium borohydride or the combination of sodium borohydride/lithium chloride. The reaction generally is run in an alcoholic solvent such as ethanol or methanol, with or without added tetrahydrofuran, at temperatures ranging from about RT to about 65° C. for about 24 h to about 72 h.

Scheme 8

Compound 6c can be prepared by reacting Compound 8, of the general formula:

8

[wherein are as described previously; R is $COCOR^2$, $COOR^3$ or $SO_2R^3$; $R^2$ and $R^3$ are as used herein; and R' is lower alkyl], with an alkali metal hydroxide or alkali metal carbonate such as lithium hydroxide, sodium hydroxide or potassium carbonate in a mixed aqueous solvent system such as tetrahydrofuran/water or ethanol/water at temperatures ranging from about RT to about 80° C. for about 3 h to about 24 h.

Scheme 9

Compound 9a, of the general formula:

9a

[wherein and m are as used herein; and R is lower alkyl] can be prepared by condensation of Compound 9b, of the general formula:

9b with definitions as above, with an α-bromoketoester such as ethyl bromopyruvate or ethyl γ-bromoacetoacetate, in an alcoholic solvent such as ethanol. The reaction can be conducted at temperatures ranging from about 20° C. to about 80° C. for about 2 h to about 24 h.

Scheme 10

In a similar fashion, Compound 10a, of the general formula:

10a with definitions as above, can be prepared by condensing Compound 9b with Compound 10b, of the general formula:

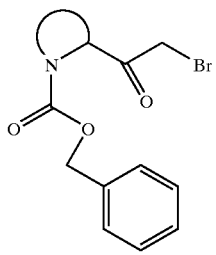

10b with definitions as above, in an alcoholic solvent such as ethanol at about 80° C. for about 3 h to about 24 h.

Scheme 11

Compound 10b, with the definitions as above, can be prepared by reacting Compound 11, of the general formula:

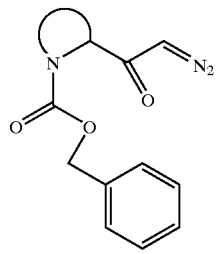

11 with definitions as above, with hydrogen bromide in an inert solvent such as diethyl ether. Generally, the reaction is run from about 0° C. to about 25° C. until the evolution of $N_2$ is complete.

Scheme 12

Compound 11 can be prepared from Compound 12, of the general formula:

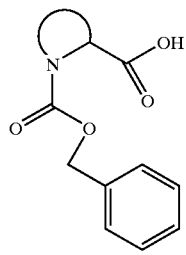

12

[wherein

is as described previously] by reacting the acid chloride derivative of Compound 12 with diazomethane or trimethysilyldiazomethane in the presence of an organic base such as triethylamine or diisopropylethylamine. The reaction generally is conducted in an inert solvent such as tetrahydrofuran, acetonitrile, or a combination of both at temperatures ranging from about 0° C. to about 25° C. for about 2 h to about 24 h. The acid chloride can be obtained from the corresponding acid using standard methods in the literature such as reaction with oxalyl chloride in an inert solvent such as methylene chloride or tetrahydrofuran in the presence of a catalytic amount of dimethylformamide.

Scheme 13

Compound 13, of the general formula:

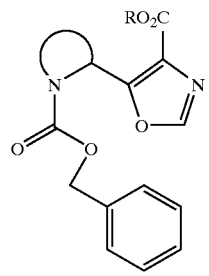

13

[wherein

is as used herein; and R is lower alkyl] can be prepared by reacting Compound 12 with the anion derived from an alkyl isocyanoacetate in a polar, inert solvent such as dimethylformamide for about 12 h to about 24 h. Generally, an alkali metal carbonate, such as potassium carbonate, is used to generate the anion. To facilitate the reaction, the carboxylic acid of Compound 12 is converted to an active species in situ, such as an acyl azide, by reaction with diphenylphosphorylazide.

Scheme 14

Compound 14a, of the general formula:

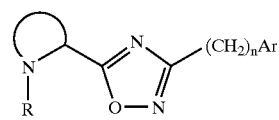

14a

[wherein

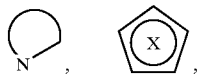

and Ar are as used herein; R is $COCOR^2$, $COOR^3$ or $SO_2R^3$; and $R^2$ and $R^3$ are as used herein] can be prepared by combining Compound 14b, of the general formula:

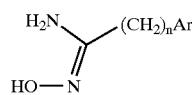

14b

[wherein Ar is as used herein] with Compound 14c, of the general formula:

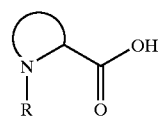

14c

[wherein

is as used herein; R is COCOR$^2$, COOR$^3$ or SO$_2$R$^3$; and R$^2$ and R$^3$ are as used herein] in the presence of a coupling agent such as water-soluble carbodiimide, diisopropylcarbodiimide or dicyclohexylcarbodiimide in an inert solvent such as diglyme or dioxane. Generally, the reaction is run at temperatures ranging from about 50° C. to about 110° C. for about 5 h to about 24 h.

Compound 14b can be prepared by reaction of aralkylnitriles with hydroxylamine hydrochloride in a polar, protic solvent such as ethanol in the presence of an inorganic base such as potassium carbonate. Generally, the reaction is conducted at temperatures ranging from about 20° C. to about 100° C. for about 12 h to about 72 h.

Scheme 15

Compound 15a, of the general formula:

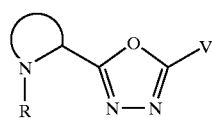

15a

[wherein R is COCOR$^2$, COOR$^3$ or SO$_2$R$^3$; R$^2$ and R$^3$ are as used herein; V is (CH$_2$)$_n$Ar or

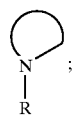

and Ar is as used herein] can be prepared by reacting Compound 15b, of the general formula:

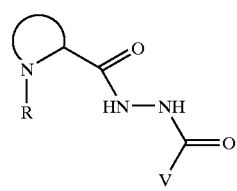

15b

[wherein R is COCOR$^2$, COOR$^3$ or SO$_2$R$^3$; R$^2$ and R$^3$ are as used herein; V is (CH$_2$)$_n$Ar or

and Ar is as used herein] with a cyclodehydrating reagent such as thionyl chloride in pyridine, hexamethyldisilazane in the presence of tetra-n-butylammonium fluoride and imidazole, Et$_3$N$^+$S(O)$_2$N$^-$COOMe (Burgess Reagent), or triflic anhydride in the presence of triethylamine. In the case of thionyl chloride in pyridine, the initial reaction with the bisacylhydrazine derivative is conducted at about 0° C. for about 2 h to about 6 h. Subsequent closure to the oxadiazole is carried out in an inert solvent, such as toluene, for about 3 h to about 24 h at temperatures ranging from about 80° C. to about 150° C. Reaction of the bisacylhydrazine derivative with hexamethydisilazane generally is conducted in an inert solvent, such as toluene or chlorobenzene, at temperatures ranging from about 80° C. to about 150° C. for about 6 h to about 72 h. In the case of the Burgess Reagent, the reaction with the bisacylhydrazine derivative generally is conducted at about RT for about 24 h to about 72 h in an inert solvent such as tetrahydrofuran. Reaction of the bisacylhydrazine derivative with triflic anhydride and triethylamine generally is conducted in an inert solvent, such as methylene chloride, tetrahydrofuran, or diethyl ether, at temperatures ranging from about 0° C. to about 25° C. for about 1 h to about 24 h.

Scheme 16

Compound 15b can be prepared by reacting the mixed anhydride or acid chloride derivative of Compound 14c, [wherein

is as used herein; R is COCOR$^2$, COOR$^3$ or SO$_2$R$^3$, and R$^2$ and R$^3$ are as used herein] with Compound 16a, of the general formula:

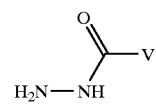

16a

[wherein V is (CH$_2$)$_n$Ar or

and Ar is as used herein]. Generally, the reaction is conducted in an inert solvent, such as tetrahydrofuran or methylene chloride with or without the addition of a tertiary amine base, such as triethylamine or diisopropylethylamine, at about 0° C. to about 25° C. for about 6 h to about 24 h. The mixed anhydride or acid chloride derivatives can be obtained from the corresponding acid using standard methods in the literature such as reaction with isobutylchloroformate or ethylchloroformate in the presence of triethylamine or diisopropylethylamine, or reaction with oxalyl chloride in an inert solvent such as methylene chloride or tetrahydrofuran in the presence of a catalytic amount of dimethylformamide.

In the case of Compound 15b, with definitions as above, this transformation can also be effected by the condensation of Compound 16a, with definitions as above, with Compound 14c in the presence of a coupling agent such as diisopropylcarbodiimide, dicyclohexylcarbodiimide, or benzotriazol-1-yloxytris(dimethylamino)phosphonium hexafluorophosphate (Castro's reagent) in an inert solvent, such as tetrahydrofuran, dimethylformamide, or methylene chloride at temperatures ranging from about 0° C. to about 37° C. for about 2 h to about 24 h.

Compound 16a [wherein V is (CH$_2$)$_n$Ar or

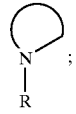

and Ar is as used herein] can be prepared from the corresponding lower alkyl ester derivative by reaction with hydrazine in an alcoholic solvent, such as ethanol, at reflux temperature for about 6 h to about 24 h. Alternatively, Compound 16a can be prepared from the corresponding carboxylic acid derivative, through the intermediacy of the trimethylsilyl ester, by reaction with hydrazine in an inert solvent, such as methylene chloride, tetrahydrofuran, or dimethylformamide, at temperatures ranging from about 0° C. to about 25° C. for about 1 h to about 24 h. The silyl ester can be prepared in situ by methods commonly employed by those trained in the art, such as reaction of the carboxylic acid with N,O-bis-trimethylacetamide at temperatures ranging from about 0° C. to about 25° C. for about 1 h to about 6 h.

Scheme 17

Compound 17, of the general formula:

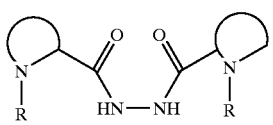

17

[wherein

is as used herein; R is COCOR$^2$, COOR$^3$ or SO$_2$R$^3$; and R$^2$ and R$^3$ are as used herein] can be prepared by reacting the mixed anhydride or acid chloride derivative of Compound 14c

[wherein

is as used herein; R is COCOR$^2$, COOR$^3$ or SO$_2$R$^3$; and R$^2$ and R$^3$ are as used herein] with about 0.5 to about 1 equivalent of hydrazine monohydrate at temperatures ranging from about 0° C. to about 25° C. for about 4 h to about 24 h.

Generally, the reaction is conducted in an inert solvent, such as tetrahydrofuran or methylene chloride with or without the addition of a tertiary amine base, such as triethylamine or diisopropylethylamine. The mixed anhydride or acid chloride derivatives can be obtained from the corresponding acid using standard methods in the literature such as reaction with isobutylchloroformate or ethylchloroformate in the presence of triethylamine or diisopropylethylamine, or reaction with oxalyl chloride in an inert solvent such as methylene chloride or tetrahydrofuran in the presence of a catalytic amount of dimethylformamide.

The phenylalkylsulfonyl chlorides used in the synthesis of Compound 3, the arylalkylamines and arylalkanol derivatives used in the synthesis of Compounds 6a and 6b, compounds of the general formula of Compound 12, the lower alkyl aralkylcarboxylate derivatives used in the synthesis of Compound 16a and the aralkylnitriles used in the preparation of Compound 14b, when not commercially available, can be obtained by conventional synthetic procedures, in accordance with literature precedent, from readily accessible starting materials using standard reagents and reaction conditions.

It will be understood that when A is

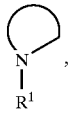

wherein

and $R^1$ are as used herein, the compounds of the invention may contain two groups. Therefore, many of the reactions described above can be performed on both $R^1$ groups simultaneously by adding an additional equivalent of reagent to the appropriate substrate. Furthermore, it is possible to selectively modify one of the $R^1$ groups without modifying the others by employing a suitable protecting group scheme known to one skilled in the art.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

II. Selected Compounds of the Invention

In the preferred embodiment of this invention, the instant compound is selected from the group of compounds shown in Table 1 below.

TABLE 1

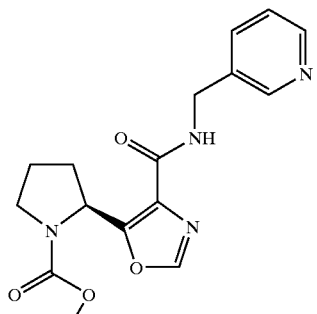

Compound 1

TABLE 1-continued

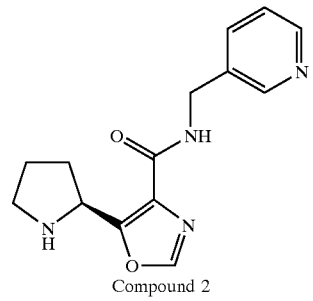

Compound 2

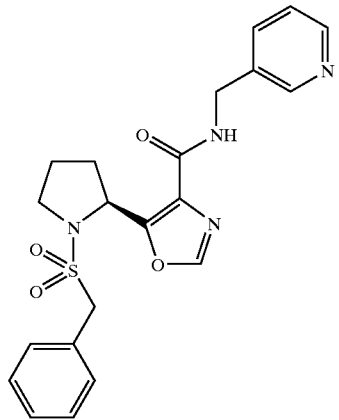

Compound 3

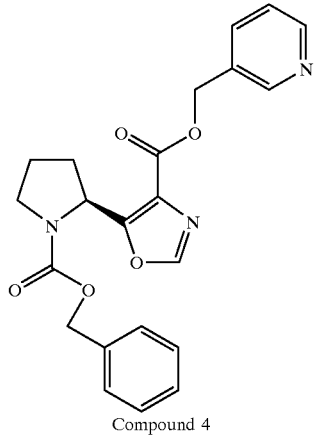

Compound 4

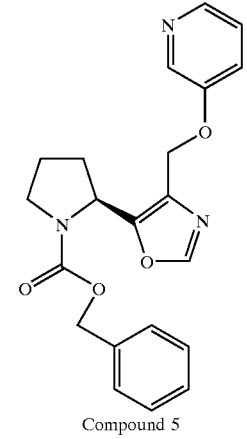

Compound 5

TABLE 1-continued
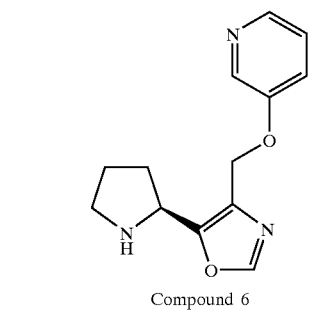
Compound 6
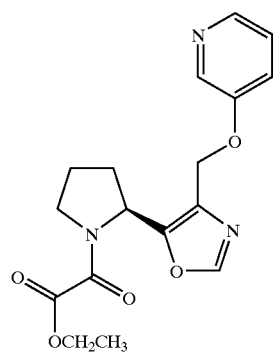
Compound 7
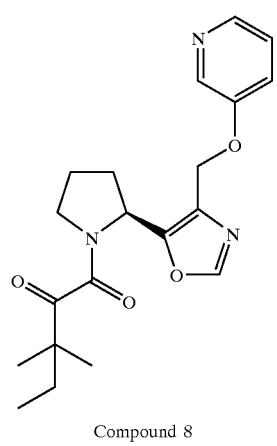
Compound 8
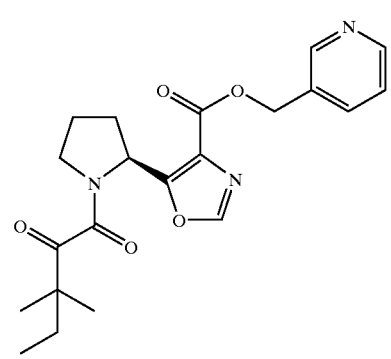
Compound 9
TABLE 1-continued
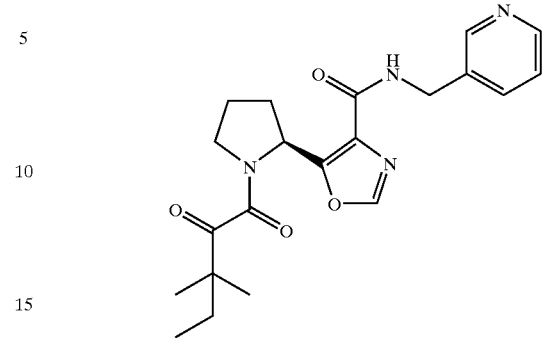
Compound 10
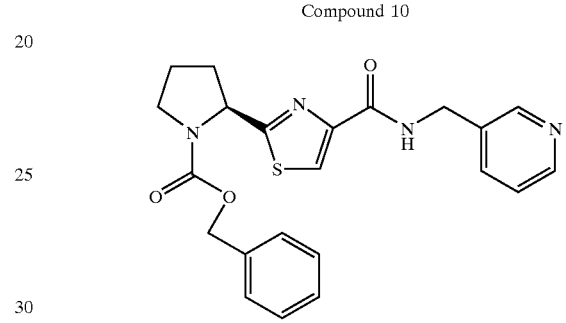
Compound 11
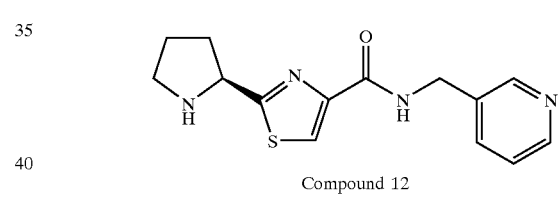
Compound 12
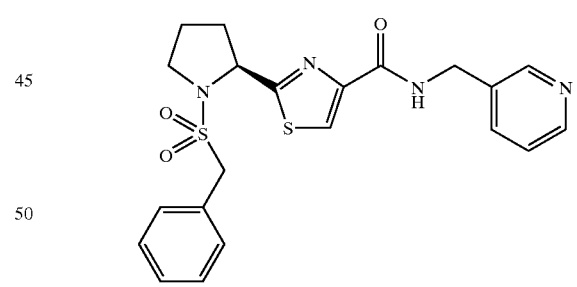
Compound 13
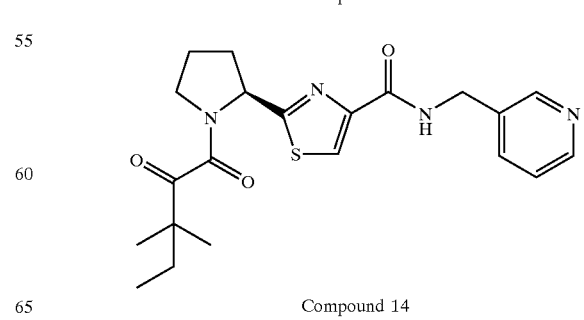
Compound 14

TABLE 1-continued
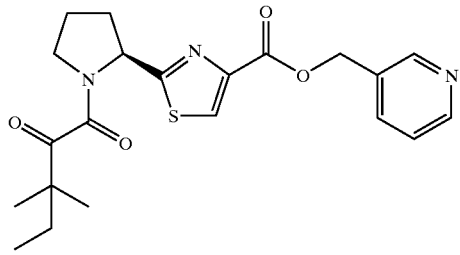
Compound 15
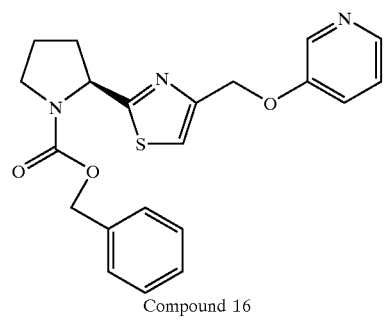
Compound 16
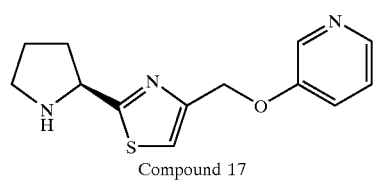
Compound 17
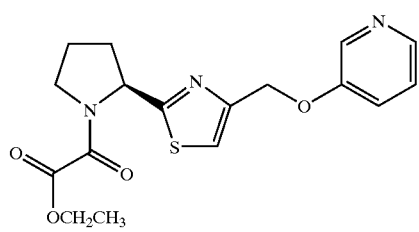
Compound 18
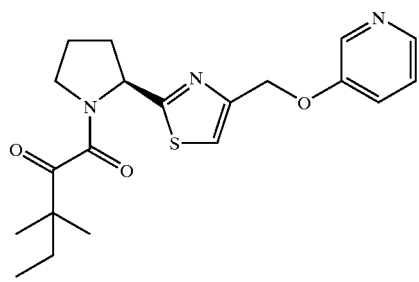
Compound 19
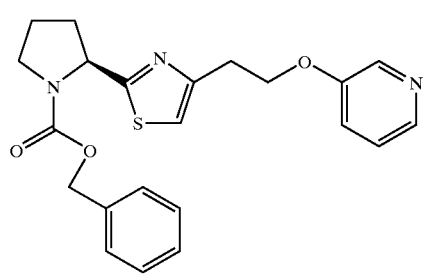
Compound 20
TABLE 1-continued
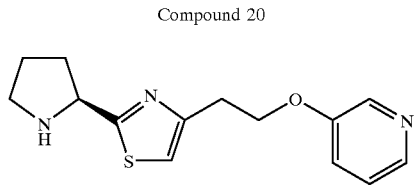
Compound 21
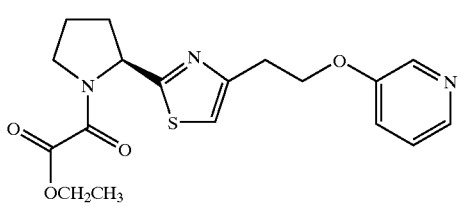
Compound 22
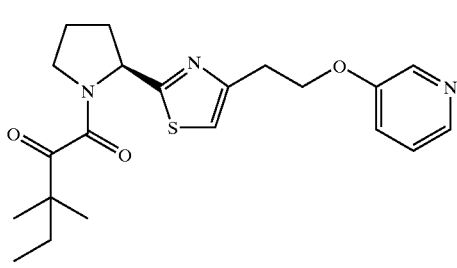
Compound 23
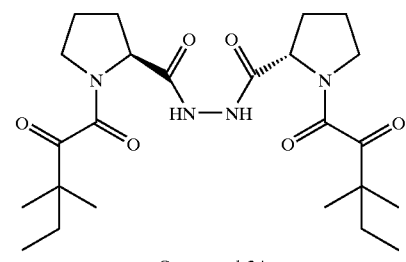
Compound 24
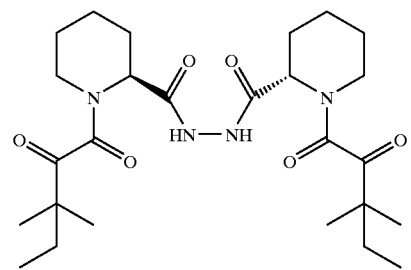
Compound 25
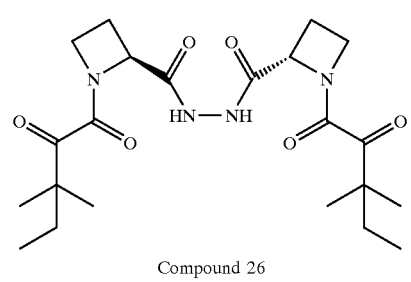
Compound 26

TABLE 1-continued
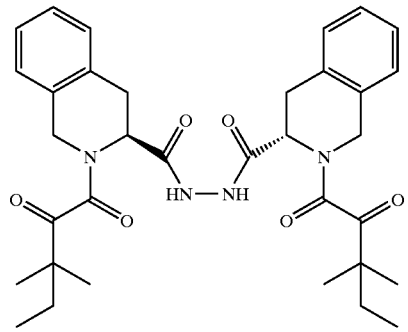
Compound 27
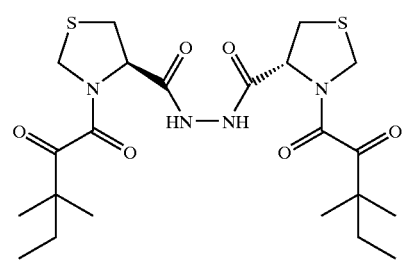
Compound 28
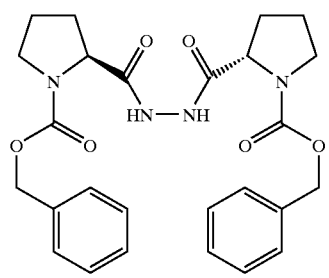
Compound 29
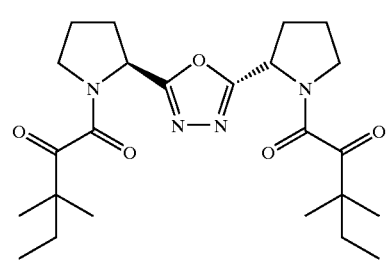
Compound 30
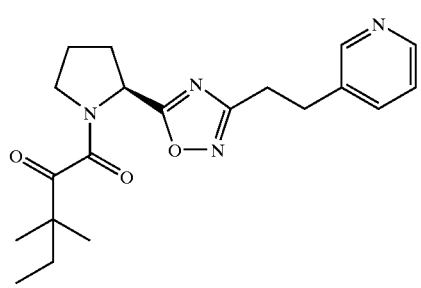
Compound 31
TABLE 1-continued
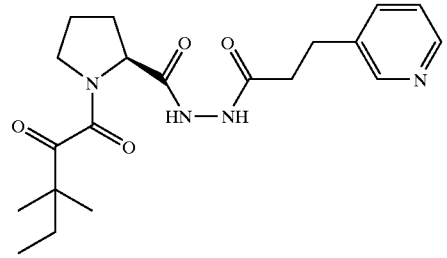
Compound 32
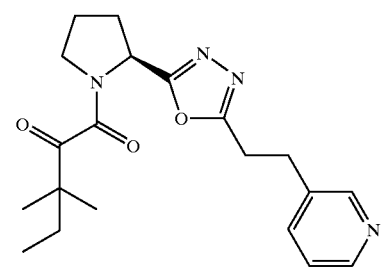
Compound 33
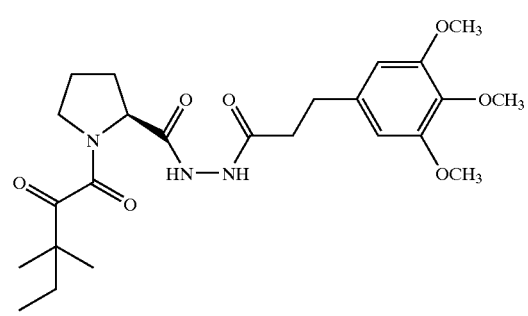
Compound 34
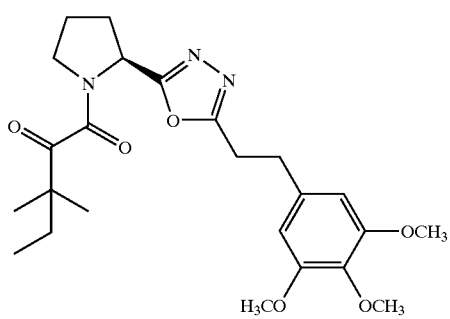
Compound 35
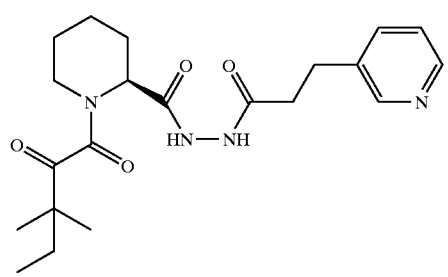
Compound 36

TABLE 1-continued
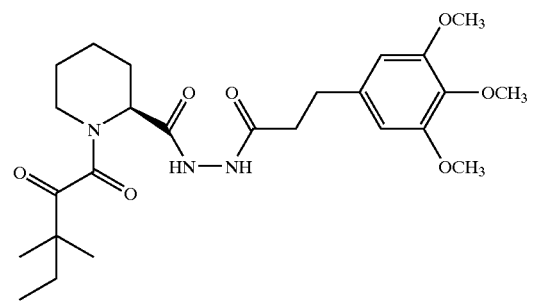
Compound 37
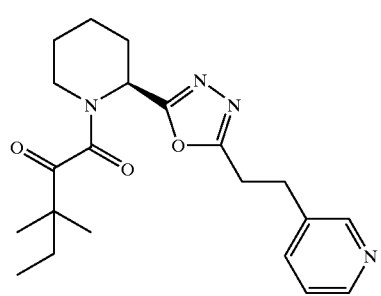
Compound 38
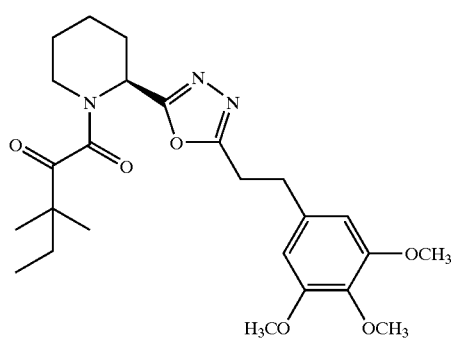
Compound 39
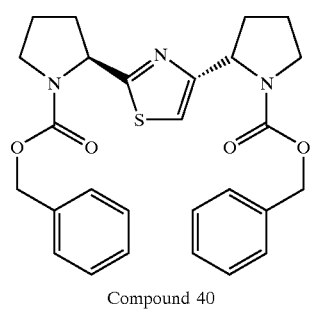
Compound 40
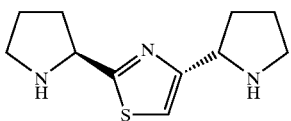
Compound 41
TABLE 1-continued
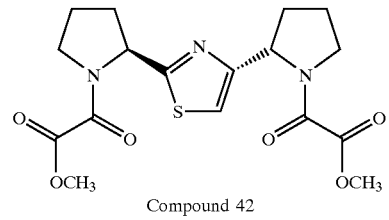
Compound 42
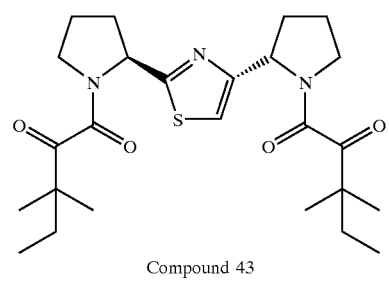
Compound 43
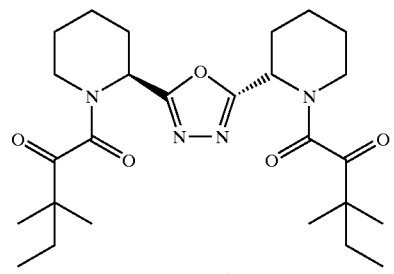
Compound 44
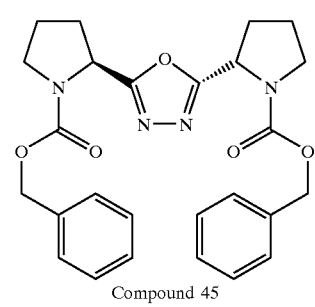
Compound 45
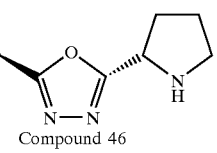
Compound 46
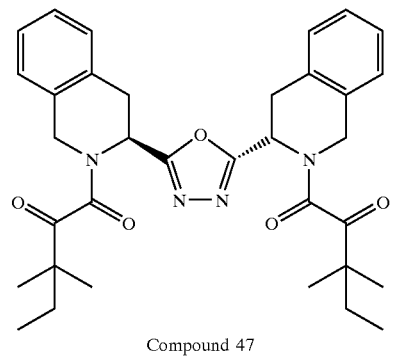
Compound 47

TABLE 1-continued
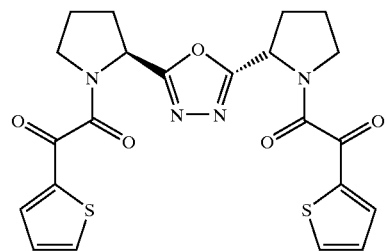
Compound 48
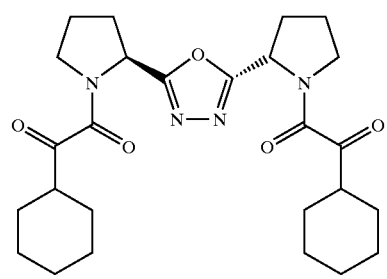
Compound 49
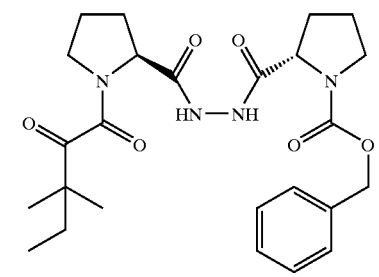
Compound 50
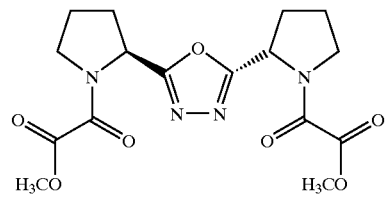
Compound 51
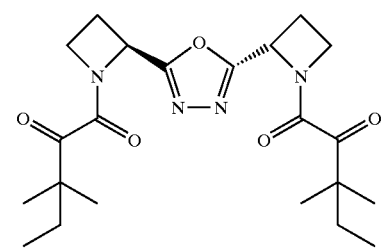
Compound 52
TABLE 1-continued
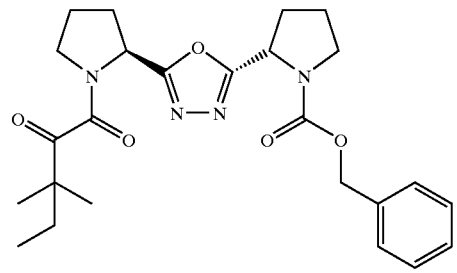
Compound 53
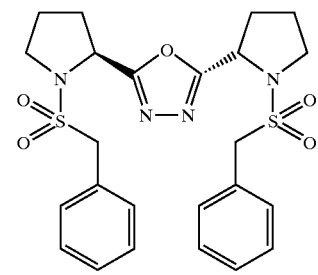
Compound 54
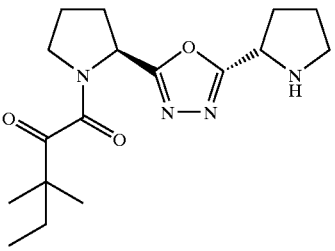
Compound 55
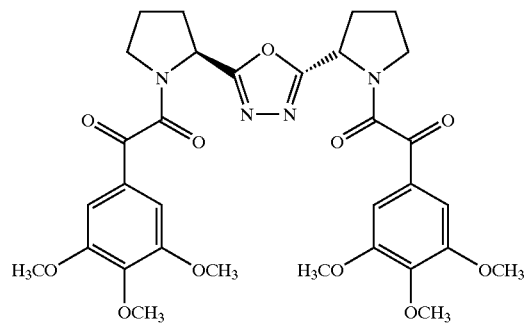
Compound 56
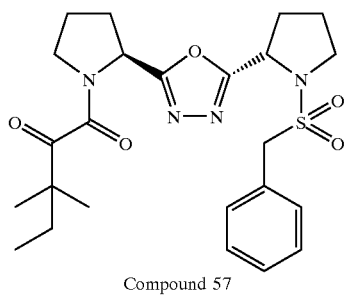
Compound 57

TABLE 1-continued

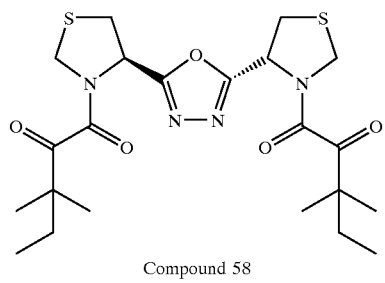

Compound 58

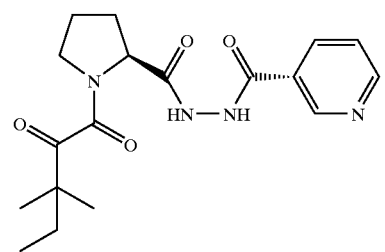

Compound 59

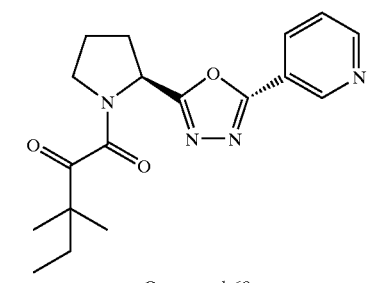

Compound 60

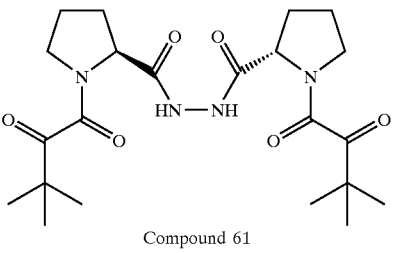

Compound 61

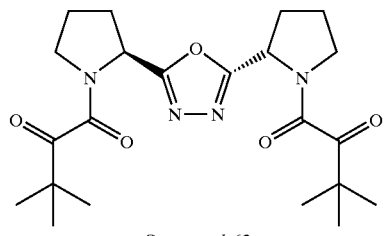

Compound 62

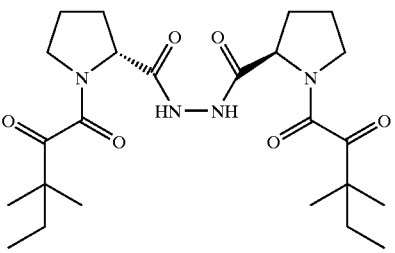

TABLE 1-continued

Compound 63

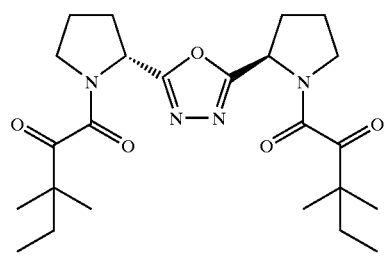

Compound 64

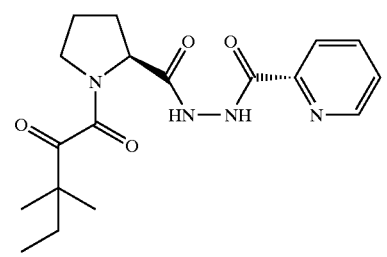

Compound 65

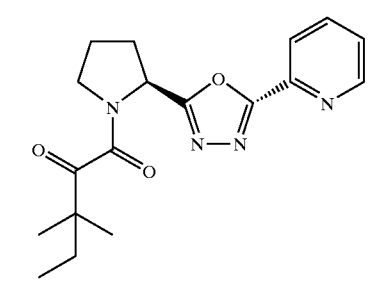

Compound 66

III. Specific Synthetic Methods

Specific compounds which are representative of this invention can be prepared as per the following examples. For the sake of clarity, compounds of the invention produced in the following examples are identified by the term "Compound" followed by the appropriate numeral (e.g., "Compound 1"). Intermediates in the synthesis of compounds of the invention are designated as "Reference Examples." No attempt has been made to optimize the yields obtained in these reactions. One skilled in the art would know how to increase such yields through routine variations in reaction times, temperatures, solvents and/or reagents.

The products of some Reference Examples may be used as intermediates to produce more than one of the instant compounds. In those cases, the choice of intermediates to be used to produce subsequent compounds of the present invention is a matter of discretion that is well within the capabilities of those skilled in the art.

Reference Example 1

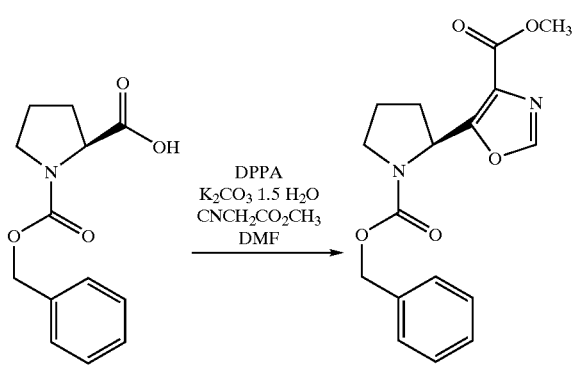

To a cold (0° C.) suspended mixture of N-carbobenzyloxy-L-proline (9.96 g, 40.0 mmol) and potassium carbonate sesquihydrate (26.50 g, 160.0 mmol) in DMF (60 mL) was added diphenylphosphoryl azide (12.0 mL, 55.6 mmol) and methyl isocyanoacetate (7.30 mL, 80.3 mmol). The ice bath was removed and the reaction mixture was stirred at about room temperature (RT) for about 20 h. Brine was added and the reaction mixture was filtered. The filtrate was extracted with $CHCl_3/CH_3OH$ (9:1, 150 mL). The organic solution was washed with $H_2O$ (3×), brine (4×), dried over $Na_2SO_4$, filtered and concentrated to dryness. The crude product was chromatographed on silica gel with 2% $CH_3OH$ in $CHCl_3$ to provide the oxazole (7.47 g, 56% yield) of a light brown oil as 45:55 mixture of rotamers by NMR. CIMS MH$^+$=331 (100%). $^1$H NMR (300 MHz, DMSO-d$_6$) δ1.95–2.00 (m, 3H), 2.30–2.45 (m, 1H), 3.45–3.60 (m, 2H), 3.71 (s, 0.55×3H), 3.82 (s, 1.35H), 4.91 (d, $J_{ab}$=12.82, 1.1H), 5.03 (d, $J_{ab}$=12.82, 0.9H), 5.45–5.48 (m, 0.45H), 5.52–5.54 (m, 0.55H), 7.02 (br s, 1H), 7.26–7.34 (m, 4H), 8.32–8.39 (m, 1H).

Reference Example 2

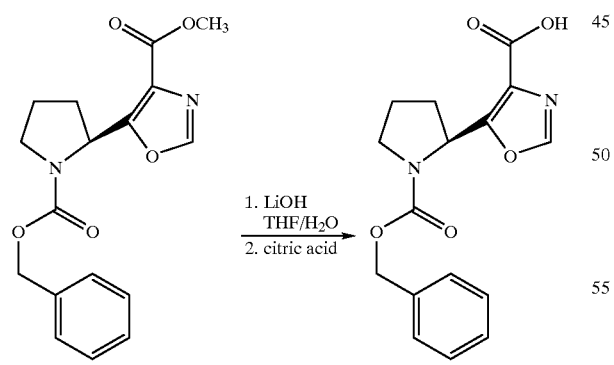

To a cold (0° C.) solution of the methyl ester from Reference Example 1 (7.27 g, 22.6 mmol) in a THF/H$_2$O mixture (2:1, 270 mL) was added lithium hydroxide (594.7 mg, 24.8 mmol). The resultant mixture was stirred at about RT overnight. The reaction mixture was acidified with 4.80 g of citric acid in 100 mL of water and extracted with CHCl$_3$ (2×150 mL). The combined organic extract was dried over Na$_2$SO$_4$, filtered and concentrated to give the carboxylic acid (6.66 g, 93% yield) as a white flaky solid. CIMS M−1=315 M−45=271 (100%). $^1$H NMR (300 MHz, DMSO-d$_6$), a 45:55 mixture of rotamers, δ1.95–2.05 (m, 3H), 2.25–2.40 (m, 1H), 3.35–3.60 (m, 2H), 4.91 (d, $J_{ab}$=12.82, 0.55×2H), 5.03 (d, $J_{ab}$=12.82, 0.45×2H), 5.45–5.48 (m, 0.45×1H), 5.52–5.54 (m, 0.55×1H), 7.00 (br s, 1H), 7.20–7.45 (m, 5H), 8.25–8.35 (m, 1H).

Compound 1

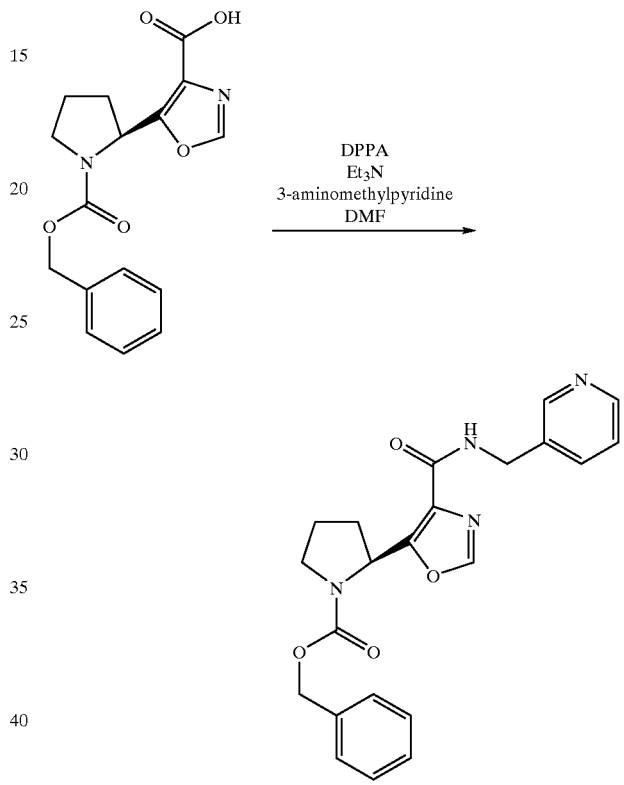

To a cold (0° C.) solution of oxazole-4-carboxylic acid from Reference Example 2 (632.3 mg, 2.00 mmol) and triethylamine (0.62 mL, 4.45 mmol) in DMF (2 mL) was added diphenylphosphorylazide (0.48 mL, 2.22 mmol) and 3-aminomethylpyridine (0.22 mL, 2.16 mmol). The resultant mixture was stirred at about RT for about 1 d, diluted with water (25 mL) and extracted with EtOAc (2×25 mL). The combined organic extract was washed with water (6×50 mL), dried over Na$_2$SO$_4$, filtered and concentrated to dryness. The crude product was chromatographed on silica gel with 100% EtOAc to give Compound 1 (0.49 g, 60% yield) as a colorless immobile oil. MS (loop pos) MH$^+$=407 (100%); M+Na=429 (10%). $^1$H NMR (300 MHz, CDCl$_3$), a 45:55 mixture of rotamers, δ1.90–2.15 (m, 3H), 2.30–2.45 (m, 1H), 3.55–3.70 (m, 2H), 4.45–4.65 (m, 2H), 4.85–5.20 (m, 2H), 5.65–5.70 (m, 0.45×1H), 5.75–5.80 (m, 0.55×1H), 7.0 (br s, 1H), 7.20–7.40 (m, 6H), 8.45–8.50 (m, 1H), 8.55–8.60 (m, 1H).

Compound 2

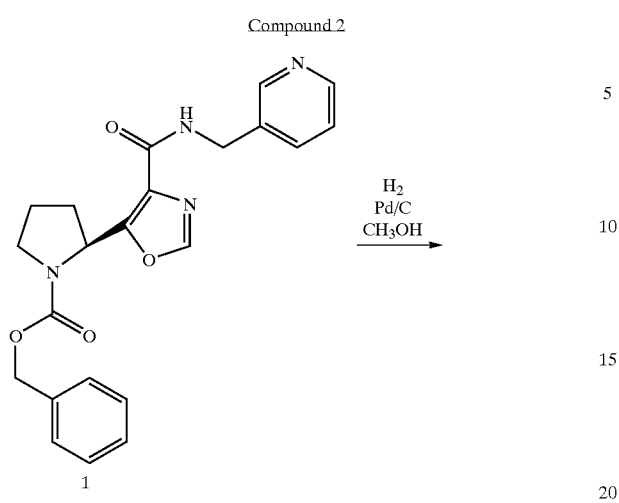

1

A heterogeneous mixture of Compound 1 (0.39 g, 0.96 mmol) and 10% palladium on carbon (0.05 g) in CH$_3$OH (25 mL) was shaken under 50 psi of hydrogen gas at about RT for about 3 h. The mixture was filtered through a bed of Celite and the filter cake was rinsed with CH$_3$OH. The combined filtrate was concentrated in vacuo to afford Compound 2 (0.25 g, 96% yield) as an immobile oil which was carried on without further purification. MS (loop pos) MH$^+$= 273 (100%). $^1$H NMR (300 MHz, CDCl$_3$), δ1.8–2.2 (m, 4H), 2.95–3.05 (m, 1H), 3.10–3.20 (m, 1H), 4.55–4.70 (m, 2H), 4.90 (t, J=7.00 Hz, 1H), 7.20–7.35 (m, 2H), 7.60–7.75 (m, 3H), 8.53 (d, J=4.13 Hz, 1H), 8.62 (s, 1H).

Compound 3

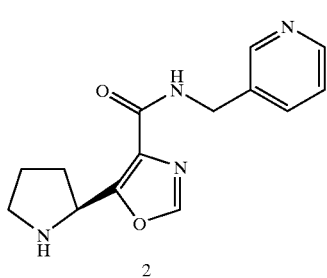

2

BzlSO$_2$Cl
Et$_3$N
CH$_2$Cl$_2$

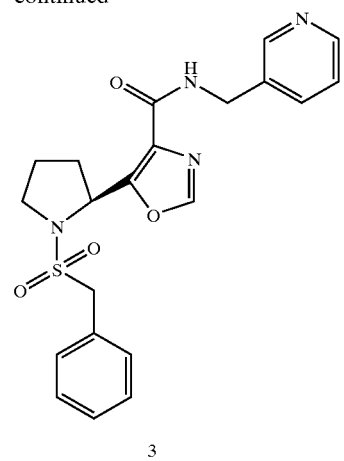

3

To a cold (0° C.) solution of Compound 2 (0.25 g, 0.91 mmol) and triethylamine (140 mL, 1.00 mmol) in methylene chloride (10 mL) was added α-toluenesulfonyl chloride (184.2 mg, 0.966 mmol). After stirring for about 6 h at about RT, the reaction mixture was treated with 35.6 mg of the sulfonyl chloride and 30 mL of triethylamine. The reaction mixture was diluted with methylene chloride (40 mL), washed with water (2×50 mL), dried over sodium sulfate, filtered and concentrated to dryness. The crude product was chromatographed by preparative TLC with 100% EtOAc to provide Compound 3 (0.17 g, 44% yield) as a taffy solid. MS (loop pos) MH$^+$=427 (100%). $^1$H NMR (300 MHz, CDCl$_3$) δ1.72–1.80 (m, 1H), 1.95–2.11 (m, 2H), 2.27–2.36 (m, 1H), 3.07–3.15 (m, 1H), 3.44–3.52 (m, 1H), 4.27 (d, J$_{ab}$=13.97 Hz, 1H), 4.41 (d, J$_{ab}$=13.96 Hz, 1H), 4.44–4.71 (m, 3H), 5.72–5.77 (m, 1H), 7.28–7.45 (m, 6H), 7.69–7.72 (m, 2H), 8.53 (d, J=4.13 Hz, 1H), 8.62 (s, 1H).

Compound 4

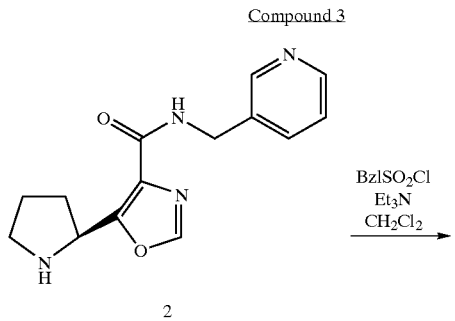

DMAP
Et$_3$N
3-pyridylcarbinol
isoprenylchloroformate
THF

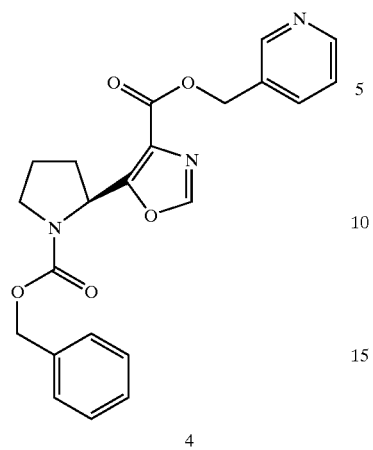

4

To a cold (0° C.) solution of oxazole-4-carboxylic acid from Reference Example 2 (1.26 g, 4.00 mmol), triethylamine (0.62 mL, 4.445 mmol), DMAP (49.5 mg, 0.405 mmol) and 3-pyridylcarbinol (0.39 mL, 4.02 mmol) in THF (20 mL) was added isopropenyl chloroformate (0.48 mL, 4.39 mmol). Upon warming to about RT, the dark yellow, heterogeneous reaction mixture was stirred at about RT for about 20 h. The reaction was diluted with EtOAc, washed with water, and extracted with 1 N aqueous HCl. The acidic aqueous solution was basified with aqueous $Na_2CO_3$ and extracted with $CHCl_3$ (2×100 mL). The $CHCl_3$ solution was dried over $Na_2SO_4$, filtered and concentrated to dryness. The crude product was chromatographed on silica gel with 100% EtOAc to afford Compound 4 (0.61 g, 37% yield) as a colorless immobile oil. MS (loop pos) MH$^+$=408 (100%). $^1$H NMR (300 MHz, CDCl$_3$) δ1.98–2.10 (m, 3H), 2.25–2.45 (m, 1H), 3.50–3.70 (m, 2H), 4.86–5.39 (m, 4H), 5.59–5.61 (m, 1H), 5.65–5.85 (m, 1H), 7.05 (br s, 1H), 7.30–7.35 (m, 5H), 7.66–7.80 (m, 2H), 8.58–8.71 (m, 2H).

Reference Example 3

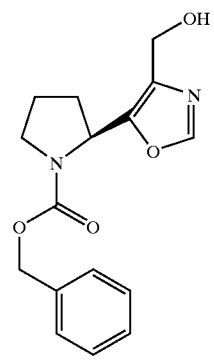

To a solution of the methyl ester from Reference Example 1 (3.66 g 11.0 mmol) and lithium chloride (2.50 g, 58.9 mmol) in EtOH/THF mixture (4:3; 175 mL) was added sodium borohydride (2.10 g, 55.0 mmol) in two equal portions. The resultant heterogeneous mixture was stirred for about 3 d at about RT. The reaction mixture was quenched with aqueous NH$_4$Cl solution (200 mL) and extracted with CHCl$_3$ (3×150 mL). The organic solution was dried over Na$_2$SO$_4$, filtered and concentrated to dryness. The crude product was chromatographed on silica gel with 3% CH$_3$OH in CHCl$_3$ to afford the alcohol (2.87 g, 86% yield) as a colorless oil. MS (loop pos) MH$^+$=303 (100%); $^1$H NMR (300 MHz, CDCl$_3$) δ1.90–2.10 (m, 1H), 2.15–2.40 (m, 3H), 3.45–3.70 (m, 2H), 4.40–4.50 (m, 1H), 4.60–4.80 (m, 2H), 4.90–5.15 (m, 2H), 5.20–5.30 (m, 1H), 7.30–7.35 (m, 5H), 7.35 (s, 5H), 7.75 (s, 1H).

Compound 5

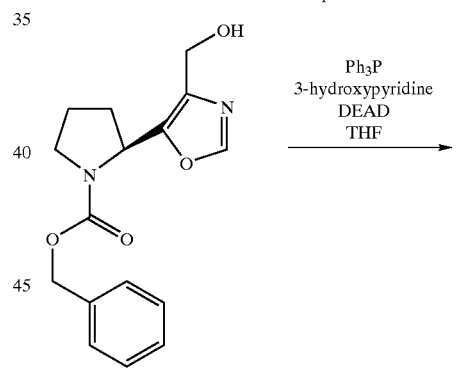

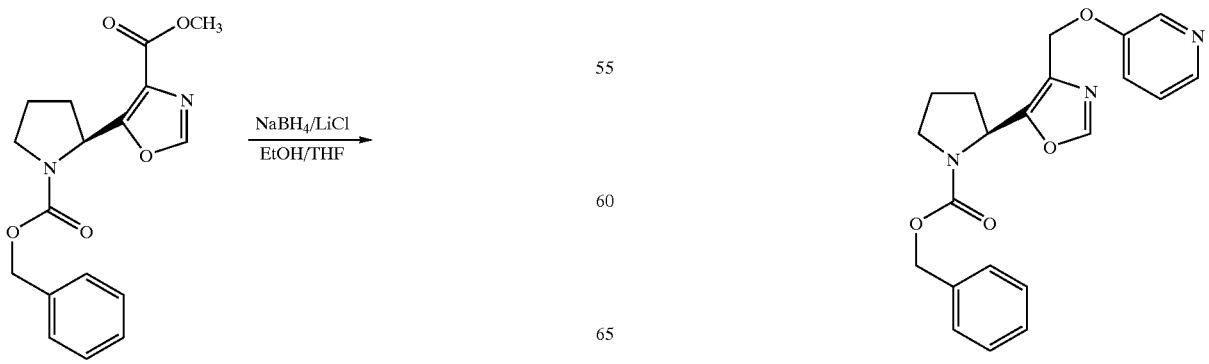

5

To a cold (0° C.) solution of the oxazole-4-methanol from Reference Example 3 (2.34 g, 7.74 mmol), triphenylphosphine (3.05 g, 11.6 mmol), and 3-hydroxypyidine (1.11 g, 11.7 mmol) in THF (60 mL) was added DEAD (1.86 mL, 11.7 mmol). The resultant mixture was stirred overnight at about RT and concentrated to dryness. The oil was chromatographed on silica gel with 3% $CH_3OH$ in $CHCl_3$ to give crude Compound 5 which contained byproducts. The oil was dissolved in $CH_2Cl_2$ (50 mL) and washed with 1 N aqueous HCl (5×80 mL). The acidic aqueous solution was basified with $NaHCO_3/Na_2CO_3$ and extracted into $CHCl_3$ (3×50 mL). The $CHCl_3$ solution was dried over $Na_2SO_4$, filtered and concentrated to provide Compound 5 (0.47 g) as an oil which solidified upon standing. The compound was used as such without further purification. MS (loop pos) $MH^+$=380 (100%). $^1H$ NMR (300 MHz, $CDCl_3$) 1:1 mixture of rotamers, δ1.90–2.10 (m, 2H), 2.15–2.30 (m, 2H), 3.45–3.65 (m, 2H), 4.40–4.60 (m, 1H), 4.95–5.30 (m, 4H), 7.10–7.25 (m, 2H), 7.30 (s, 5H), 7.75–8.00 (m, 1H), 8.15 (br s, 0.5×1H), 8.25–8.30 (m, 1H), 8.40 (br s, 0.5×1H).

Compounds 6, 7, and 8

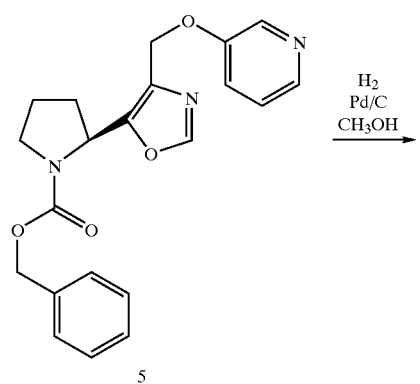

5

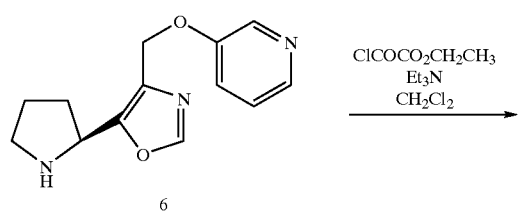

6

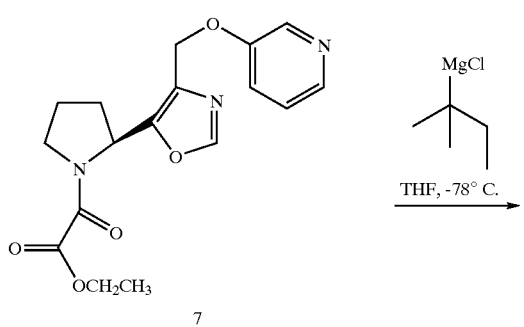

7

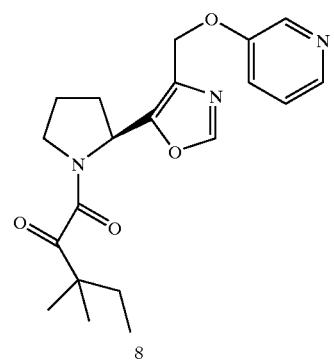

8

A heterogeneous mixture of the crude Compound 5 (0.43 g) and 10% palladium on carbon, (0.05 g) in $CH_3OH$ (35 mL) was shaken under about 54 psi of hydrogen gas for about 6.5 h at about RT. The mixture was filtered through a bed of Celite; the filter cake was rinsed with $CH_3OH$. The filtrate was concentrated in vacuo to provide a residue. The crude product was chromatographed on silica gel with $CHCl_3:CH_3OH:NH_4OH$ (90:9:1) to give Compound 6 (0.10 g) as an oil. MS (loop pos) $MH^+$=246 (100%).

To a cold (0° C.) solution of Compound 6 (0.10 g, 0.41 mmol), and triethylamine (70 mL, 0.50 mmol) in $CH_2Cl_2$ (10 mL) was added ethyl oxalyl chloride (70 mL, 0.63 mmol). The reaction mixture was stirred for about 2 h, diluted with additional $CH_2Cl_2$ (50 mL), washed with aqueous NaCl (3×50 mL), dried over $Na_2SO_4$ filtered and concentrated to provide Compound 7 (0.10 g, 71% yield) as an oil which was carried on to the next step without further purification. MS (loop pos) $MH^+$=346 (100%).

To a cold (−78° C.) solution of Compound 7 (0.10 g, 0.29 mmol) in THF (10 mL) was added excess 1,1-dimethylpropylmagnesium chloride (1M, 1.40 mL) in $Et_2O$ and the resultant mixture was stirred for about 2 h at about −78° C. The reaction mixture was quenched with aqueous $NH_4Cl$ (25 mL) and extracted with EtOAc (2×50 mL). The EtOAc solution was dried over $Na_2SO_4$, filtered and concentrated to dryness. The crude product was chromatographed on silica gel with 1:1 EtOAc:hexane to give Compound 8 (55.5 mg, 52% yield) as an oil. MS (loop pos) $MH^+$=372 (100%). $^1H$ NMR (300 MHz, DMSO-$d_6$), a mixture of rotamers (3 to 1), δ0.66 (t, J=7 Hz, 0.25×3H), 0.75 (t, J=7 Hz, 0.75×3H), 0.80 (s, 0.25×3H), 0.88 (s, 0.25×3H), 1.07 (s, 0.75×3H), 1.10 (s, 0.75×3H), 1.56–1.59 (m, 2H), 1.88–1.98 (m, 2H), 2.08–2.29 (m, 2H), 3.42–3.60 (m, 2H), 4.93 (d, J=12 Hz, 0.25×1H), 4.99 (d, J=12 Hz, 0.25×1H), 5.08 (d, J=12 Hz, 0.75×1H), 5.18 (d, J=12 Hz, 0.75×1H), 5.34–5.38 (m, 1H), 7.47–7.54 (m, 1H), 7.32–7.39 (m, 1H), 8.18–8.20 (m, 1H), 8.34–8.35 (m, 1H) 8.35 (s, 0.75×1H), 8.41 (s, 0.25×1H).

Reference Example 4

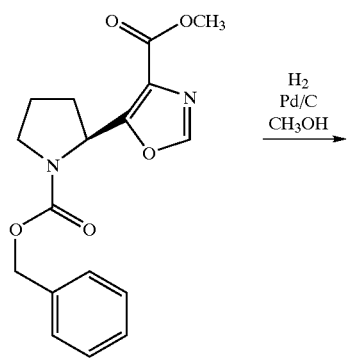

A heterogeneous mixture of the methyl ester from Reference Example 1 (2.00 g, 6.00 mmol), and 10% palladium on carbon (0.20 g) in CH$_3$OH (40 mL) was shaken under 54 psi of hydrogen gas at about RT for about 20 h. The mixture was filtered through a bed of Celite and the filter cake was rinsed with additional CH$_3$OH (75 mL). The combined filtrate was concentrated to yield the pyrrolidine (1.20 g, 100% yield) as a yellow solid. MS (loop pos) MH$^+$=197 (100%). $^1$H NMR (300 MHz, CDCl$_3$), δ2.10–2.25 (m, 3H), 2.40–2.50 (m, 1H), 3.40–3.60 (m, 2H), 3.95 (s, 3H), 5.40–5.50 (m, 1H), 7.95 (s, 1H).

Reference Example 5

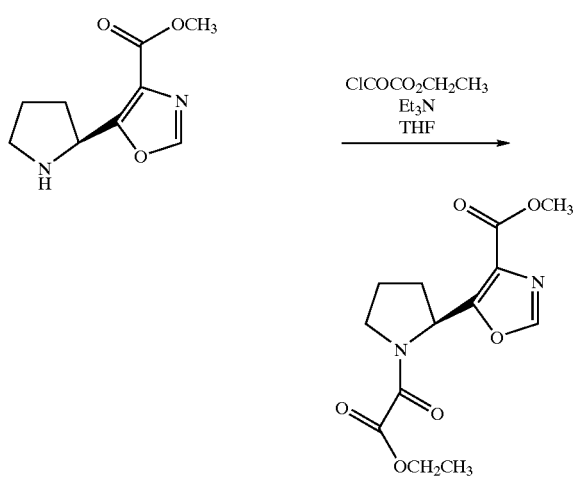

To a cold (0° C.) mixture of the pyrrolidine from Reference Example 4 (1.18 g, 6.00 mmol) and triethylamine (0.94 mL, 6.74 mmol) in CH$_2$Cl$_2$ (100 mL), was added ethyl oxalyl chloride (0.80 mL, 8.70 mmol) in CH$_2$Cl$_2$ (25 mL). The resultant reaction was stirred at about RT for about 2 h, washed with aqueous NaCl solution (3×75 mL) and dried over Na$_2$SO$_4$. The CH$_2$Cl$_2$ was filtered and concentrated to a residue which was purified by chromatography (elution with 35% hexane in EtOAc) to give the oxamate (1.23 g, 72% yield) as an oil which solidified. MS (loop pos) MH$^+$=283 (5%). $^1$H NMR (300 MHz, CDCl$_3$), a 1:1.5 mixture of rotamers, δ1.35 (t, J=7 Hz, 0.6×3H), 1.20 (t, J=7 Hz, 0.4×3H), 1.95–2.20 (m, 3H), 2.40–2.50 (m, 1H), 3.40–3.60 (m, 2H), 3.89 (s, 0.6×3H), 3.91 (s, 0.4×3H), 4.00–4.15 (m, 0.4×2H), 4.29–4.40 (m, 0.6×2H), 5.70–5,75 (m, 0.6×1H), 5.90–5.95 (m, 0.4×1H), 7.75 (s, 0.6×1H), 7.80 (s, 0.4×1H).

Reference Example 6

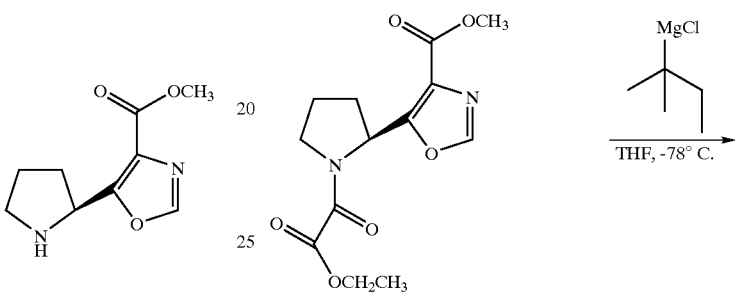

To a cold (−78° C.) solution of oxamate from Reference Example 5 (0.87 g, 3.08 mmol) in anhydrous THF (10 mL) was added excess 1,1-dimethylpropylmagnesium chloride (1M, 4.60 mL, 4.60 mmol) in Et$_2$O and the resultant mixture was stirred for about 3 h at about −78° C. The reaction mixture was quenched with aqueous NH$_4$Cl (25 mL) and extracted with EtOAc (2×25 mL). The EtOAc solution was dried over Na$_2$SO$_4$, filtered and concentrated to dryness. The reaction was repeated with 284.5 mg of oxamate and 1.50 mL of dimethylpropylmagnesium chloride. The combined crude product was chromatographed on silica gel with 1:1 EtOAc:hexane to give the oxamide (0.95 g, 96% yield) as a colorless oil. MS (loop pos) MH$^+$=323 (90%). $^1$H NMR (300 MHz, CDCl$_3$), a mixture of rotamers (3 to 1), δ0.70 (t, J=7.4 Hz, 0.25×3H), 0.80 (t, J=7.4 Hz, 0.75×3H), 1.00 (s, 0.25× 3H), 1.05 (s, 0.25×3H), 1.15 (s, 0.75×6H), 1.65–1.75 (m, 2H), 1.90–2.20 (m, 0.75×2H), 2.35–2.50 (m, 0.25×2H), 3.55–3.70 (m, 0.75×1H), 3.75–3.80 (m, 0.25×1H), 3.90 (s, 1H), 5.70–5.80 (m, 1H), 7.75 (s, 0.75×1H), 7.80 (s, 0.25× 1H).

Reference Example 7

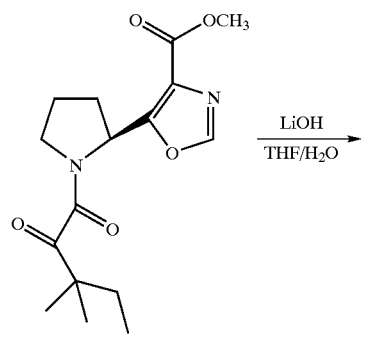

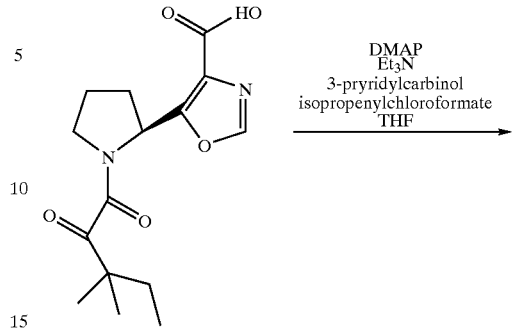

Compound 9

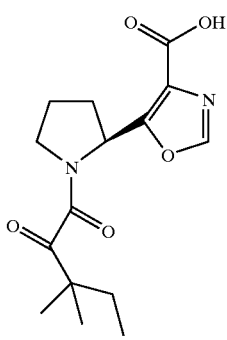

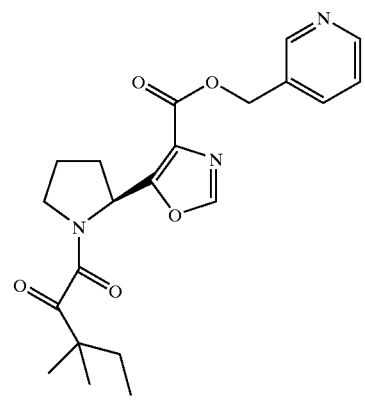

9

A solution of the 4-carbomethoxyoxazole from Reference Example 6 (0.93 g, 2.88 mmol) and lithium hydroxide (76.9 mg, 3.21 mmol) in a THF/H$_2$O mixture (2:1; 30 mL) was stirred at about 0° C. for about 1 h and at about RT for about 22 h. The reaction mixture was washed with Et$_2$O (2×75 mL), acidified with aqueous citric acid (pH=1.0) and extracted with CHCl$_3$ (3×50 mL). The CHCl$_3$ solution was dried over Na$_2$SO$_4$, filtered and concentrated to an oil. This oil was covered with Et$_2$O and placed under high vacuum to afford the carboxylic acid (0.80 g, 90% yield) as a white solid. MS (loop neg) M−1=307 (100%). $^1$H NMR (300 MHz, THF-d$_8$), a mixture of rotamers (2.5 to 1), δ0.70 (t, J=7.4 Hz, 0.30×3H), 0.85 (t, J=7.4 Hz, 0.70×3H), 0.92 (s, 0.30×3H), 0.95 (s, 0.30×3H), 1.15 (s, 0.70×6H), 1.45–1.65 (m, 2H), 1.90–2.20 (m, 3H), 2.30–2.40 (m, 1H), 3.50–3.65 (m, 2H), 5.65–5.73 (m, 0.7×1H), 5.75–5.80 (m, 0.3×1H), 7.9 (s, 0.7×1H), 8.00 (s, 0.3×1H).

To a cold (0° C.) solution of the oxazole-4-carboxylic acid from Reference Example 7 (0.31 g, 1.00 mmol), triethylamine (0.17 mL, 1.22 mmol), DMAP (12.1 mg, 0.099 mmol) and 3-pyridylcarbinol (0.11 mL, 1.13 mmol) in THF (15 mL) was added isopropenyl chloroformate (0.12 mL, 1.10 mmol). Upon warming to about RT, the dark yellow, heterogeneous reaction mixture was stirred at about RT for about 20 h. The reaction was diluted with water and extracted into CHCl$_3$ (2×50 mL). The CHCl$_3$ solution was dried over Na$_2$SO$_4$, filtered and concentrated to dryness. The crude product was chromatographed on silica gel with 3% CH$_3$OH in CHCl$_3$ to afford Compound 9 (222.8 mg, 56% yield) as a light yellow immobile oil. MS (loop pos) MH$^+$= 400 (100%). $^1$H NMR (300 MHz, DMSO-d$_6$), a mixture of rotamers (3 to 1), δ0.62 (t, J=7.4 Hz, 0.25×3H), 0.76 (t, J=7.4 Hz, 0.75×3H), 0.83 (s, 0.25×3H), 0.86 (s, 0.25×3H), 1.11 (s, 0.75×6H), 1.44–1.49 (m, 0.25×2H), 1.58 (q, J=7.41, 7.42, 7.41 Hz, 0.75×2H), 1.88–2.04 (m, 3H), 2.25–2.34 (m, 1H), 3.34–3.61 (m, 2H), 5.31–5.39 (m, 2H), 5.52–5.59 (m, 1H), 7.42–7.46 (m, 1H), 7.89–7.91(m, 1H), 8.44 (s, 0.75×1H), 8.50 (s, 0.25×1H), 8.57 (d, J=4.56 Hz, 1H), 8.69 (s, 1H).

Compound 10

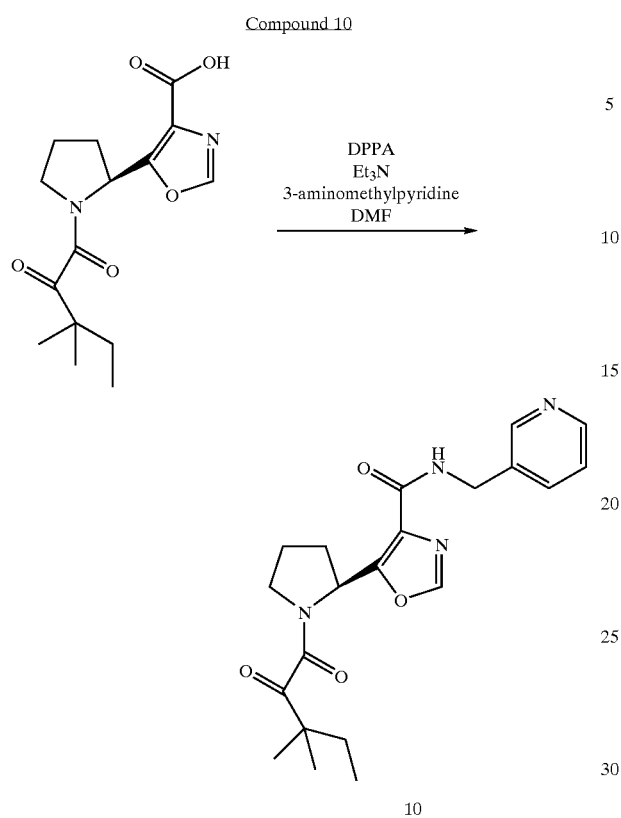

10

To a cold (0° C.) solution of the oxazole-4-carboxylic acid from Reference Example 7 (308.2 mg, 1.00 mmol) and triethylamine (310 mL, 2.22 mmol) in DMF (2 mL) was added diphenylphosphorylazide (480 mL, 1.16 mmol) and 3-aminomethylpyridine (110 mL, 2.16 mmol). The resultant mixture was stirred at about RT for about 1 d, diluted with water (25 mL) and extracted with EtOAc (2×50 mL). The EtOAc solution was dried over $Na_2SO_4$, filtered and concentrated. The crude product was chromatographed on silica gel (elution with 5% $CH_3OH$ in $CHCl_3$) to give Compound 10 (310 mg, 78% yield) as an oil. MS (loop pos) $MH^+$=399 (100%). $^1H$ NMR (300 MHz, DMSO-$d_6$), a mixture of rotamers (2 to 1), δ0.65 (t, J=7.4 Hz, 0.33×3H), 0.75 (t, J=7.4 Hz, 0.67×3H), 0.85 (s, 0.33×3H), 0.90 (s, 0.33×3H), 1.15 (s, 0.67×6H), 1.45–1.65 (m, 2H), 1.80–2.00 (m, 3H), 2.25–2.40 (m, 1H), 3.40–3.60 (m, 2H), 4.35–4.50 (m, 2H), 5.60–5.65 (m, 0.67×1H), 5.70–5.75 (m, 0.33×1H), 7.20–7.30 (m, 2H), 7.55–7.75 (m, 1H), 8.50–8.65 (m, 2H), 8.90–9.00 (m, 1H).

Reference Example 8

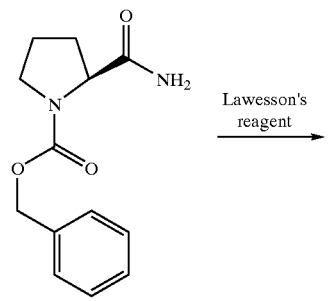

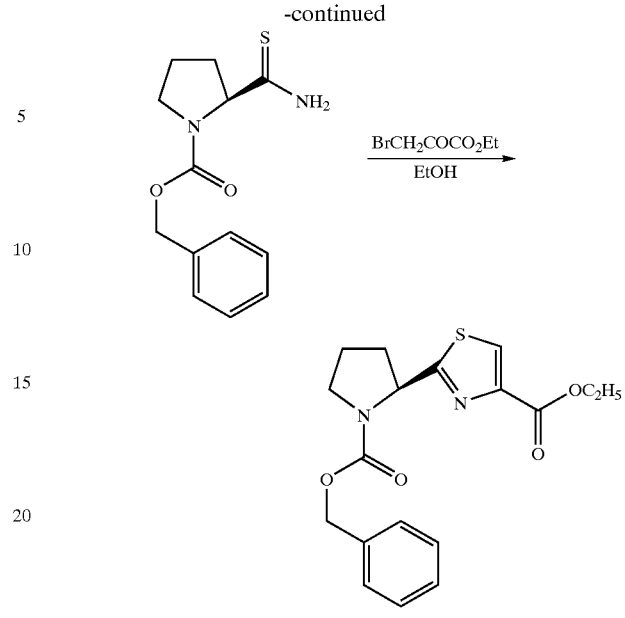

A heterogeneous mixture of the N-CBz-L-prolinamide (1.12 g, 4.51 mmol) and 2,4-bis(4-methoxyphenyl)-1,3-dithia-2,4-diphosphetane-2,4-disulfide (Lawesson's reagent; 911.3 mg, 2.25 mmol) in benzene (20 mL) was stirred at reflux for about 1 h. Then an additional 933.0 mg of Lawesson's reagent was added and the reaction continued to reflux for about an additional hour. The reaction mixture was concentrated to yield the crude thioamide. The residue was dissolved with EtOH (10 mL), treated with ethyl bromopyruvate (300 uL, 1.00 mmol) and stirred at reflux overnight. Upon cooling to RT, the reaction mixture was treated with solid $K_2CO_3$, stirred for about 10 min and concentrated. The residue was dissolved with $CHCl_3$ (50 mL), washed with $H_2O$ (2×), dried over $Na_2SO_4$, filtered and concentrated. The crude product was chromatographed on silica gel with 2% $CH_3OH$ in $CHCl_3$ to provide the thiazole (0.63 g, 39% yield) as a light yellow oil. MS (loop pos) $MH^+$=361 (50%), M+Na=383 (100%). $^1H$ NMR (300 MHz, DMSO-$d_6$), a mixture of rotamers, δ1.23 (t, J=7.32, 7.66, 3H), 1.93–2.37 (m, 3H), 3.50–3.59 (m, 2H), 4.30 (q, J=7.04, 7.05, 7.08 Hz, 2H), 4.94–5.22 (m, 3H), 7.08–7.38 (m, 5H), 8.32 (s, 0.33 H), 8.41 (s, 0.67 H).

Reference Example 9

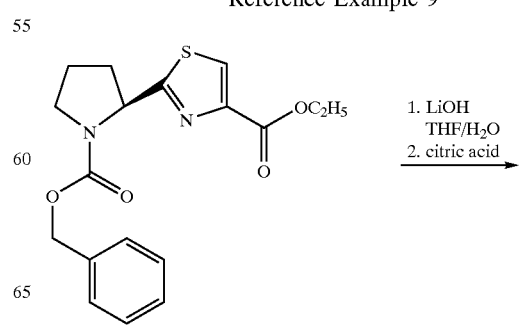

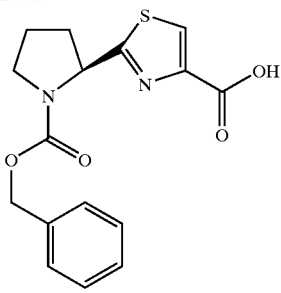

A solution of the ethyl ester from Reference Example 8 (0.55 g, 1.53 mmol) and lithium hydroxide (37.5 mg, 1.56 mmol) in a THF/H$_2$O mixture (2:1; 6 mL) was stirred at about 0° C. for about 1 h and at about RT for about 2 h. The reaction mixture was diluted with aqueous NaCl solution, washed with CHCl$_3$ (2×15 mL), acidified with citric acid (427 mg) then extracted with CHCl$_3$ (2×20 mL). The CHCl$_3$ solution was dried over Na$_2$SO$_4$, filtered and concentrated to yield the carboxylic acid (0.51 g, 100% yield) as an oil which was used without further purification. MS (loop neg) M−1=331 (50%). $^1$H NMR (300 MHz, DMSO-d$_6$), δ1.93–2.35 (m, 3H), 2.25–2.40 (m, 1H), 3.39–3.50 (m, 2H), 4.94–5.21 (m, 3H), 4.94–5.22 (m, 3H), 7.04–7.12 (m, 1H), 7.25–7.37 (m, 4H), 8.33 (s, 1H), 13.0 (br s, 1H).

Coumpound 11

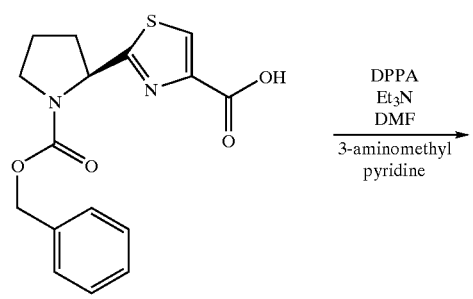

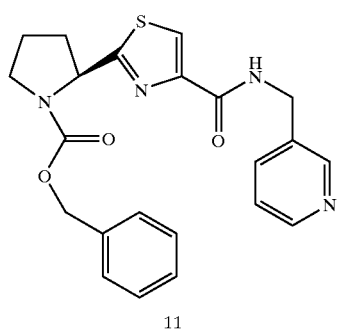

11

To a cold solution of the thiazole-4-carboxylic acid from Reference Example 9 (0.51 g, 1.53 mmol) and triethylamine (0.48 mL, 3.44 mmol) in DMF (3 mL) was added diphenylphosphorylazide (376 mL, 1.72 mmol) and 3-aminomethylpyridine (180 mL, 1.77 mmol). The resultant mixture was stirred at about RT for about 1 d, diluted with water (25 mL) and extracted with EtOAc (2×25 mL). The EtOAc solution was washed with water (6×50 mL), dried over Na$_2$SO$_4$, filtered and concentrated. The crude product was chromatographed on silica gel with 100% EtOAc to give Compound 11 (0.44 g, 68% yield) as a colorless immobile oil. MS (loop pos) MH$^+$=423 (100%) M+Na=445 (10%). $^1$H NMR (300 MHz, CDCl$_3$) δ1.90–2.05 (m, 2H), 2.15–2.45 (m, 2H), 3.45–3.70 (m, 2H), 4.60–4.65 (m, 2H), 4.95–5.25 (m, 3H), 5.65–5.85 (m, 1H), 7.05 (br s, 1H), 7.20–7.40 (m, 5H), 7.66–7.70 (m, 1H), 7.55–7.65 (m, 1H), 8.00–8.05 (m, 1H), 8.50–8.65 (m, 2H).

Compound 12

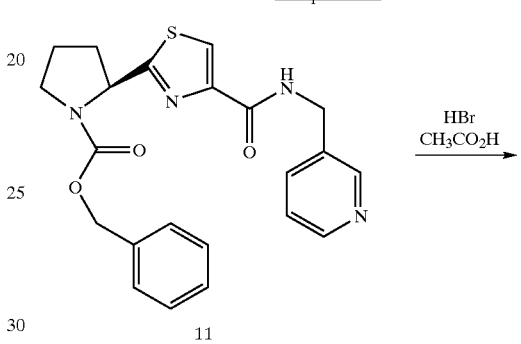

11

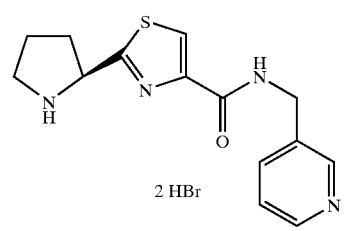

12

A mixture of Compound 11 (0.38 g, 0.90 mmol) and 30% hydrogen bromide in acetic acid (2 mL) was stirred at about RT for about 2 h. The dihydrobromide salt of the product precipitated from the reaction mixture. Diethyl ether was added to the reaction mixture and Compound 12 (407.8 mg, 100% yield) was collected by filtration as a beige hygroscopic solid. MS (loop pos) MH$^+$=289 (100%). $^1$H NMR (300 MHz, DMSO-d$_6$), δ1.95–2.25 (m, 3H), 2.40–2.50 (m, 2H), 3.30–3.40 (m, 1H), 3.45–3.55 (m, 1H), 4.65–4.70 (m, 2H), 5.15–5.25 (m, 1H), 7.90–8.10 (m, 1H), 8.40 (s, 1H), 8.50–8.55 (m, 1H), 8.80–8.85 (m, 1H), 8.90 (s, 1H), 9.15–9.30 (m, 1H), 9.35–9.45 (m, 1H), 9.75–9.90 (m, 1H).

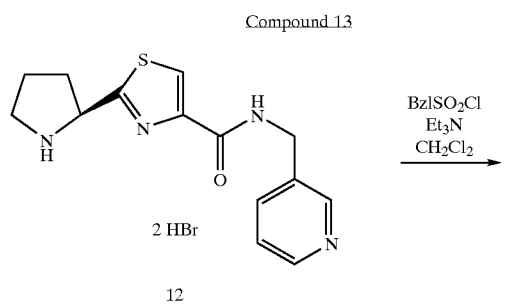

Compound 13

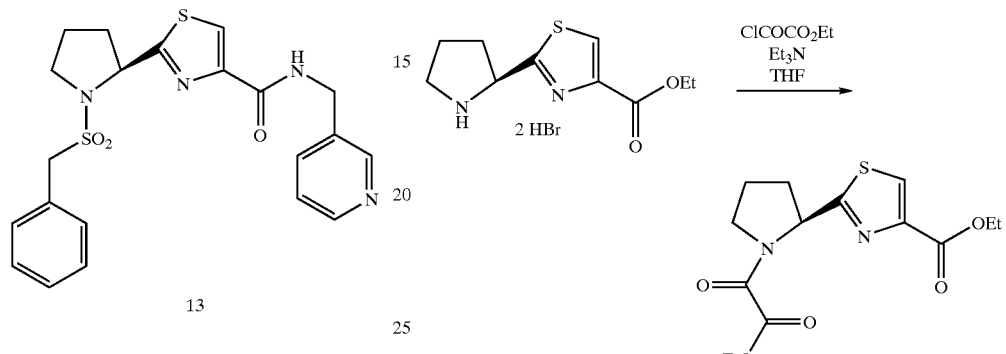

To a cold (0° C.) solution of the dihydrobromide salt of Compound 12 (203.0 mg, 0.453 mmol) and triethylamine (210 mL, 1.50 mmol) in methylene chloride (4 mL) was added α-toluenesulfonyl chloride (95.0 mg, 0.498 mmol). After 3 h, additional DMAP (10 mg), triethylamine (100 mL) and α-toluenesulfonyl chloride (44.8 mg) were added to the reaction mixture. The reaction mixture was stirred overnight. The solvent and volatiles were removed in vacuo. The crude product was purified by preparative TLC with 5% $CH_3OH$ in $CHCl_3$ to provide Compound 13 (67.6 mg, 34% yield) as a beige solid. MS (loop pos) $MH^+$=443(100%). $^1H$ NMR (300 MHz, $CDCl_3$), 67 1.90–2.05 (m, 2H), 2.10–2.20 (m, 2H), 3.30–3.50 (m, 2H), 4.3 (s, 2H), 4.60–4.70 (m, 2H), 4.85–4.95 (m, 1H), 7.10–7.20 (m, 1H), 7.30–7.45 (m, 5H), 7.50–7.65 (m, 1H), 7.70–7.75 (m, 1H), 8.05 (s, 1H), 8.50–8.55 (m, 1H), 8.60 (s, 1H).

Reference Example 10

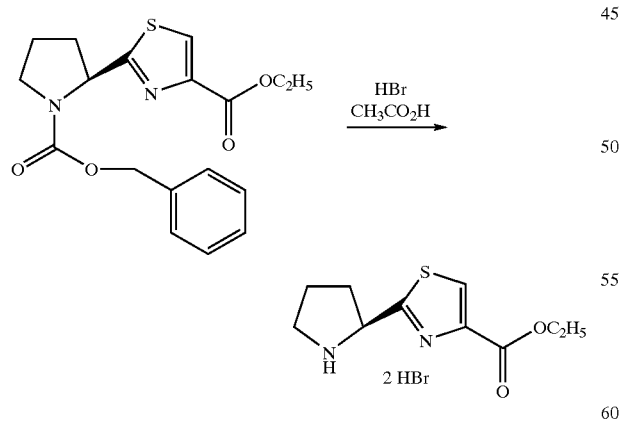

A solution of the N-CBz-protected-2-pyrrolidino-4-carbomethoxy thiazole from Reference Example 8 (3.33 g, 9.25 mmol) in $CH_3CO_2H$ (10 mL) was treated with 30% HBr in $CH_3CO_2H$ (4 mL) and stirred at about RT for about 6 h. The precipitated pyrrolidino thiazole dihydrobromide salt was covered with EtO and collected by filtration. The white solid was washed with additional $Et_2O$ and dried in the vacuum oven overnight at about RT to yield the pyrrolidine as the dihydrobromide salt (2.48 g, 69% yield). MS (loop pos) $MH^+$=227 (100%). Anal for $C_{10}H_{14}N_2O_2S$— 2.0 HBr: Calc'd C, 30.95; H, 4.15; N, 7.22; S, 8.26; Br, 41.69. Found C, 31.18; H, 4.07; N, 7.11; S, 7.91; Br, 41.84. $^1H$ NMR (300 MHz, DMSO-$d_6$), δ1.31 (t, J=7.12, 7.21Hz, 3H), 2.03–2.21 (m, 3H), 2.50–2.53 (m, 1H), 3.33–3.35 (m, 2H), 4.33 (q, J=7.04, 7.05, 7.08 Hz, 2H), 5.10 (t, J=6.94, 6.94 Hz, 1H), 8.66 (s, 1H), 9.2–9.5 (m, 2H), 9.80 (br s, 1H).

Reference Example 11

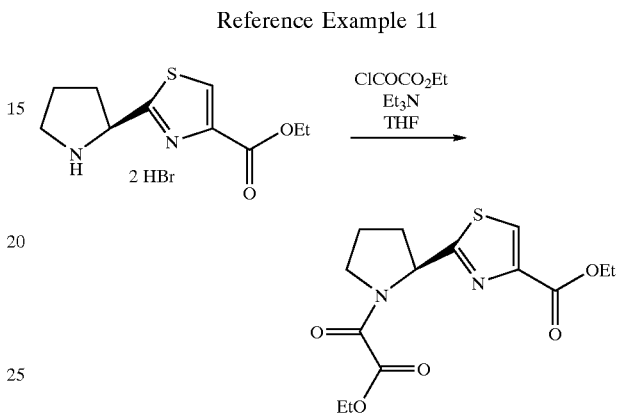

To a cold (0° C.) solution of the pyrrolidine from Reference Example 10 (1.53 g, 5.00 mmol) in $CH_2Cl_2$ (100 mL) was added triethylamine (1.70 mL, 1.21 mmol) and ethyl oxalyl chloride (0.82 mL, 7.34 mmol). The resultant reaction mixture was stirred at about RT for about 2 h, washed with aqueous NaCl solution (2×150 mL), dried over $Na_2SO_4$, filtered and concentrated to yield the oxamate (1.45 g, 89% yield) as an oil which was used without further purification. MS (loop pos) $MH^+$=327 (100%). $^1H$ NMR (300 MHz, DMSO-$d_6$), a 2:1 mixture of rotamers, δ1.20–1.35 (m, 6H), 1.8–2.2 (m, 3H), 2.30–2.45 (m, 1H), 3.65–3.80 (m, 2H), 4.20–4.35 (m, 4H), 5.35–5.40 (m, 0.67×1H), 5.59–5.61 (m, 0.33×1H), 8.42 (s, 0.67×1H), 8.47 (s, 0.33×1H).

Reference Example 12

To a cold (−78° C.) solution of the oxamate from Reference Example 11 (1.39 g, 4.26 mmol) in anhydrous THF (25 mL) was added excess 1,1-dimethylpropylmagnesium chloride (1M, 7.80 mL, 7.80 mmol) in Et$_2$O and the resultant mixture was stirred for about 5 h at about −78° C. The reaction mixture was quenched with aqueous NH$_4$Cl (25 mL) and extracted with EtOAc (2×25 mL). The EtOAc solution was dried over Na$_2$SO$_4$, filtered and concentrated to dryness. The crude product was chromatographed on silica gel with 35% EtOAc in hexane to give the oxamide (1.01 g, 67% yield) as a white solid. MS (loop pos) MH$^+$=353 (100%). $^1$H NMR (300 MHz, DMSO-d$_6$), a 4:1 mixture of rotamers, δ0.65 (t, J=7.1Hz and 1Hz, 0.20×3H), 0.75 (t, J=7.10 Hz, 7.10 Hz, 0.80×3H), 0.95 (s, 0.10×3H), 0.97 (s, 0.10×3H), 1.15 (s, 0.80×6H), 1.25 (t, J=7.10 Hz, 7.10 Hz, 3H), 1.55–1.70 (m, 2H), 1.85–2.00 (m, 2H), 2.05–2.15 (m, 1H), 2.25–2.40 (m, 1H), 3.35–3.60 (m, 1H), 4.33 (q, J=7.04, 7.05, 7.08 Hz, 2H), 5.30–5.40 (m, 1H), 8.40 (s, 0.80×1H), 8.45 (s, 0.20×1H).

Reference Example 13

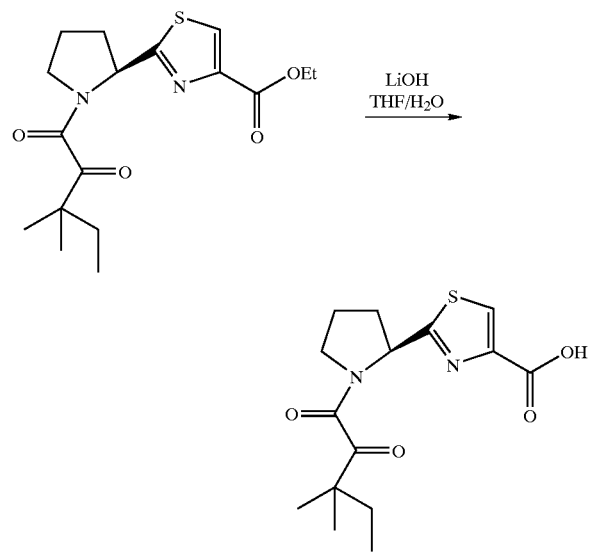

A solution of the ethyl ester from Reference Example 12 (0.95 g, 2.70 mmol) and lithium hydroxide (71.9 mg, 3.00 mmol) in a THF/H$_2$O mixture (2.5:1; 35 mL) was stirred at about 0° C. for about 1 h and at about RT for about 20 h. The reaction mixture was washed with Et$_2$O (2×50 mL), and acidified with aqueous citric acid. The precipitated carboxylic acid was extracted with CHCl$_3$ (2×75 mL). The CHCl$_3$ solution was dried over Na$_2$SO$_4$, filtered and concentrated to give the carboxylic acid (0.81 g, 93% yield) as a white solid which was used without further purification. MS (loop neg) M−1=323. $^1$H NMR (300 MHz, DMSO-d$_6$), a 4:1 mixture of rotamers, δ0.65 (t, J=7.1 Hz and 1 Hz, 0.20×3H), 0.75 (t, J=7.10 Hz, 7.10 Hz, 0.80×3H), 0.95 (s, 0.10×3H), 0.97 (s, 0.10×3H), 1.15 (s, 0.80×6H), 1.55–1.70 (m, 2H), 1.85–2.00 (m, 2H), 2.05–2.15 (m, 1H), 2.25–2.40 (m, 1H), 3.35–3.60 (m, 1H), 5.30–5.40 (m, 1H), 8.35 (s, 0.80×1H), 8.40 (s, 0.20×1H) 13.5 (s, 1H).

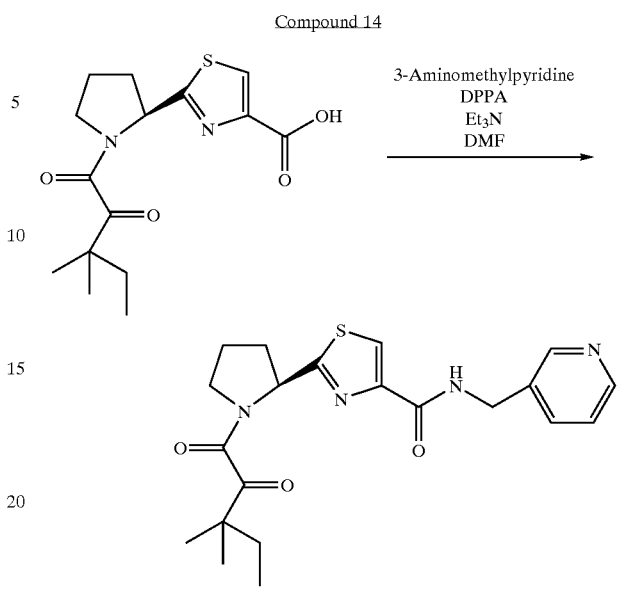

14

To a cold (0° C.) solution of the thiazole-4-carboxylic acid from Reference Example 13 (322.2 mg, 1.00 mmol) and triethylamine (310 mL, 2.22 mmol) in DMF (3 mL) was added diphenylphosphorylazide (250 mL, 1.16 mmol) and 3-aminomethylpyridine (110 mL, 1.08 mmol). The resultant mixture was stirred at about RT for about 1 d, diluted with aqueous NaCl solution (25 mL) and extracted with CHCl$_3$ (3×25 mL). The CHCl$_3$ solution was dried over Na$_2$SO$_4$, filtered and concentrated to dryness. The crude product was chromatographed on silica gel (elution with 100% EtOAc) to give 0.44 g of Compound 14 as a colorless immobile oil. The crude oil was then chromatographed on tapered preparative TLC plates with 5% CH$_3$OH in CHCl$_3$ to give Compound 14 (271.8 mg, 66% yield) as a colorless glass. MS (loop pos) MH$^+$=415 (100%). $^1$H NMR (300 MHz, DMSO-d$_6$), a 4:1 mixture of rotamers, δ0.64 (t, J=7.45 Hz, 7.45 Hz, 0.20×3H), 0.78 (t, J=7.40 Hz, 7.40 Hz, 0.80×3H), 0.95 (s, 0.10×3H), 0.97 (s, 0.10×3H), 1.15 (s, 0.80×6H), 1.45–1.65 (m, 2H), 1.90–2.05 (m, 2H), 2.10–2.20 (m, 1H), 2.25–2.40 (m, 1H), 3.42–3.48 (m, 1H), 3.50–3.58 (m, 1H), 4.47 (d, J=6.28 Hz, 2H), 5.31–5.33 (m, 0.20×1H), 5.37–5.40 (m, 0.80×1H), 7.33–7.37 (m, 1H), 7.70–7.73 (m, 1H), 8.21 (s, 0.80×1H), 8.25 (s, 0.20×1H), 8.44–8.46 (m, 1H), 8.54 (br s, 1H), 9.00 (t, J=6.17, 6.20 Hz, 1H).

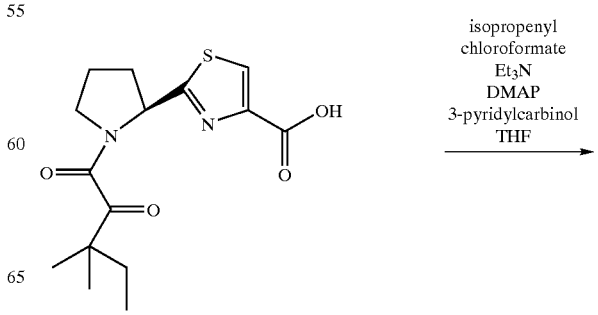

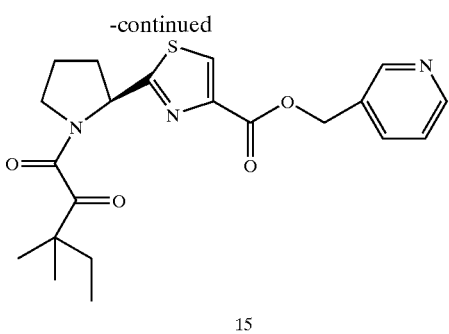

15

To a cold (0° C.) solution of the thiazole-4-carboxylic acid from Reference Example 13 (322.6 mg, 1.00 mmol), triethylamine (0.17 mL, 1.22 mmol), DMAP (13.0 mg, 0.100 mmol) and 3-pyridylcarbinol (0.11 mL, 1.13 mmol) in THF (15 mL) was added isopropenyl chloroformate (0.12 mL, 1.10 mmol). Upon warming to RT, the heterogeneous reaction mixture was stirred at about RT for about 20 h. The reaction was diluted with water and extracted with EtOAc (2×25 mL). The EtOAc solution was dried over Na$_2$SO$_4$, filtered and concentrated to dryness. The crude product was chromatographed on 4 tapered preparative TLC plates with 3% CH$_3$OH in CHCl$_3$ to afford Compound 15 (240.0 mg, 59% yield) as a light yellow solid. MS (loop pos) MH$^+$=416 (100%). $^1$H NMR (300 MHz, DMSO-d$_6$), a 4:1 mixture of rotamers, δ0.64 (t, J=7.45 Hz, 7.45 Hz, 0.20×3H), 0.78 (t, J=7.40 Hz, 7.40 Hz, 0.80×3H), 0.98 (s, 0.10×3H), 1.00 (s, 0.10×3H), 1.14 (s, 0.80×3H), 1.15 (s, 0.80×3H), 1.53–1.65 (m, 2H), 1.94–1.99 (m, 2H), 2.05–2.15 (m, 1H), 2.31–2.38 (m, 1H), 3.44–3.56 (m, 2H), 5.37 (m+s, 3H), 7.42–7.46 (m, 1H), 7.88–7.90 (d, J=7.70 Hz, 1H), 8.54–8.59 (m+s, 2H), 8.69 (s, 1H).

Reference Example 14

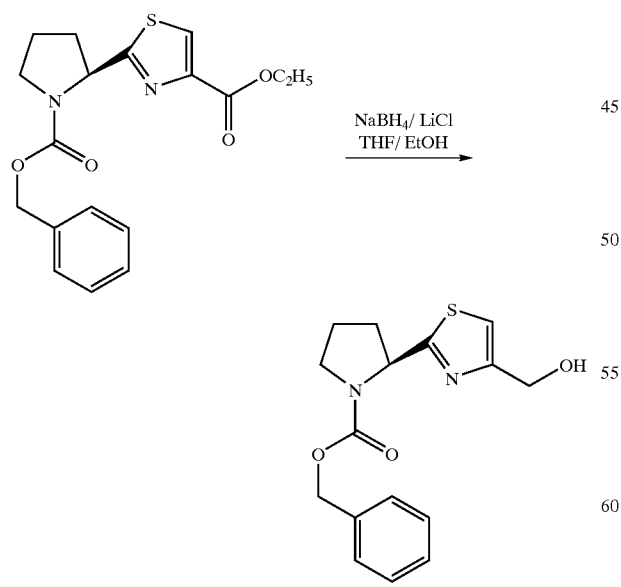

To a solution of the 4-carbomethoxythiazole from Reference Example 8 (3.64 g, 10.0 mmol) and lithium chloride (2.12 g, 50.0 mmol) in EtOH (100 mL) and THF (75 mL) was added sodium borohydride (1.94 g, 51.3 mmol). After 6 h, an additional 224 mg of LiCl and 205 mg of NaBH$_4$ were added to the reaction mixture and stirred for about an additional 18 h. The reaction mixture was quenched with aqueous ammonium chloride and extracted with CHCl$_3$ (3×100 mL). The CHCl$_3$ solution was dried over Na$_2$SO$_4$, filtered and concentrated to dryness. The crude product was chromatographed on silica gel with 5% CH$_3$OH in CHCl$_3$ to give the alcohol (2.39 g, 75% yield) as a colorless oil. MS (loop pos) MH$^+$=319 (100%). $^1$H NMR (300 MHz, CDCl$_3$), δ1.85–2.05 (m, 3H), 2.10–2.40 (m, 2H), 2.60–2.70 (m, 1H), 3.40–3.55(m, 1H), 3.60–3.70 (m, 1H), 4.65–4.75 (m, 2H), 5.05–5.30 (m, 3H), 7.05 (br s, 1H), 7.10 (br s, 1H), 7.20–7.40 (m, 3H).

Compound 16

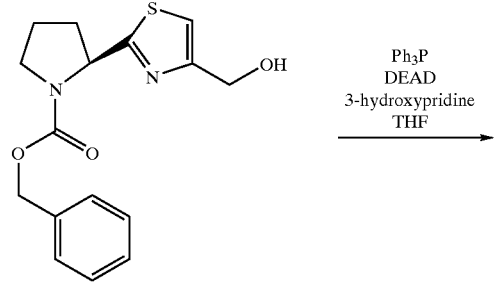

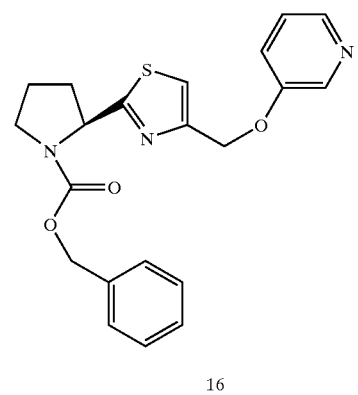

16

The thiazole-4-methanol from Reference Example 14 (2.17 g, 6.83 mmol) was combined with triphenylphosphine 3.38 g, 12.8 mmol), diethylazodicarboxylate (1.64 mL, 10.4 mmol) and 3-hydroxypyridine (0.97 g, 10.2 mmol) in THF (110 mL) and treated in the same manner as described for (2.08 g) and a hydrazine byproduct as an oil. MS (loop pos) MH$^+$=396 (100%). $^1$H NMR (300 MHz, DMSO-d$_6$), δ1.85–2.05 (m, 3H), 2.10–2.40 (m, 1H), 3.40–3.55 (m, 2H), 4.90–5.20 (m, 5H), 7.05 (br s, 1H), 7.10 (br s, 1H), 7.30–7.60 (m, 5H), 8.12–8.15 (m, 1H), 8.35–8.37 (m, 1H), 9.00 (s, 1H).

Compound 17

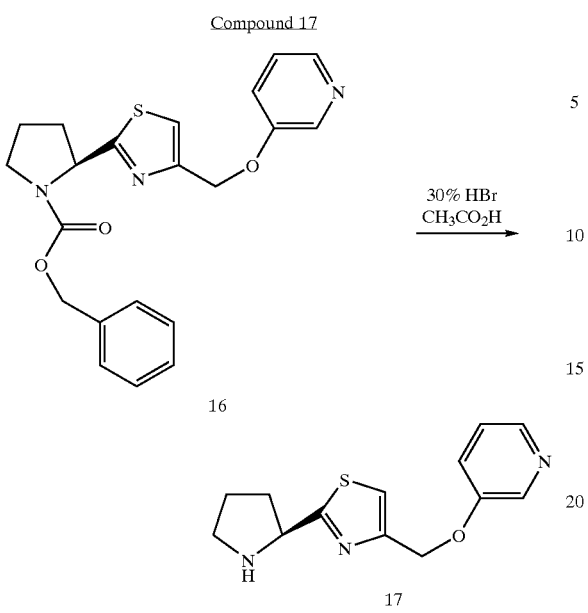

A mixture of crude Compound 16 (1.85 g) and 30% HBr in CH$_3$CO$_2$H (12 mL) was stirred at about RT for about 2 h. The reaction mixture was diluted with H$_2$O (25 mL) and extracted with Et$_2$O (3×75 mL). The acidic aqueous layer was basified with aqueous Na$_2$CO$_3$ and the highly water-soluble free base was extracted with CHCl$_3$ (10×100 mL). The aqueous layer was concentrated to a moist solid and extracted with CHCl$_3$ (3×125 mL). The combined CHCl$_3$ solution was dried (Na$_2$SO$_4$), filtered and concentrated to give Compound 17 (0.55 g) as an oil. MS (loop pos) MH$^+$=262 (40%). $^1$H NMR (300 MHz, DMSO-d$_6$), δ1.67–1.84 (m, 2H), 2.10–2.22 (m, 1H), 2.82–3.00 (m, 2H), 3.43 (br s, 1H), 4.41–4.45 (m, 1H), 5.16 (s, 2H), 7.31–7.36 (m, 1H), 7.47–7.51 (m, 1H), 7.55 (s, 1H), 8.18 (d, J=4.36 Hz, 1H), 8.37 (d, J=2.86 Hz, 1H).

Compound 18

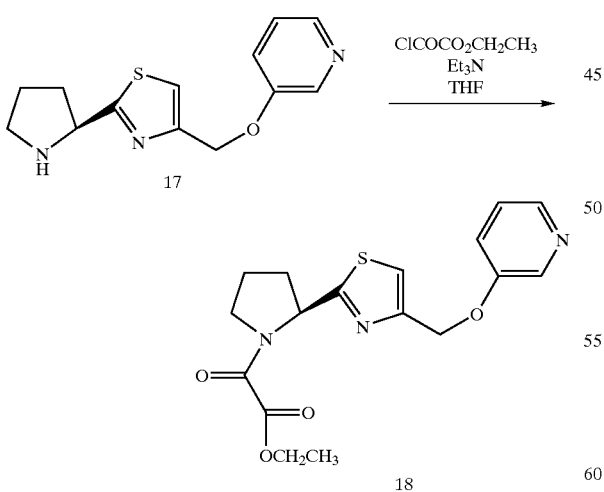

Compound 17 (0.55 g, 2.00 mmol), triethylamine (0.69 mL, 4.95 mmol) and ethyl oxalyl chloride (0.35 mL, 3.13 mmol) in CH$_2$Cl$_2$ (100 mL) were treated in the same manner as described for the preparation of Compound 7 to give Compound 18 (0.33 g, 46% yield) as an oil. MS (loop pos) MH$^+$=362 (100%). $^1$H NMR (300 MHz, DMSO-d$_6$), a 3:2 mixture of rotamers, δ1.05 (t, J=7.40 Hz, 7.41Hz, 0.40×3H), 1.25 (t, J=7.41, 7.40 Hz, 0.60×3H), 1.80–2.15 (m, 3H), 2.25–2.45 (m, 1H), 3.55–3.75 (m, 2H), 4.00 (q, J=7.12 Hz, 7.13 Hz, 7.10 Hz, 0.4×2H), 4.30 (q, J=7.12 Hz, 7.13 Hz, 7.10 Hz, 0.60×2H), 5.20 (s, 2H), 5.32–5.39 (m, 0.60×1H), 5.40–5.55 (m, 0.40×1H), 7.32–7.40 (m, 1H), 7.45–7.52 (m, 1H), 7.69 (s, 0.60×1H), 7.75 (s, 0.40×1H), 8.19 (d, J=4.36 Hz, 1H), 8.38–8.39 (m, 1H).

Compound 19

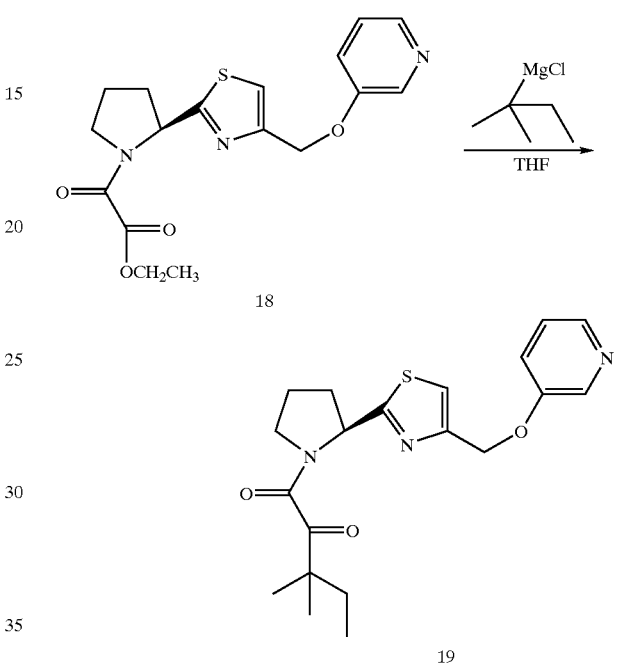

Compound 18 (0.31 g, 0.86 mmol) and 1,1-dimethylpropyl magnesium chloride (1M, 2.25 mL, 2.25 mmol) in THF (10 mL) were treated in the same manner as described for the preparation of Compound 8 to give Compound 19 (0.17 g, 51% yield) as yellow oil. MS (loop pos) MH$^+$=388 (100%). $^1$H NMR (300 MHz, DMSO-d$_6$), a 4:1 mixture of rotamers, δ0.65 (t, J=7.41Hz, 7.42 Hz, 0.20×3H), 0.79 (t, J=7.37, 7.40 Hz, 0.80×3H), 0.93 (s, 0.10×6H), 0.97 (s, 0.10×6H), 1.16 (s, 0.40×6H), 1.17 (s, 0.40×6H), 1.63 (q, J=7.40, 7.42, 7.45 Hz, 2H), 1.95–1.97 (m, 2H), 2.07–2.13 (m, 1H), 2.26–2.36 (m, 1H), 5.20 (s, 2H), 5.34–5.40 (m, 1H), 7.32–7.36 (m, 1H), 7.49–7.53 (m, 1H), 7.70 (s, 0.80× 1H), 7.76 (s, 0.20×1H), 8.19 (d, J=3.96 Hz, 1H), 8.38 (br s, 1H).

Reference Example 15

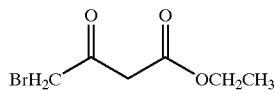

To a cold (0° C.) solution of ethyl acetoacetate (65 mL, 510 mmol) in anhydrous Et$_2$O (100 mL) was added bromine (26.40 mL, 512.4 mmol). The reaction mixture stood at about RT for about 1 d, was then poured onto ice and washed with aqueous Na$_2$CO$_3$ until basic. The Et$_2$O solution was washed with brine and dried over CaCl$_2$ for about 4 d. The Et$_2$O solution was filtered and concentrated to yield 81.66 g of light brown oil that was stabilized with solid $K_2CO_3$. $^1H$ NMR (300 MHz, $CDCl_3$) δ1.50 (t, J=7.40, 7.40 Hz, 3H), 3.70 (s, 2H), 4.00 (s, 2H), 4.20 (q, J=7.40, 7.40 Hz, 2H).

Reference Example 16

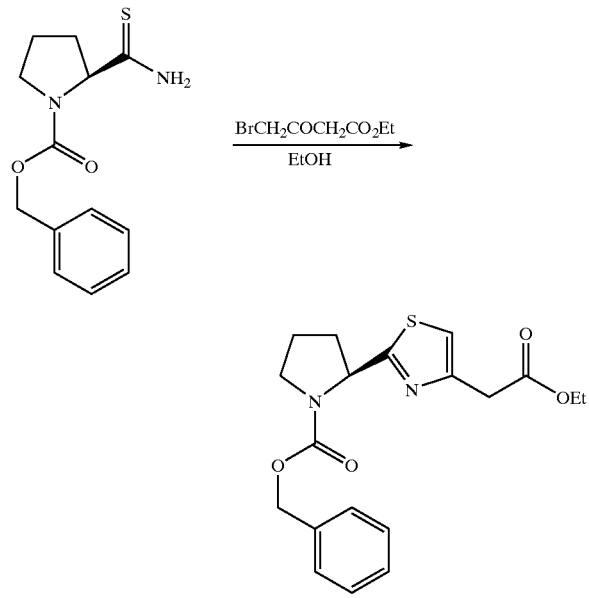

A solution of the N-CBz-proline thioamide from Reference Example 8 (4.36 g, 16.5 mmol), and 90% ethylybromoacetoacetate from Reference Example 15 (4.80 g, 22.5 mmol) in ethanol (170 mL) was stirred at reflux for about 2 h. The reaction mixture was concentrated to dryness. The residue was chromatographed on silica gel with 1% $CH_3OH$ in $CHCl_3$ to give the thiazole (6.25 g, 100% yield) as an oil. MS (loop pos) $MH^+$=375 (40%). $^1H$ NMR (300 MHz, DMSO-$d_6$), δ1.15–1.25 (m, 3H), 1.80–2.10 (m, 3H), 2.25–2.40 (m, 1H), 3.35–3.55 (m, 2H), 3.75 (s, 2H), 4.05 (q, J=7.40, 7.42, 7.45 Hz, 2H), 4.95–5.20 (m, 3H), 7.10 (br s, 1H), 7.25–7.40 (m, 5H).

Reference Example 17

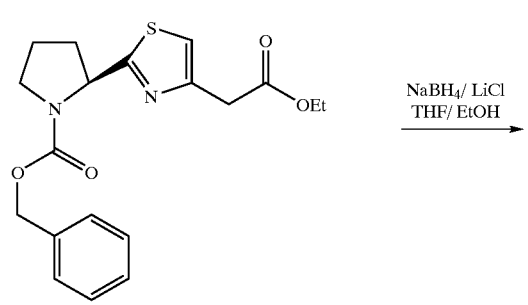

-continued

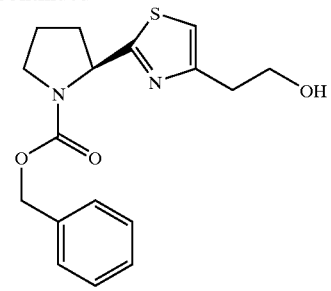

The ethyl ester from Reference Example 16 (3.019, 8.00 mmol), lithium chloride (1.72 g, 40.6 mmol) and sodium borohydride (1.51 g, mmol) in EtOH/THF (4:3; 175 mL) were combined and treated in the same manner as described for the preparation of the product of Reference Example 14 to give the alcohol (2.40 g, 90% yield) as a light yellow oil. MS (loop pos) $MH^+$=333 (100%). $^1H$ NMR (300 MHz, DMSO-$d_6$), δ1.80–2.05 (m, 3H), 2.20–2.40 (m, 1H), 2.80 (t, J=6.52, 6.52 Hz, 2H), 3.40–3.60 (m, 2H), 3.65–3.70 (m, 2H), 4.65 (t, 1H (OH), 4.90–5.20 (m, 3H), 7.05 (br s, 1H), 7.15 (br s, 1H), 7.25–7.40 (m, 4H).

Compound 20

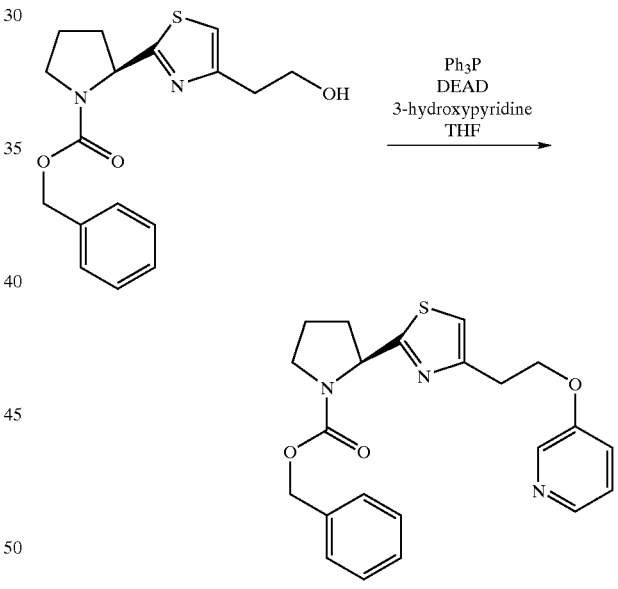

20

The thiazole-4-ethanol from Reference Example 17 (1.51 g, 4.55 mmol), triphenylphosphine (2.37 g, 9.04 mmol), diethylazodicarboxylate (1.00 mL, 6.35 mmol) and 3-hydroxypyridine (0.60 g, 6.31 mmol) in THF (20 mL) were treated in the same manner as described for the preparation of Compound 5 to give crude Compound 20 (0.82 g) as an oil. MS (loop pos) $MH^+$=410 (100%). $^1H$ NMR (300 MHz, DMSO-$d_6$), δ1.90–2.02 (m, 3H), 2.20–2.40 (m, 1H), 3.15 (t, J=6.52, 6.52 Hz, 2H), 3.47–3.60 (m, 2H), 4.30–4.40 (m, 2H), 4.93–5.20 (m, 3H), 7.05 (br s, 1H), 7.20–7.70 (m, 7H), 8.15 (d, J=4.3 Hz, 1H), 8.28–8.32 (m, 1H).

Compound 21

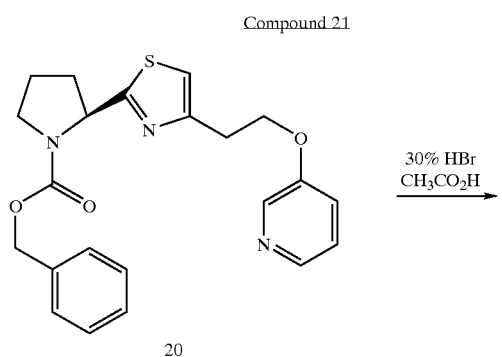

30% HBr
CH₃CO₂H

Compound 20 (0.71 g), and 30% HBr in CH₃CO₂H (5 mL) was treated in the same manner as described for the preparation of Compound 17 to give Compound 21 (0.85 g) as a hygroscopic dihydrobromide salt. MS (loop pos) MH⁺=276 (100%). ¹H NMR (300 MHz, DMSO-d₆), δ1.90–2.20 (m, 3H), 2.40–2.50 (m, 1H), 3.25–3.40 (m+t, J=6.52, 6.52 Hz, 4H), 4.60 (t, J=6.52, 6.52 Hz, 2H), 5.00–5.10 (m, 1H), 7.60 (s, 1H), 7.95–8.05 (m, 1H), 8.25–8.30 (m, 1H), 8.65 (d, J=4.3 Hz, 1H), 8.80 (s, 1H), 9.10–9.25 (br s, 1H), 9.75–9.90 (br s, 1H).

Compound 22

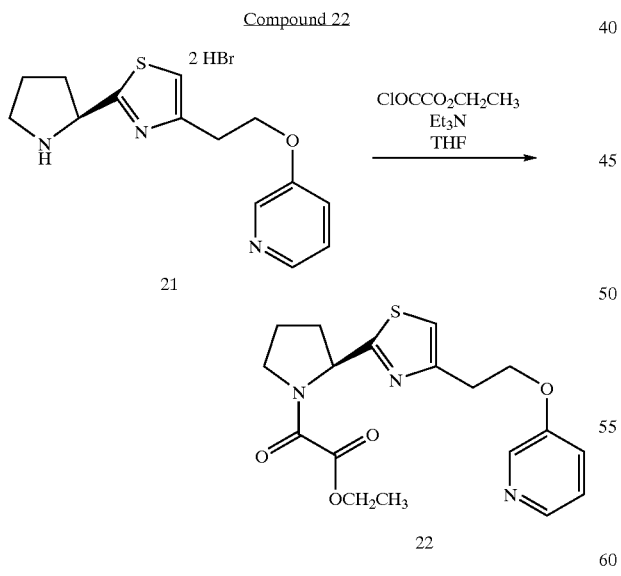

ClOCCO₂CH₂CH₃
Et₃N
THF

Compound 21 (0.78 g, 1.78 mmol), triethylamine (0.63 mL, 4.52 mmol) and ethyl oxalyl chloride (0.30 mL, 2.68 mmol) in CH₂Cl₂ (25 mL) were treated in the same manner as described for the preparation of Compound 7 to give Compound 22 (0.42 g, 63% yield) as an oil. MS (loop pos, MH⁺=376 (100%). ¹H NMR (300 MHz, DMSO-d₆), a 3:2 mixture of rotamers δ1.20–1.30 (m, 3H), 1.95–2.10 (m, 3H), 2.25–2.45 (m, 1H), 3.15 (q, J=7.40, 7.42, 7.45 Hz, 2H), 3.50–3.75 (m, 2H), 4.20–4.40 (m, 4H), 5.30–5.35 (m, 0.60× 1H), 5.50–5.55 (m, 0.40×1H), 7.25–7.33 (m, 1H), 7.35–7.40 (m, 2H), 8.15–8.18 (m, 1H), 8.20–8.22 (m, 1H), (q, J=7.40, 7.42, 7.45 Hz, 2H).

Compound 23

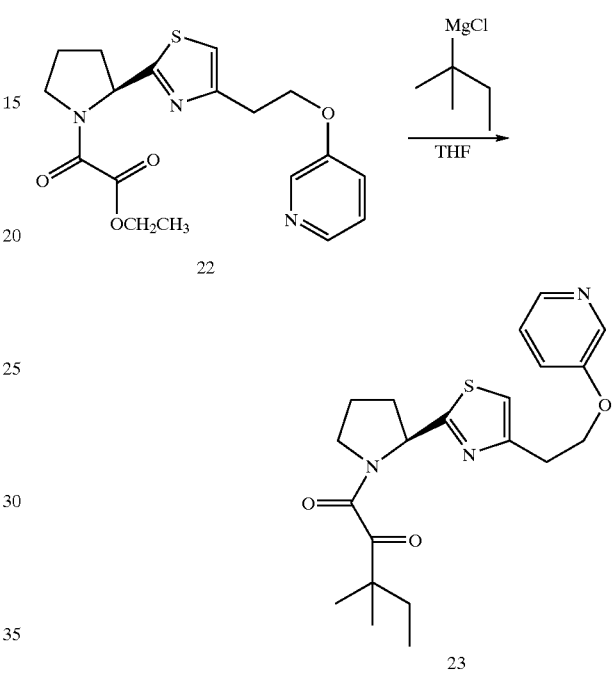

MgCl

THF

Compound 22 (0.41 g, 1.09 mmol) and 1,1-dimethylpropyl magnesium chloride (1M, 3.00 mL, 3.00 mmol) in THF (25 mL) were treated in the same manner as described for the preparation of Compound 8 to give Compound 23 (224.4 mg, 51% yield) as an oil. MS (loop pos) MH⁺=402 (100%). ¹H NMR (300 MHz, DMSO-d₆), a 4:1 mixture of rotamers, δ0.63 (t, J=7.41 Hz, 7.42 Hz, 0.20×3H), 0.79 (t, J=7.37, 7.40 Hz, 0.80×3H), 0.89 (s, 0.10×6H), 0.93 (s, 0.10×6H), 1.15 (s, 0.40×6H), 1.16 (s, 0.40×6H), 1.59–1.64 (m, 2H), 1.95–2.08 (m, 3H), 2.23–2.33 (m, 1H), 3.16 (t, J=6.30 Hz, 6.30 Hz, 2H), 3.40–3.57 (m, 2H), 4.36 (t, J=6.64, 6.64 Hz, 2H), 5.30–5.37 (m, 1H), 7.29–7.41 (m, 3H), 8.16 (d, J=4.25 Hz, 1H), 8.26–8.29 (m, 1H).

Compound 24
Method A

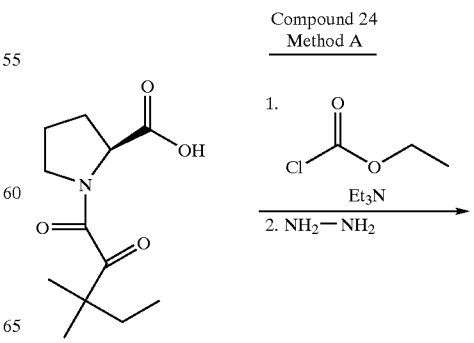

1.

Et₃N

2. NH₂—NH₂

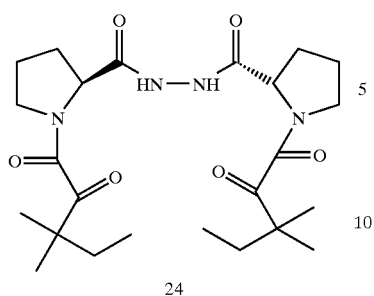

24

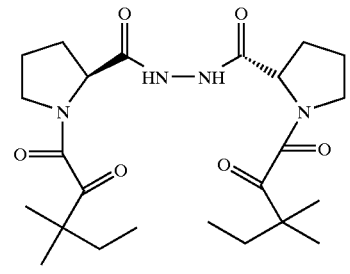

24

To a stirred solution of (2S)-1-(1,2-dioxo-3,3-dimethylpentyl)-2-pyrrolidinecarboxylic acid (4.557 g, 18.89 mmol, prepared as described in WO 96/40633) in tetrahydrofuran (130 mL) cooled to about −15° C. (MeOH/ice bath) was added triethylamine (1.908 g, 2.63 mL, 18.89 mmol) followed by ethyl chloroformate (2.05 g, 1.806 mL, 18.86 mmol). After stirring at about −15° C. to about −10° C. for about 30 min, the precipitated solid was removed by filtration and the filtrate and washings were brought to about a volume of 170 mL with the addition of tetrahydrofuran.

While stirring the solution of the mixed anhydride (85 mL, 9.32 mmol) at about 0° C., hydrazine monohydrate (0.48 mL, 9.79 mmol) was added. The mixture was stirred and allowed to warm to about RT overnight. After removing the solvent in vacuo, the residue was purified by column chromatography on silica gel using 50% ethyl acetate/dichloromethane as an eluent to obtain Compound 24 (0.64 g, 28.7% yield) as a colorless solid which was recrystallized from ether/pentane, mp 177–178° C. CIMS 479 (MH+), 501 (M+Na+). $^1$H NMR (300 MHz, CDCl$_3$, mixture of rotamers) δ (for the major, trans rotamer) 9.06 (br s, 2H), 4.61 (m, 2H), 3.50–3.46 (m, 4H), 2.40–2.36 (m, 2H), 2.13–1.94 (m, 6H), 1.83–1.64 (m, 4H), 1.25 and 1.21 (each s, each 6H), 0.87 (t, 3H). IR (KBr) cm$^{-1}$: 3261, 2970, 1706, 1684, 1636. Anal. Calcd. for C$_{24}$H$_{38}$N$_4$O$_6$: C, 60.23; H, 8.00; N, 11.71. Found: C, 60.30; H, 8.03; N, 11.58.

Compound 24 was also prepared as described in Method B.

Method B - Compound 24

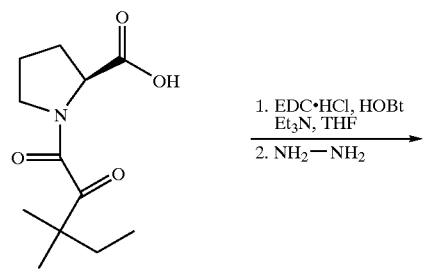

To a stirred solution of (2S)-1-(1,2-dioxo-3,3-dimethylpentyl)-2-pyrrolidinecarboxylic acid (2.4229 g, 10 mmol), prepared as described in WO 96/40633, in tetrahydrofuran (50 mL) were added sequentially at about RT: triethylamine (4.18 mL, 30 mmol), ethyl dimethylamino-propylcarbodiimide hydrochoride, "EDC.HCl," (1.917 g, 10 mmol) and hydroxybenzotriazole hydrate "HOBt.H$_2$O" (1.53 g, 10 mmol). After about 5 min, a solution of hydrazine in tetrahydrofuran (1M, 5 mL, 5 mmol) was added and the mixture was stirred for about 18 h. Tetrahydrofuran was removed in vacuo (<35°) and the residue was dissolved in dichloromethane and washed successively with water, 1% aq. HCl, and water and dried (Na$_2$SO$_4$). Following filtration, dichloromethane was removed in vacuo and the crude product was purified by column chromatography on silica gel eluting with 1.5% methanol in dichloromethane to obtain Compound 24 (18% yield), [α]$^{25}_D$ −95.8° (c=0.33, CHCl$_3$), identical in every respect to that obtained by Method A.

Method A was utilized to prepare Compounds 25–29.

Method A - Compound 25

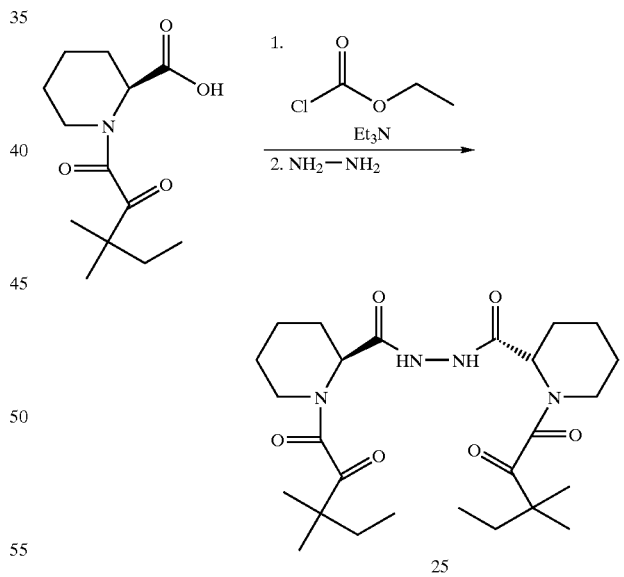

Utilizing (2S)-1-(1,2-dioxo-3,3-dimethylpentyl)-2-piperidinecarboxylic acid (prepared essentially as described for (2S)-1-(1,2-dioxo-3,3-dimethylpentyl)-2-pyrrolidinecarboxylic acid in WO 96/40633), Compound 25 was isolated as a colorless solid (38% yield), mp 180–181° C. (ether/pentane). CIMS 507 (MH+), 529 (M+Na+). $^1$H NMR (CDCl$_3$, mixture of rotamers) δ (for the major, trans rotamer) 8.07 (br m, 2H), 5.17 (d, 2H), 4.29–4.08 (m, 2H), 3.39 (d, 4H), 2.89 (t, 1H), 2.40–2.05 (m, 3H), 1.89–1.44 (m, 10H), 1.23 and 1.22 (each s, each 6H), 0.90 (t, 6H). IR (KBr) cm$^{-1}$: 3309, 2969, 1699, 1646, 1610. Anal. Calcd. for C$_{26}$H$_{42}$N$_4$O$_6$: C, 61.64; H, 8.36; N, 11.06. Found: C, 61.45; H, 8.58; N, 10.76.

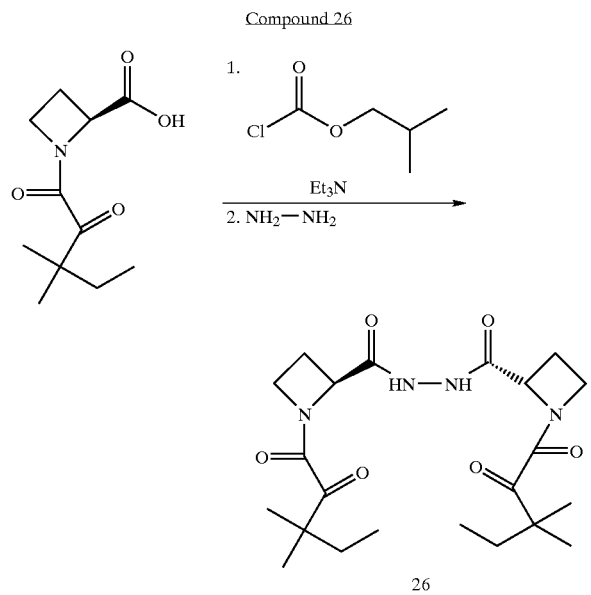

Compound 26

Utilizing (2S)-1-(1,2-dioxo-3,3-dimethylpentyl)-2-azetidinecarboxylic acid (prepared essentially as described for (2S)-1-(1,2-dioxo-3,3-dimethylpentyl)-2-pyrrolidinecarboxylic acid in WO 96/40633), Compound 26 was isolated as a transparent sticky foam (35% yield), mp <58° C., [α]$^{25}_D$–93.4° (CHCl$_3$). CIMS 451 (MH$^+$), 473 (M+Na$^+$). $^1$H NMR (CDCl$_3$, mixture of rotamers) δ (for the major, trans rotamer) 9.70 (br s, 2H), 5.02 (d, d, 2H), 4.34–4.18 (m, 4H), 2.85–2.73 (m, 2H), 2.61–2.49 (m, 2H), 1.84–1.73 (m, 6H), 1.25 and 1.23 (each s, each 6H), 0.84 (t, 6H). IR (KBr) cm$^{-1}$: 3498, 3247, 2972, 1703, 1636.

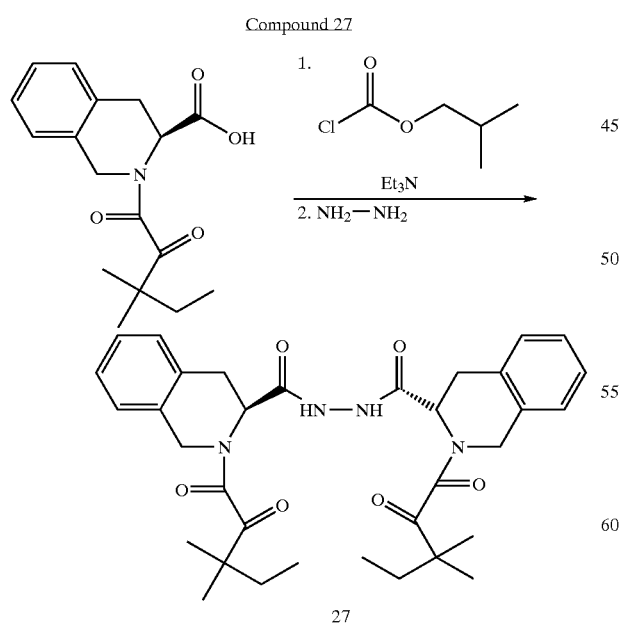

Compound 27

Utilizing (3S)-2-(1,2-dioxo-3,3-dimethylpentyl)-1,2,3,4-tetrahydroisoquinolinecarboxylic acid (prepared essentially as described for (2S)-1-(1,2-dioxo-3,3-dimethylpentyl)-2-pyrrolidinecarboxylic acid in WO 96/40633), Compound 27 was isolated as a colorless solid (41% yield, ether/pentane) mp 108–110° C.; [α]$^{25}_D$–55.12° (CHCl$_3$). CIMS 603 (MH$^+$), 625 (M+Na). $^1$H NMR (CDCl$_3$, mixture of rotamers) δ (for the major trans rotamer) 7.22–7.03 (m, 8H), 5.25–4.95 (m, 2H), 4.51–4.25 (m, 4H), 3.16–3.10 (m, 2H), 1.72–1.66 (m, 2H), 1.22 and 1.21 (for each s and each 6H), 0.89 (t, 6H). IR (KBr) cm$^{-1}$: 3219, 2969, 1701, 1639. Anal. Calcd. for C$_{34}$H$_{42}$N$_4$O$_6$: C, 67.75; H, 7.02; N, 9.30. Found: C, 67.54; H, 7.04; N, 9.13.

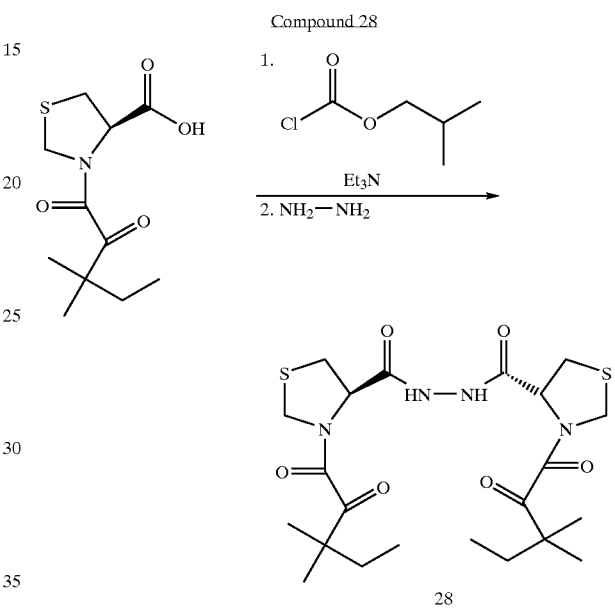

Compound 28

Utilizing (4R)-3-(1,2-dioxo-3,3-dimethylpentyl)-4-thiazolidinecarboxylic acid (prepared essentially as described for (2S)-1-(1,2-dioxo-3,3-dimethylpentyl)-2-pyrrolidinecarboxylic acid in WO 96/40633), Compound 28 was isolated as a colorless foam (39.8% yield), mp 77–82° C. (ether/pentane); [α]$^{25}_D$–15.6° (c=0.276, CHCl$_3$). CIMS 515 (MH$^+$), 537 (M+Na$^+$). $^1$H NMR (CDCl$_3$, mixture of rotamers) δ (for the major, trans rotamer) 8.93 (br s, 2H), 5.05–4.98 (m, 2H), 4.54–4.43 (m, 4H), 3.59–3.54 (m, 2H), 3.25–3.21 (9 m, 2H), 1.78–1.74 (m, 4H), 1.25 and 1.23 (each s, each 6H), 0.88 (t, 3H). IR (KBr) cm$^{-1}$: 3270, 2970, 1703, 1642, 1418. Anal. Calcd. for C$_{22}$H$_{34}$N$_4$O$_6$: C, 51.34; H, 6.66; N, 10.89. Found: C, 51.52; H, 6.67; N, 11.06.

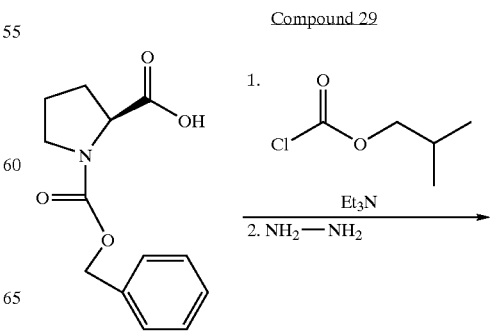

Compound 29

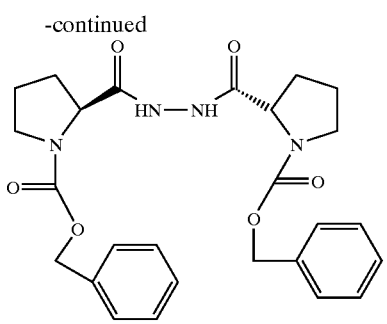

29

Utilizing (2S)-1-benzyloxycarbonyl-2-pyrrolidinecarboxylic acid, Compound 29 was isolated as a colorless foam, of undefined melting range; $[\alpha]^{25}_D$ –56.1° (CHCl$_3$). CIMS 495 (MH+), 518 (M+Na+). $^1$H NMR (CDCl$_3$, mixture of rotamers) δ (for the major, trans rotamer) 9.11 (br s, 2H), 7.36 (br s, 10H), 5.23–5.14 9 m, 4H), 4.41 (br s, 2H), 3.55–3.44 (m, 4H), 2.36–1.94 (m, 8H). IR (KBr) cm$^{-1}$ 3496, 1704, 1499, 1420, 1358.

Compounds 28 and 29 also were prepared as described in Method C.

Method C - Compound 28

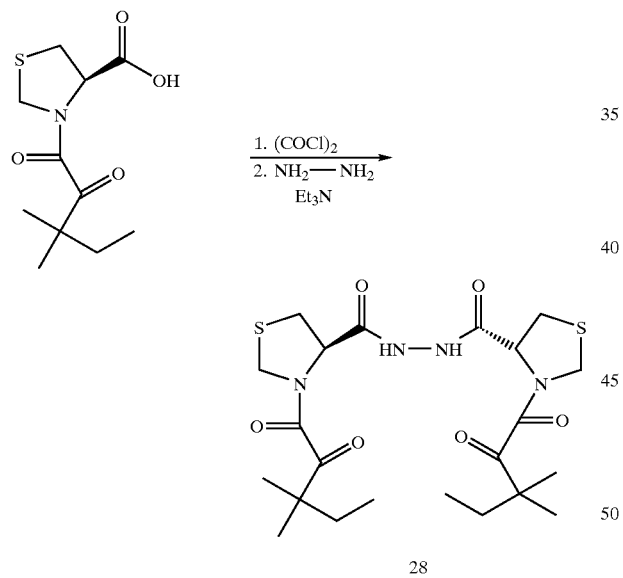

28

To a solution of (4R)-3-(1,2-dioxo-3,3-dimethylpentyl-4-thiazolidine carboxylic acid (1.63 g, 6.29 mmol) in dichloromethane (100 mL), cooled in an ice bath, was added a solution of oxalyl chloride (0.72 mL, 8.25 mmol) in dichloromethane (5 mL) over about a 20 min period. After stirring the mixture at about RT for about 2 h the solvent was removed by evaporation in vacuo <40° C. After thoroughly drying the residue under vacuum for about 1 h, it was dissolved in dry tetrahydrofuran (50 mL). To this solution stirring at about 0° C. was added a mixture of 1M solution of hydrazine in tetrahydrofuran (3.15 mL, 3.15 mM) and triethylamine (1.32 mL, 9.47 mM) over about a 30 min period; the mixture was stirred at about RT overnight. After about 24 h the solvent was removed by evaporation in vacuo and the residue was partitioned between 1N aqueous hydrochloric acid and dichloromethane. The organic layer was dried (Na$_2$SO$_4$) and evaporated in vacuo. The crude product was purified by flash chromatography on silica gel eluting with 2% methanol in dichloromethane to obtain Compound 28 (1.18 g, 73% yield), $[\alpha]^{25}_D$ –15.6° (c=0.276, CHCl$_3$), identical in all respects with the authentic sample obtained as described in Method A.

Compound 29

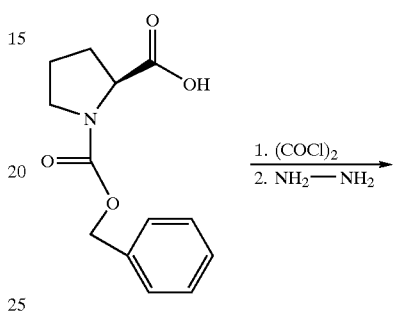

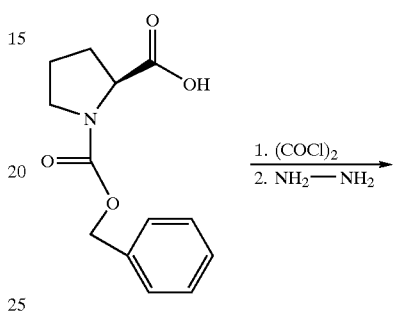

29

To a solution of Z-proline (10 g, 40.12 mmol) in dichloromethane (100 mL), cooled to about 0° C., oxalyl chloride (4.19 mL, 48 mmol), was added dropwise under nitrogen over about a 20 min period followed by dimethylformamide (3 drops). After stirring for about 2 h at about RT, the mixture was evaporated to dryness in vacuo and dried again at high vacuum for about 30 min. The residue was dissolved in dry tetrahydrofuran (THF, 160 mL); this solution was added to a 1M solution of hydrazine in tetrahydrofuran (40 mL, 40 mM) over about a 2 min period and then stirred at about RT for about 18 h. The mixture was evaporated to dryness in vacuo. The residue was taken up in ethyl acetate (300 mL) and washed sequentially with 1% aqueous HCl and water, the organic layer dried (Na$_2$SO$_4$), filtered and evaporated in vacuo to afford a colorless oily residue. The crude product was purified by flash chromatography on silica gel eluting with 2% methanol/dichloromethane to afford Compound 29 (8.8 g, 88.7% yield), $[\alpha]^{25}_D$ –56.1° (c=1.0, CHCl$_3$), as a colorless foam identical with the authentic sample obtained as described in Method A.

Compound 30 was prepared as described in Methods D, E, and F.

Method D - Compound 30

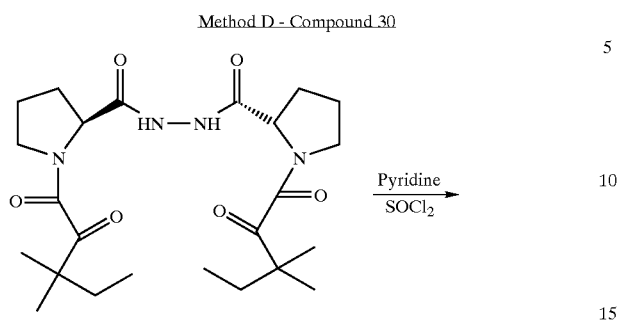

To a vigorously stirred ice cold slurry of Compound 24 (0.567 g, 1.185 mmol) in dry ether (400 mL) was added pyridine (0.12 mL, 3.35 mmol) followed by thionyl chloride (0.120 mL, 1.66 mmol). After stirring the mixture at about 0° C. for about 2 h the precipitated solids were removed by filtration, washed quickly with dry ether and the combined filtrates were evaporated to dryness in vacuo at <40°. The residue (0.6235 g foam) was dissolved in dry toluene (25 mL) and heated to reflux under nitrogen for about 3 h. The residue obtained by evaporating toluene in vacuo was purified by column chromatography on silica gel/CH$_2$Cl$_2$. Elution with 1% methanol/methylene chloride gave the title Compound 30 (0.354 g, 63.6% yield) as a colorless solid, recrystallized from ether/pentane, mp 123–124° C.; $[\alpha]^{24}_D$ –74.6° (c=0.8,CHCl$_3$). CIMS 461 (MH$^+$), 483 (M+Na$^+$). $^1$H NMR (CDCl$_3$, mixture of rotamers) δ (for the major, trans rotamer) 5.32 (d, d, J=3.0, 7.6), 3.59 (m, 4H), 2.33–2.07 (m, 8H), 1.80–1.65 (m, 4H), 1.23 and 1.20 (each s, each 6H), 0.86 (t, 6H). IR (KBr) cm$^{-1}$: 2972, 1704, 1641. Anal. Calcd. for C$_{24}$H$_{36}$N$_4$O$_5$: C, 62.59; H, 7.88; N, 12.16. Found: C, 62.68; H, 7.75; N, 12.14.

Method E - Compound 30

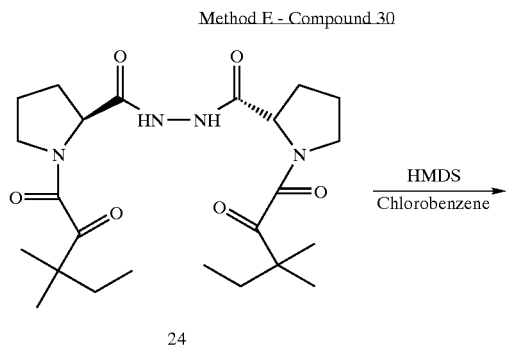

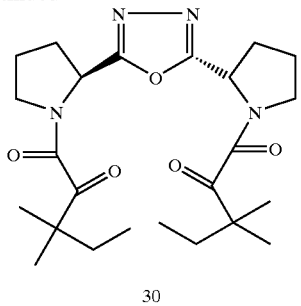

To a solution of Compound 24 (0.112 g, 0.234 mM) in chlorobenzene (10 mL) were added hexamethyldisilazane (0.123 mL, 0.585 mM), imidazole (10 mg), tetrabutyl ammonium fluoride (10 mg) and the mixture heated to reflux under nitrogen for about 72 h. Chromatographic purification of the crude product gave Compound 30 identical with the authentic sample as described in Method D by thin layer chromatography and mass spectral data.

Method F - Compound 30

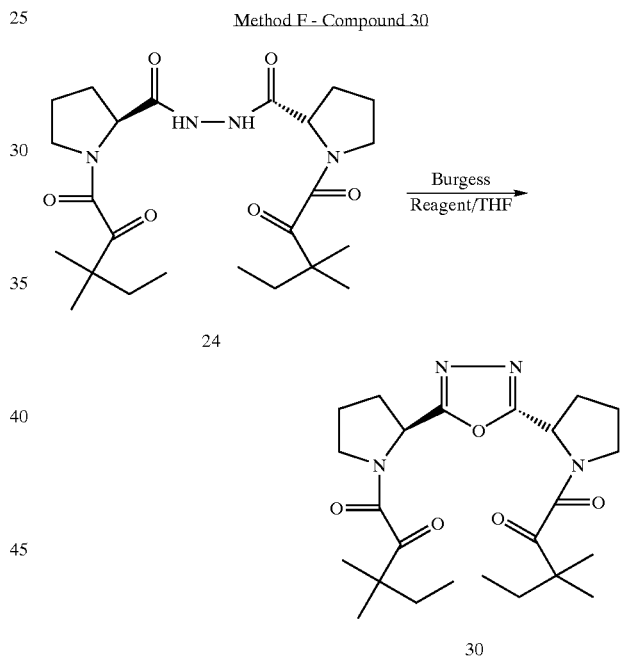

To a solution of Compound 24 (0.2018 g, 0.42 mmol) in tetrahydrofuran (10 mL) was added (methoxycarbonylsulfamoyl)-triethylamine hydroxide inner salt (Burgess Reagent, total 0.3014 g, 1.265 mmol) in three lots, each added about every 30 min. The mixture was then stirred at about RT for about 72 h. After removing the solvent in vacuo, flash chromatography of the reaction residue gave Compound 30 identical with the authentic sample as described in Method D by thin layer chromatography and mass spectral data.

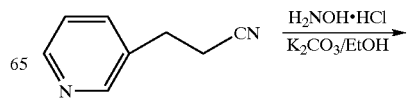

-continued

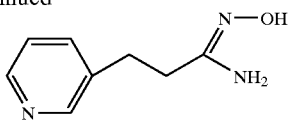

A mixture of 3-(3-pyridyl)propionitrile (7.5 g, 56.75 mM), hydroxylamine hydrochloride (5.915 g, 85.12 mM), and anhydrous potassium carbonate (15.686 g, 113.5 mM) in ethanol (200 mL) was stirred and heated to reflux under nitrogen for about 64 h. After cooling the solids were removed by filtration and the filtrates were evaporated in vacuo to dryness to obtain a viscous amber oily residue (8.95 g). Trituration in dichloromethane (300 mL) and filtration followed by the removal of dichloromethane in vacuo gave a very viscous oily residue (5.84 g). The dichloromethane-insoluble portion was dissolved in methanol, filtered and evaporated in vacuo to afford a viscous, semi-solid residue of the amidoxime (3.09 g); CIMS 166 (MH$^+$).

Compound 31

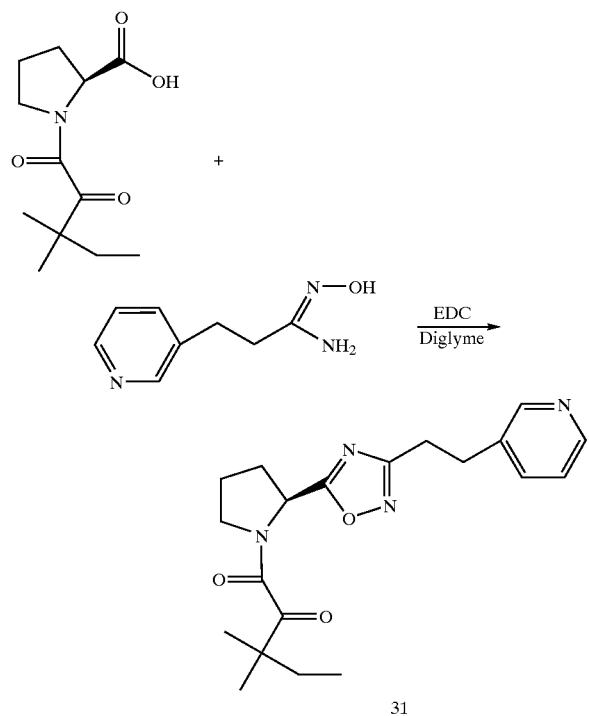

To a solution of (2S)-1-(1,2-dioxo-3,3-dimethylpentyl)-2-pyrrolidinecarboxylic acid (4.557 g, 18.89 mmol, prepared as described in WO 96/40633; 2.02 g, 8.37 mmol) in di(ethylene glycol)monomethyl ether (diglyme, 30 mL) were sequentially added the amidoxime from Reference Example 18 (1.383 g, 8.37 mM) and 1-(dimethylaminopropyl)-3-ethylcarbodiimide hydrochloride, "EDC," (3.21 g, 16.743 mmol) and the mixture stirred and heated under nitrogen in an oil bath to about 50° C. for about 20 h and then at about 110° C. for about 5 h. After cooling the reaction mixture was partitioned between water and dichloromethane, the organic layer dried (Na$_2$SO$_4$) and evaporated in vacuo to obtain a viscous residue (3.727 g). Purification by chromatography on silica gel/dichloromethane and elution with 1% methanol/ dichoromethane afforded Compound 31 as a viscous oil (0.39 g, 12.5% yield). CIMS 371 (MH$^+$). $^1$H NMR (CDCl$_3$, mixture of rotamers) δ (for the major, trans rotamer) 8.47 (s, 2H), 7.52 (d, 1H, J=7.6), 7.24–7.20 (m, 1H), 5.32 (d,d, 1H), 3.64 (t, 2H), 3.06 (M, 4H), 2.42–2.33 (m, 1H), 2.19–2.06 (m, 3H), 1.82–1.61 (m, 2H), 1.24 and 1.22 each s, each 3h), 0.87 (t, 3H). IR (KBr) cm$^{-1}$: 2970, 1704, 1645, 1580, 1425. Anal. Calcd. for C$_{20}$H$_{26}$N$_4$O$_3$: C, 64.84; H, H, 7.07; N, 15.12. Found: C, 64.43; H, 6.95; N, 14.89.

Reference Example 19

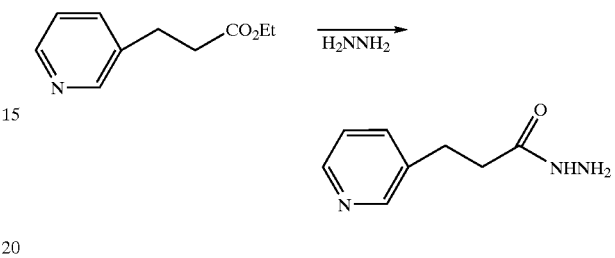

A mixture of ethyl 3-(3-pyridyl)propionate (5.92 g, 33.08 mM), anhydrous hydrazine (20 mL, a large excess) and ethanol (100 mL) was heated to reflux under nitrogen for about 18 h. The solvent was removed by evaporation in vacuo and the residue triturated with ether and refrigerated. The crystalline solid was collected and washed with a little ether to afford the hydrazide as a colorless crystalline solid, mp 87–90° C. CIMS 166 (MH+). $^1$H NMR (DMSO) δ9.04 (s, 1H), 8.43–8.39 (m, 2H), 7.61 (d, 1H), 7.32–7.28 (m, 1H), 2.83 (t, 2H), 2.35 (t, 2H). IR (KBr) cm$^{-1}$: 3325, 3231, 3004, 1667, 1630. Anal. Calcd. for C$_8$H$_{11}$N$_3$O: C, 58.17; H, 6.71; N, 25.44. Found: C, 57.94; H, 6.49; N, 25.28.

Compound 32

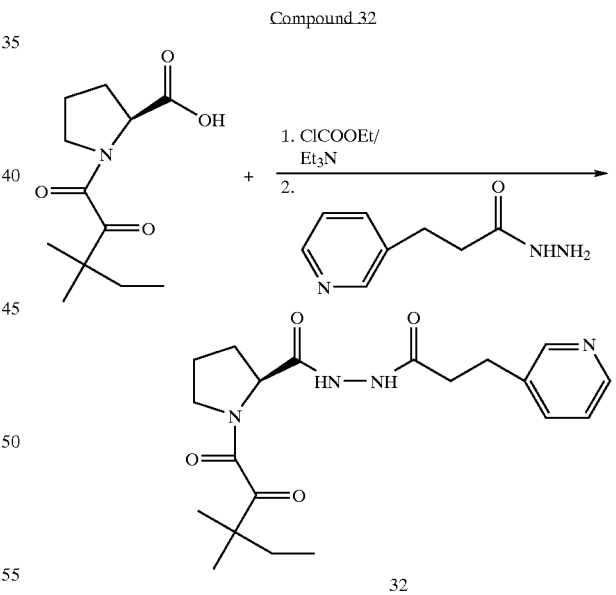

Using the procedure of Method A but utilizing one equivalent of the monoacyl hydrazine of Reference Example 19 in place of unsubstituted hydrazine, Compound 32 was obtained (73% yield) as a colorless solid, mp 90–92° C., (ether/pentane). CIMS 389 (MH$^+$). $^1$H NMR (mixture of rotamers, CDCl$_3$) δ (for the major trans rotamer) 9.3 (s, 1H), 8.83 (s, 1H), 8.44 (s, 2H), 7.54 (d, 1H), 7.27–7.18 (m, 1H), 4.59–4.56 (m, 1H), 3.48 (t, 2H), 2.99 (2H), 2.57 (t, 2H), 2.09–1.92 (m, 4H), 1.80–1.63 (m, 2H), 1.23 (s, 3H), 1.20 (s, 3H), 0.86 (t, 3H). IR (KBr) cm$^{-1}$: 3258, 2971, 1703, 1637.

Anal. Calcd. for $C_{20}H_{28}N_4O_4 \cdot 0.5H_2O$: C, 60.44; H, 7.35; N, 14.10. Found: C, 60.67; H, 7.07; N, 14.32.

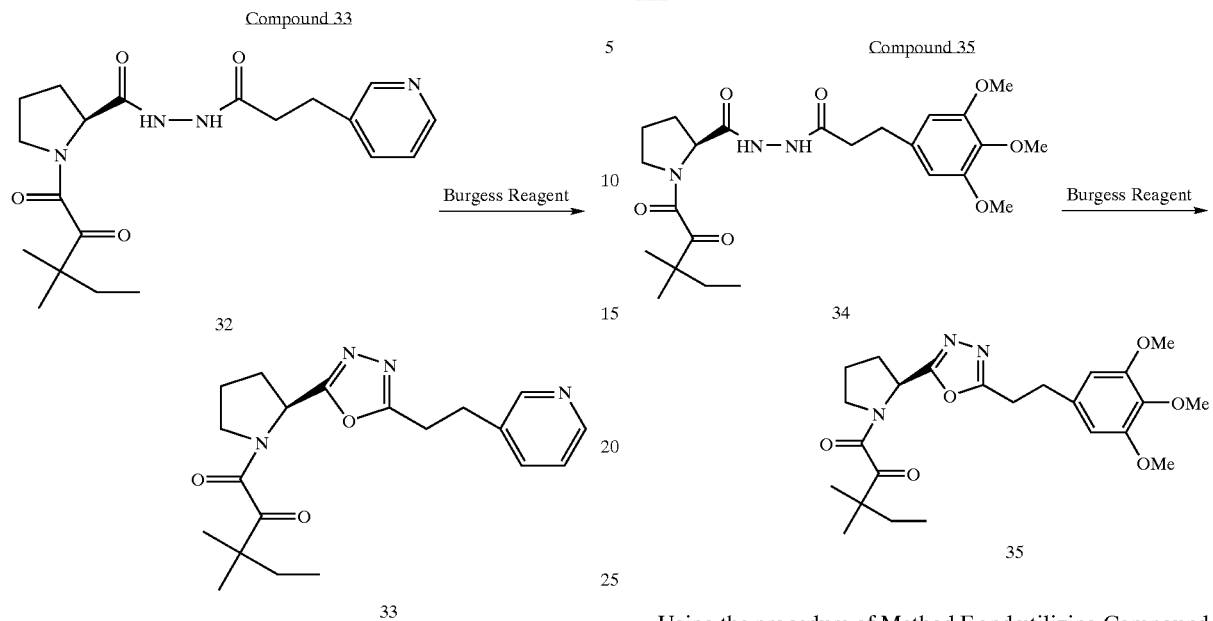

Using the procedure of Method F and Compound 32 as the substrate, Compound 33 was obtained (71.6% yield) as a colorless viscous oil. CIMS 371 (MH$^+$). $^1$H NMR (CDCl$_3$, mixture of rotamers) δ (for the major, trans rotamer) 8.49 (d, 2H), 7.54 (d, 2H), 7.26–7.22 (m, 1H), 5.30 (t, 2H), 3.15 (s, 4H), 2.35–2.04 (m, 4H), 1.77–1.59 (m, 3H), 1.23 (s, 3H), 1.21 (s, 3H), 0.86 (t, 3H). Anal Calcd. for $C_{20}H_{26}N_4O_3$: C, 64.84; H, 7.07; N, 15.12. Found: C, 64.45; H, 7.07; N, 15.12.

2.06–1.93 (m, 3H), 1.80–1.65 (m, 2H), 1.24 (s, 3H), 1.21 (s, 3H), 0.86 (t, 3H). IR (KBr) cm$^{-1}$: 3273, 2970, 1703, 1639, 1127.

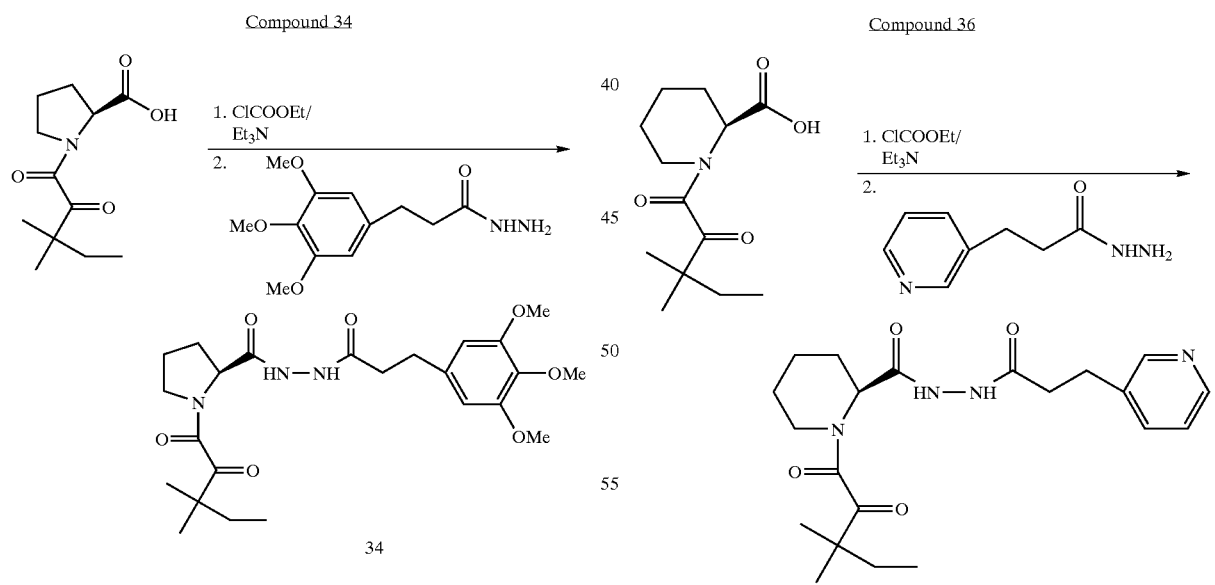

Using the procedure of Method F and utilizing Compound 34 as the substrate, Compound 35 was obtained (99% yield) as a colorless viscous oil. CIMS 460 (MH$^+$). $^1$H NMR (CDCl$_3$, mixture of rotamers) δ (for the major trans rotamer) 5.31 (d,d 1H), 3.85 (s 6H), 3.82 (s, 3H), 3.61–3.59 (m, 1H), 3.25–3.00 (m, 4H), 2.40–2.25 (m, 1H), 2.25–1.90 (m, 4H), 1.80–1.60 (m 2H), 1.23 (s, 3H), 1.21 (s, 3H), 0.86 (t, 3H). IR cm$^{-1}$: 2968, 1702, 1644, 1590, 1508, 1459, 1423, 1127. Anal Calcd. For $C_{24}H_{33}N_3O_6 \cdot 0.6H_2O$: C, 61.29; H, 7.33; N, 8.93. Found: C, 61.29; H, 7.17; N, 8.93.

Using the procedure of Method A but utilizing one equivalent of 3-(3,4,5-trimethoxyphenyl) propionylhydrazide in place of hydrazine, Compound 34 was obtained (81.4% yield) as a colorless glassy foam. CIMS 478 (MH$^+$). $^1$H NMR (CDCl$_3$, mixture of rotamers) δ (for the major, trans rotamer) 9.06 (br s, 1H), 7.99 (br s, 1H), 6.42 (s, 2H), 4.61 (m, 1H), 3.84 (s, 6H), 3.82 (s, 3H), 3.48 (t, 2H), 2.93 (t, 2H), 2.54 (t, 2H), 2.38–2.35 (m, 1H), Using the procedure of Method A with (2S)-1-(1,2-dioxo-3,3-dimethylpentyl)-2-piperidinecarboxylic acid (prepared essentially as described or (2S)-1-(1,2-dioxo-3, 3dimethylpentyl)-2-pyrrolidinecarboxylic acid in WO 96/40633) and using the hydrazide from Reference Example 19 in place of hydrazine, Compound 36 was obtained (71.5% yield) as a colorless foamy solid, mp 48–52° C. CIMS 403 (MH⁺). ¹H NMR (CDCl₃, Mixture of rotamers) δ (for the major, trans rotamer) 8.64 (s, 1H), 8.47–8.43 (m, 3H), 7.56–7.53 (m, 1H), 7.25–7.20 (m, 1H), 5.17 (d, 1H), 3.39 (d, 1H), 3.03–2.98 (m, 2H), 2.61–2.55 (m, 2H), 2.30–2.20 (m, 1H), 1.85–1.51 (m, 8H), 1.23 (s, 3H), 1.22 (s, 3H), 0.89 (t, 3H). IR (KBr) cm⁻¹: 3272, 2969, 1701, 1638, 1445. Anal. Calcd. for $C_{21}H_3ON_4O_4 \cdot 0.3H_2O$: C, 61.84; H, 7.56; N, 13.74. Found: C, 61.88; H, 7.40; N, 13.70.

Compound 37

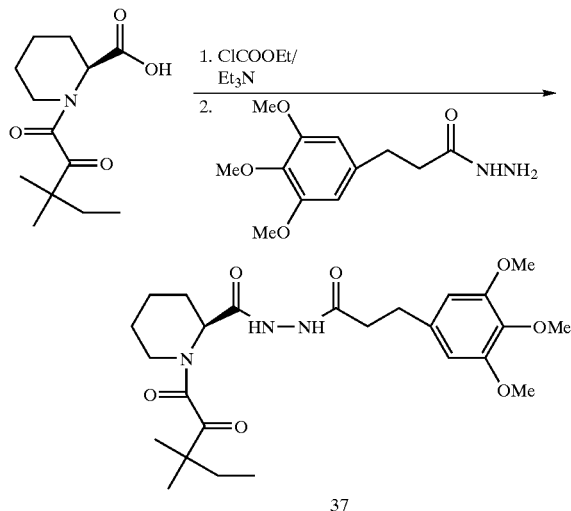

37

Utilizing the procedure of Method A with (2S)-1-(1,2-dioxo-3,3-dimethylpentyl)-2-piperidinecarboxylic acid (prepared essentially as described for (2S)-1-(1,2dioxo-3,3-dimethylpentyl)-2-pyrrolidinecarboxylic acid in WO 96/40633) and using 3-(3,4,5-trimethoxyphenyl) propionylhydrazide in place of hydrazine, Compound 37 was obtained (98% yield) as a clear glassy solid, mp 52–55° C. CIMS 492 (MH⁺). ¹H NMR (CDCl₃, mixture of rotamers) δ (for the major, trans rotamer) 8.25 (br s, 1H), 7.71 (br s, 1H), 6.43 (d, 2H), 5.17 (d, 1H), 3.85 (s, 6H), 3.83 (s, 3H), 3.38 (m, 1H), 3.0–2.90 (m, 2H), 2.50–2.40 (m, 2H), 2.33 (br t, 1H), 1.8–1.6 (m, 8H), 1.24 (s, 3H), 1.23 (s, 3H). IR (KBr) cm⁻¹: 3293, 2967, 2941, 1701, 1640, 1591, 1509, 1459, 1127. Anal. Calcd. for $C_{25}H_{37}N_3O_7$, $0.75H_2O$: C, 59.45; H, 7.68; N, 8.32. Found: C, 59.47; H, 7.55; N, 8.36.

Compound 38

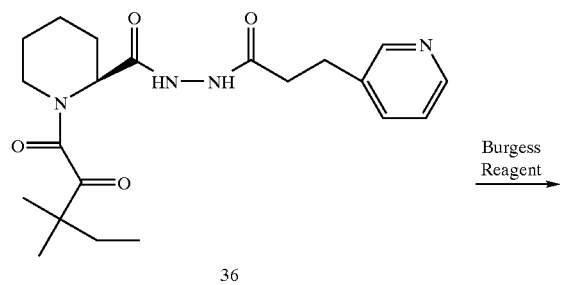

36

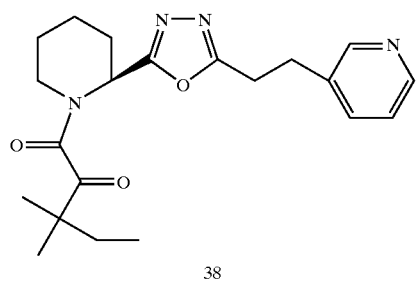

38

Utilizing the procedure of Method F and Compound 36 as the substrate, Compound 38 was obtained as a colorless oil (96% yield). CIMS 385 (MH⁺). ¹H NMR (CDCl₃, mixture of rotamers) δ (for the major, trans rotamer) 8.49 (d, 2H), 7.56 (d, 1H), 7.27–7.22 (m 2H), 5.93 (d, 1H), 3.21–3.11 (m, 4H), 2.35 (d, 1H), 2.0–1.50 (m, 8H), 1.24 (s, 3H), 1.21 (s, 3H), 0.90 (t, 3H). IR (KBr) cm⁻¹: 2967, 2942, 2877, 1700, 1644, 1585, 1434. Anal. Calcd. for $C_{21}H_{28}N_4O_3$: C, 65.60; H, 7.34; N, 14.57. Found: C, 65.37; H, 7.43; N, 14.41.

Compound 39

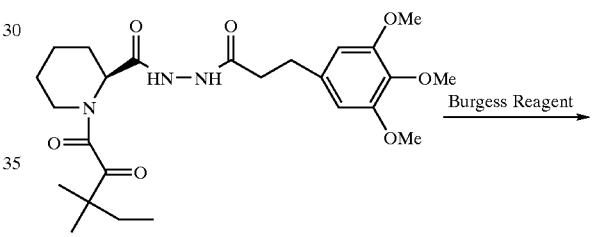

37

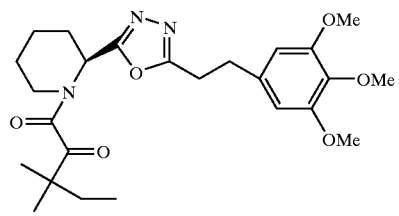

39

Utilizing the procedure of Method F and Compound 37 as the substrate, Compound 39 was obtained (64.8% yield) as a colorless viscous oil. CIMS 474 (MH⁺). ¹H NMR (CDCl₃, mixture of rotamers) δ (for the major, trans rotamer) 6.42 (s, 2H), 5.93 (d, 1H), 3.84 (s, 6H), 3.82 (s, 3H), 3.40 (br d, 1H), 3.25–3.00 (m, 4H), 2.36 (br d, 1H), 2.0–1.50 (m, 8H), 1.24 (3H), 1.22 (s, 3H), 0.90 (t, 3H). IR (KBr) cm⁻¹: 3502,2966, 2942, 1772, 1700, 1644, 1590, 1509, 1462, 1240, 1128. Anal. Calcd. for $C_{25}H_{35}N_3O_6 \cdot 2H_2O$: C, 58.92; H, 7.71; N, 8.25. Found: C, 59.05; H, 7.45; N, 8.57.

Reference Example 20

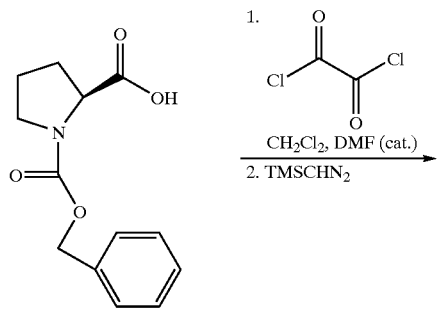

To a solution of N-carbobenzyloxy-L-proline (2.0 g, 8.0 mmol) in anhydrous methylene chloride (20 mL) at about 0° C. under $N_2$, oxalyl chloride (1.22 g, 9.6 mmol) was added dropwise, followed by 2 drops DMF. The solution was stirred for about 3 h, warmed to about 25° C. and then concentrated. The resulting acid chloride was dissolved in THF:acetonitrile (1:1, 20 mL) and treated with triethylamine (0.87 g, 8.6 mmol) at about 0° C. under $N_2$. The solution was stirred for about 10 min and trimethysilyldiazomethane (2.0M solution in hexanes, 7.8 mL) was added dropwise. The solution was stirred for about 2 h at about 0° C., warmed to about 25° C. and stirred for about an additional 17 h. The solution was diluted with ethyl acetate, washed with saturated $NaHCO_3$ and $H_2O$, dried ($MgSO_4$), and concentrated. The crude residue was purified by silica gel column chromatography, eluting with 40% ethyl acetate in pentane, to obtain the diazoketone (1.15 g, 53% yield) as a yellow-orange oil. $^1$H NMR ($CDCl_3$; mixture of cis-trans amide rotamers): δ1.88–2.09, 2.17–2.38 (2 br m, 4H); 3.58 (m, 2H), 3.81, 4.03, 4.17 (s, AB quartet, 2H, J=4.0); 4.61 (m, 1H), 5.13 (m, 2H), 7.32 (m, 5H).

Reference Example 21

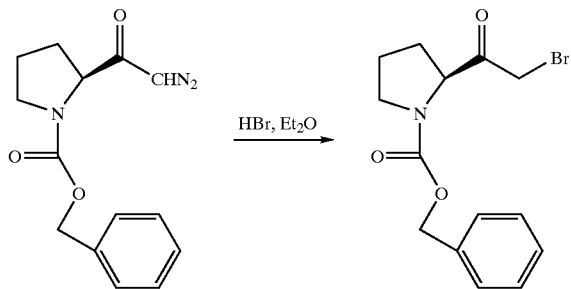

To a solution of the N-carbobenzyloxy-L-proline α-diazoketone from Reference Example 20 (1.0 g, 3.6 mmol) in anhydrous diethyl ether (10 mL) under $N_2$, a saturated solution of HBr in diethyl ether was added dropwise until $N_2$ evolution ceased. The solution was stirred for about 1 h at about 25° C., then was washed with saturated $NaHCO_3$, $H_2O$ and saturated NaCl, dried ($MgSO_4$) and concentrated. The crude material was purified by silica gel column chromatography and eluted with 40% ethyl acetate in pentane to obtain the bromoketone (0.49 g, 42% yield) as a clear oil. $^1$H NMR ($CDCl_3$; mixture of cis-trans amide rotamers): δ1.84–2.30 (br m, 4H); 3.58 (m, 2H); 4.32 (m, 1H); 5.17 (m, 2H); 5.28 (t, 1H); 7.35 (m, 5H).

Compound 40

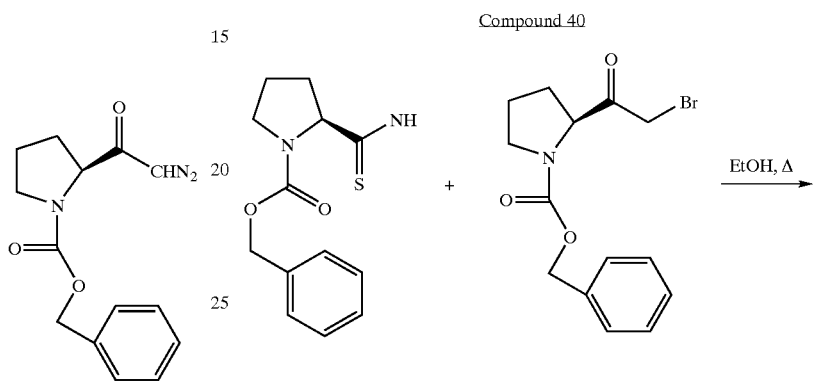

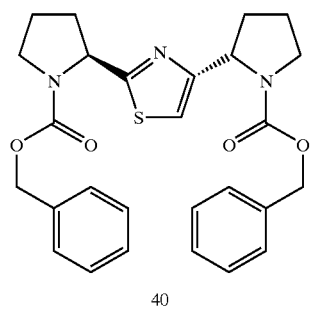

40

To a solution of the thioamide from Reference Example 8 (0.40 g, 1.5 mmol) in anhydrous ethanol (15 mL), the N-carbobenzyloxy-L-proline α-bromomethyl ketone from Reference Example 21 (0.49 g, 1.5 mmol) in anhydrous ethanol (2 mL) was added dropwise. The resulting solution was heated to reflux under $N_2$ for about 3 h. The solution was cooled to about 25° C. and concentrated. The resulting residue was taken up in diethyl ether/saturated $NaHCO_3$. The aqueous phase was separated and extracted several times with diethyl ether. The organic layers were combined, dried ($MgSO_4$) and concentrated. The crude material was purified by silica gel column chromatography and eluted with 40% ethyl acetate in pentane to obtain Compound 40 (0.51 g, 69% yield) as a clear oil. $^1$H NMR ($CDCl_3$; mixture of cis-trans amide rotamers): δ1.93 (m, 4H); 2.20 (br m, 4H); 3.61 (br m, 4H); 5.18 (br m, 6H); 6.74, 6.85 (s,s, 1H); 7.13 (m, 2H); 7.27 (m, 4H); 7.39 (m, 4H).

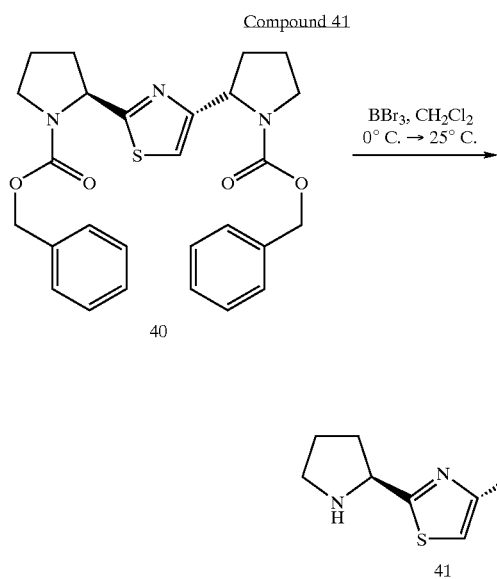

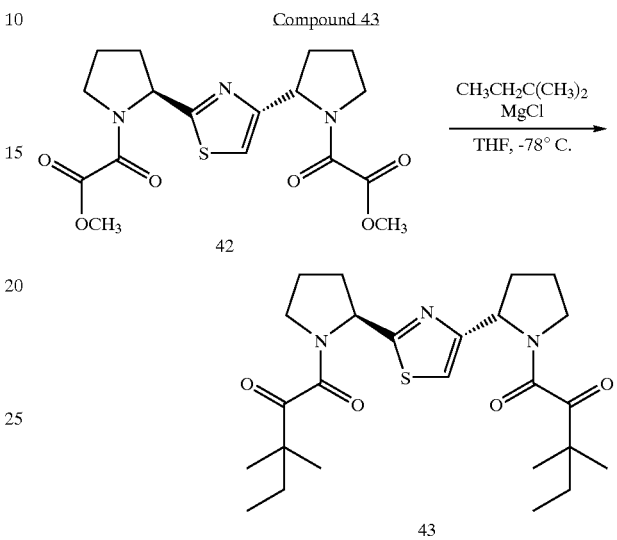

To a solution of Compound 40 (0.48 g, 0.97 mmol) in anhydrous methylene chloride (20 mL) at about 0° C., a 1.0M solution of BBr₃ in methylene chloride (5 mL) was added dropwise. The solution was stirred for about 1 h at about 0° C., then was warmed to about 25° C. and stirred for about 2 h. The reaction was terminated by dropwise addition of H₂O (25 ml). The layers were separated and the organic phase was extracted with H₂O. The combined aqueous phases were adjusted to about pH 11 by dropwise addition of 1N NaOH and then concentrated. The resulting salts were filtered and exhaustively washed with ethyl acetate. The organic filtrate was dried (MgSO₄) and concentrated to yield Compound 41 (0.067 g, 31% yield) as a yellow oil. ¹H NMR (CDCl₃): δ1.88 (m, 6H); 2.17 (m, 1H); 2.31 (m, 1H); 3.05 (m, 2H); 3.16 (m, 2H); 4.24 (m, 1H); 4.57 (m, 1H); 6.99 (s, 1H).

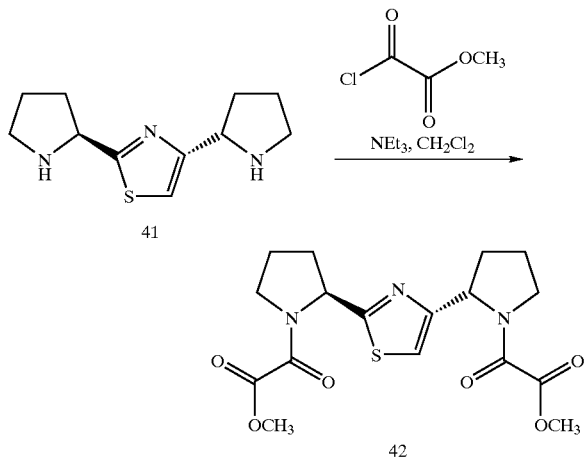

To a solution of Compound 41 (0.067 g, 0.30 mmol) in anhydrous methylene chloride (5 mL) was added triethylamine (0.13 g, 1.28 mmol) at about 0° C. After stirring for about 15 min, a solution of methyl oxalyl chloride (0.10 g, 0.84 mmol) in methylene chloride (2 mL) was added dropwise. The solution was stirred for about 1.5 h at about 0° C. then was washed with H₂O, dried (MgSO₄), and concentrated to yield Compound 42 (0.115 g, 97% yield) as a yellow oil. ¹H NMR (CDCl₃; mixture of 4 cis-trans amide rotamers) δ1.96–2.48 (overlapping series of br m's, 8H); 3.62–4.00 (series of overlapping br m's, 4H); 3.67, 3.72, 3.76, 3.91 (2 overlapping s, s, s, series of overlapping s, 6H); 5.44, 5.71 (br m, 2H); 6.91, 6.93, 6.98, 7.07 (s, s, s, s, 1H).

To a solution of Compound 42 (0.115 g, 0.29 mmol) in anhydrous THF (5 mL) at about −78° C., dimethylpropylmagnesium chloride (1.0M solution in diethyl ether, 0.754 mL) was added dropwise. The solution was stirred for about 3 h at about −78° C., then was poured into saturated ammonium chloride (25 mL), and extracted with ethyl acetate. The organic phases were combined, dried (MgSO₄), and concentrated. The crude residue was purified by silica gel column chromatography, eluting with 40% ethyl acetate in pentane, to obtain Compound 43 (0.075 g, 55% yield) as a white solid, mp 127–129° C. ¹H NMR (CDCl₃; mixture of cis-trans amide rotamers) δ0.60–1.02 (series of overlapping s and m, 10H); 1.12–1.21 (series of overlapping s, 8H); 1.66 (m, 4H); 1.88–2.29 (overlapping br m's, 8H); 3.38–3.70 (br m, 4H); 5.15, 5.29, 5.37, 5.42 (m, m, m, m, 2H); 6.81, 6.84, 6.91, 6.96 (s, s, s, s, 1H). Anal Calcd. For C₂₅H₃₇N₃O₄S: C, 63.13; H, 7.84; N, 8.83. Found: C, 62.94; H, 7.80; N, 8.67.

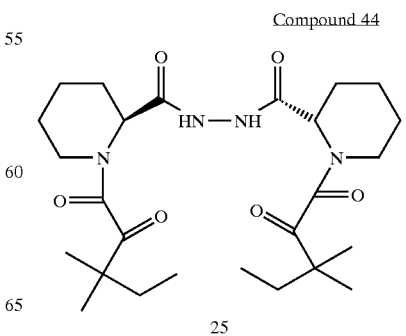

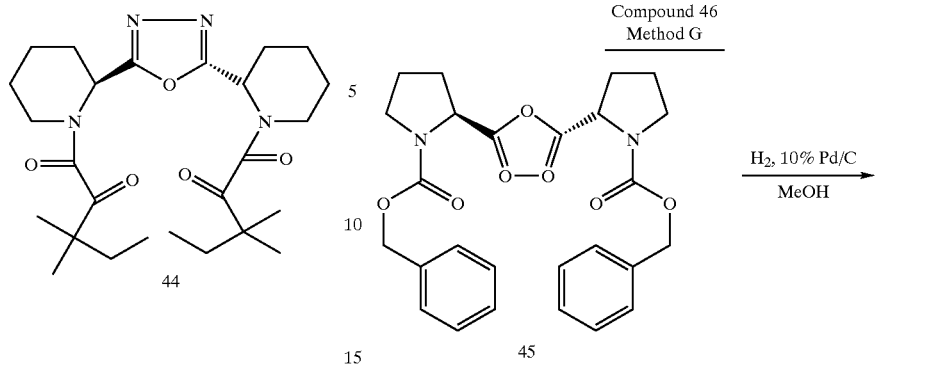

Utilizing the procedure of Method F with Compound 25 as the substrate, Compound 44 (63% yield) was obtained as a colorless solid, mp 102–105° C. (ether/pentane). CIMS 489 (MH$^+$). $^1$H NMR (CDCl$_3$, mixture of rotamers) δ (for the major, trans rotamer) 5.98 (d, 2H), 3.46–3.17 (m, 4H), 2.33 (d, 2H), 1.94–1.40 (m, 12H), 1.25 and 1.21 (each s, each 6H), 0.87 (t, 6H). IR (KBr) cm$^{-1}$: 1702, 1639, 1578, 1550, 1441. Anal. Calcd. for C$_{26}$H$_{40}$N$_4$O$_5$·0.6H$_2$O: C, 62.53; H, 8.32; N, 11.22. Found : C, 62.52; H, 8.09; N, 11.14.

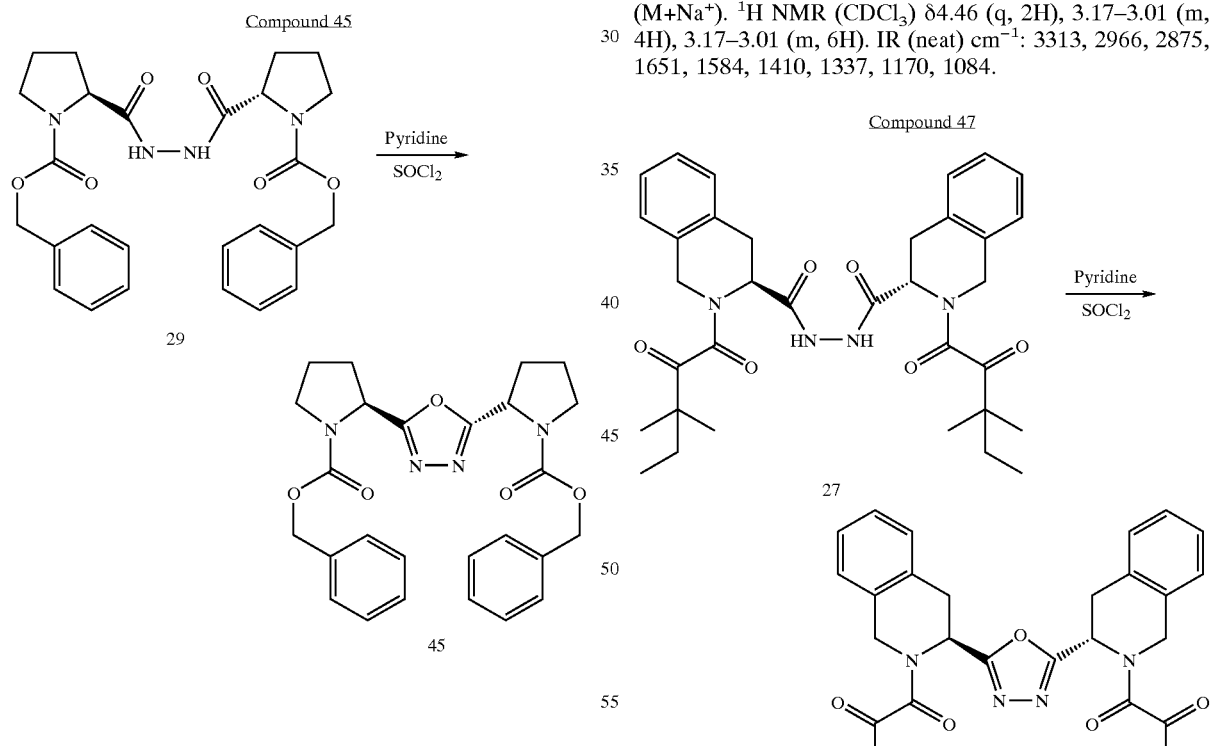

Utilizing the procedure of Method D with Compound 29 as the substrate, Compound 45 (68% yield) was obtained as a viscous oil; [α]=–87.4° (CHCl$_3$). CIMS 477 (MH$^+$), 499 (M+Na$^+$). $^1$H NMR (CDCl$_3$, mixture of rotamers) δ (for the major trans rotamer) 7.35–7.19 (m, 10H), 5.20–5.0 (m, 6H), 3.80–3.40 (m, 4H), 2.40–1.85 (m, 8H). IR (KBr) cm$^{-1}$: 3584, 2956, 1705, 1584, 1498, 1446, 1410, 1355. Anal. Calcd. for C$_{26}$H$_{28}$N$_4$O$_5$·0.25H$_2$O: C, 64.92; H, 5.97; N, 11.65. Found: C, 64.92; H, 5.88; N, 11.81.

A solution of Compound 45 (3.06 g, 6.46 mmol) in methanol (125 mL) was hydrogenated over 10% Pd/C catalyst (580 mg) at about 15 psi for about 4 h. The catalyst was removed by filtration through a pad of Celite and the filtrates evaporated to dryness in vacuo to obtain a colorless, very viscous oil (1.28 g, 95% yield). CIMS 209 (MH$^+$), 231 (M+Na$^+$). $^1$H NMR (CDCl$_3$) δ4.46 (q, 2H), 3.17–3.01 (m, 4H), 3.17–3.01 (m, 6H). IR (neat) cm$^{-1}$: 3313, 2966, 2875, 1651, 1584, 1410, 1337, 1170, 1084.

Utilizing the procedure of Method D with a large excess of pyridine and thionyl chloride (22 and 11 equivalents, respectively) and Compound 27 as the substrate, Compound 47 (80% yield) was obtained as a colorless foamy material, [α]=–55.12° (c=0.254, CHCl$_3$). CIMS 585 (MH$^+$). $^1$H NMR (CDCl₃, mixture of rotamers) δ (for the major trans rotamer) 7.22–6.91 (m, 8H), 6.15–6.10 (m, 2H), 4.41(m, 2H), 3.45–3.20 (m, 4H), 1.81–1.69 (m, 4H), 1.25 and 1.22 (each s, each 6H), 0.90 (t, 6H). IR(KBr) cm⁻¹: 2969, 2928, 2879, 1702, 162, 1586, 1556, 1499, 1429. Anal. Calcd. for $C_{34}H_{42}N_4O_5 \cdot 0.5C_5H_{12}$: C, 70.76; H, 7.58; N, 8.92. Found: C, 70.93; H, 7.38; N, 8.92.

Compound 48
Method H

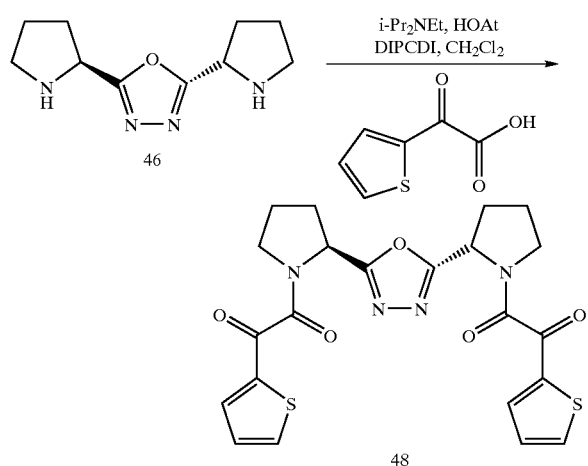

To a solution of Compound 46 (0.107 g, 0.514 mmol) in dichloromethane (10 mL), diisopropylethylamine (2.87 mL, 1.65 mmol), diisopropylcarbodiimide (0.323 mL), 1-hydroxy-7-azabenzotriazole (0.280 g, 2.06 mmol) and thiophene-2-glyoxylic acid (0.320 g, 2.056 mmol) in dichloromethane (5 mL) were sequentially added. The mixture was stirred under argon at about RT for about 20 h. The mixture was evaporated to dryness in vacuo, the residue taken up in dichloromethane (20 mL) and then washed successively with 5% aqueous hydrochloric acid, water and saturated sodium bicarbonate solution. The organic layer was dried (Na₂SO₄), filtered and evaporated to dryness to give a residue. This crude product was purified by column chromatography on silica gel eluting with 1.5% methanol in dichloromethane to obtain Compound 48 (65% yield) as a foamy solid, mp 74–76° C. CIMS 485 (MH⁺), 507 (M+Na⁺). ¹H NMR (CDCl₃, mixture of rotamers) δ (for the major trans rotamer) 8.05–7.96 (m, 2H), 7.81–7.74 (m, 2H), 7.21–7.11 (m, 2H), 5.46–5.42 (m, 2H), 3.87–3.66 (m, 4H), 2.47–1.99 (m, 8H). IR (KBr) cm⁻¹: 3092, 2955, 2310, 1658, 1584, 1561, 1513, 1441, 1406, 1353, 1252, 1167. Calcd. for $C_{22}H_{20}N_4O_5S_2$: C, 54.53; H, 4.16; N, 11.56. Found: C, 54.49; H, 4.08; N, 11.34.

Compound 51
Method I

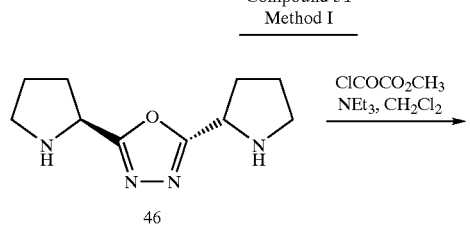

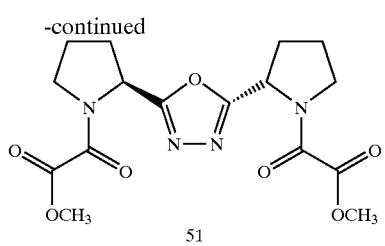

To an ice cold, stirred solution of Compound 46 (0.431 g, 2.071 mmol) and triethylamine (0.65 mL, 4.66 mmol) in dichloromethane (20 mL) under argon was added methyl chlorooxoacetate (0.54 mL, 5.8 mmol) in dichloromethane (9 mL) over about a 30 min period. After stirring the mixture at about 0° C. for about an additional 2 h, the reaction mixture was worked-up by washing with brine (3×50 mL), drying the organic layer (Na₂SO₄), filtering and evaporating to dryness in vacuo to obtain Compound 51 as a foam (0.815 g, 5% yield). CIMS 381 (MH⁺), 403 (M+Na⁺).

Compound 49

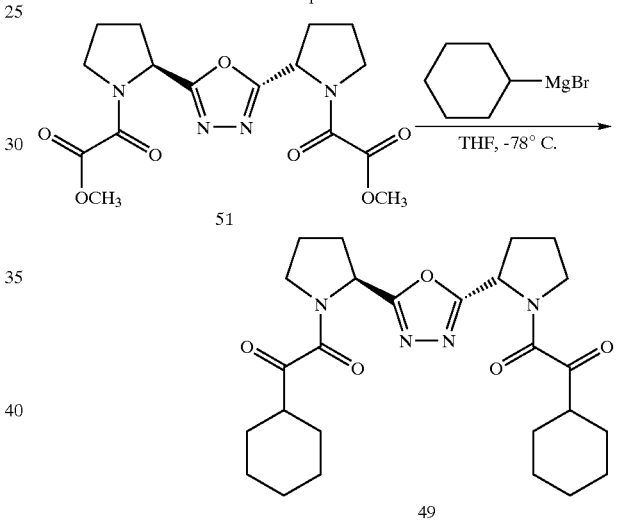

To a solution of Compound 51 (0.375 g, 0.986 mmol) in tetrahydrofuran (7 mL), stirred and cooled under argon at about −78° C., an ether solution of cyclohexylmagnesium bromide (1 mL of 2M, 2 mmol) was added dropwise over about a 15 min period. After further stirring at about −78° C. for about 3 h, the reaction mixture was worked-up by pouring into saturated aqueous ammonium chloride solution and extracting with ethyl acetate, drying the organic layer (Na₂SO₄), filtering and evaporating to dryness in vacuo. The crude product obtained was purified by column chromatography on silica gel eluting with 0.75% methanol in dichloromethane to afford Compound 49 (29 mg, 5.8% yield) as a colorless solid, mp 132–133° C. CIMS 485 (MH⁺), 507 (M+Na⁺). ¹H NMR (CDCl₃, mixture of rotamers) δ (for the major trans rotamer) 5.33–5.27 (m, 2H), 3.88–3.59 (m, 4H), 2.44–1.69 (m, 20H), 1.38–1.00 (m, 6H). IR (KBr) cm⁻¹: 2880, 2927, 2852, 1706, 1641, 1582, 1560, 1445. Anal. Calcd. for $C_{26}H_{36}N_4O_5 \cdot 0.35H_2O$: C, 63.61; H, 7.54; N, 11.41. Found: C, 63.96; H, 7.59; N, 11.08.

Compound 50

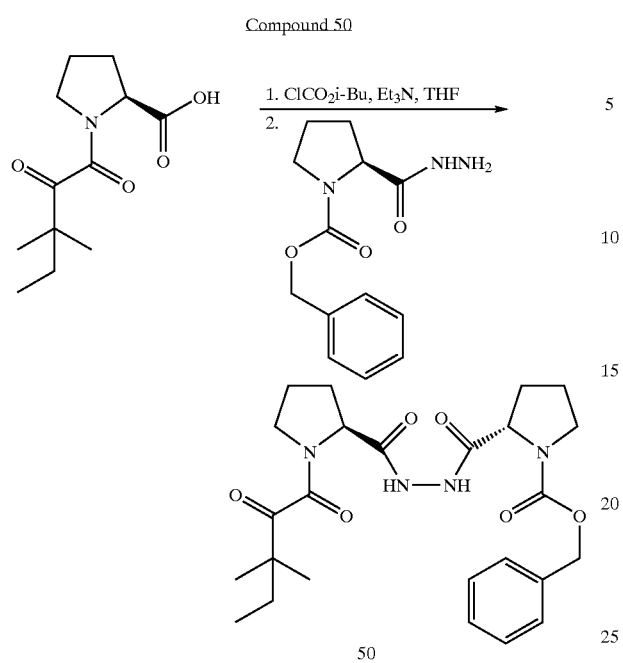

Utilizing the procedure of Method A, but with one equivalent of N-carbobenzyloxyproline acid hydrazide (CAS #53157-63-4) in place of hydrazine, Compound 50 was obtained as a colorless solid (56% yield), mp 145–146° C. CIMS 443 (MH$^+$ —CO), 487 (MH$^+$), 485 (M–H). [α]=−96.1° (c=0.254, CHCl$_3$). $^1$H NMR (CDCl$_3$, mixture of rotamers) δ (for the major trans rotamer): 9.05 (br s, 1H), 8.98 (br s, 1H), 7.36 (s, 5H), 5.23–5.11 (m, 2H), 3.70–3.40 (m, 4H), 2.41 (br s, 2H), 2.30–1.80 (m, 6H), 1.79–1.42 (m, 2H), 1.25 and 1.22 (each s, each 3H), 0.87 (t, 3H). IR (KBr) cm$^{-1}$: 3307, 3272, 2966, 2884, 1731, 1699, 1651, 1444. Anal. Calcd. for C$_{25}$H$_{34}$N$_4$O$_6$: C, 61.71; H, 7.04; N, 11.51. Found: C, 62.09; H, 7.20; N, 11.28.

Compound 52

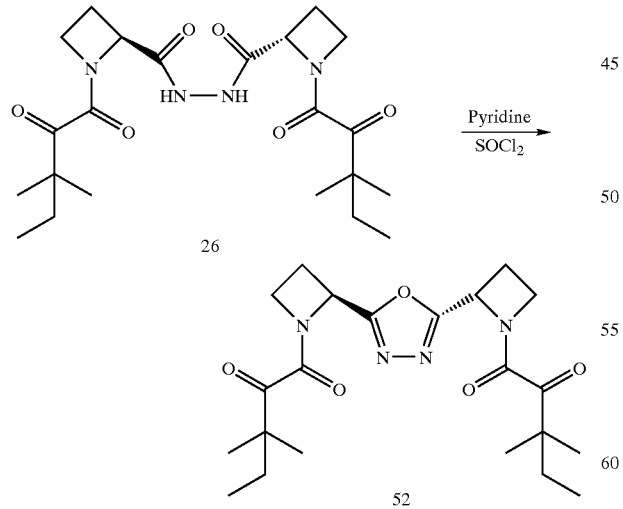

Utilizing the procedure of Method D with Compound 26 as the substrate, Compound 52 was obtained as a colorless, viscous, greasy material (75.8% yield). CIMS 433 (MH$^+$), 455 (M+Na$^+$). $^1$H NMR (mixture of rotamers, CDCl$_3$) δ (for the major trans rotamer) 5.86–5.53 (d, 2H), 4.48–4.35 (m, 2H), 4.27–4.14 (m, 2H), 2.93–2.80 (m, 2H), 2.73–2.50 (m, 2H), 1.84–1.60 (m, 4H), 1.21 (s, 12H), 0.82 (t, 6H). IR (KBr) cm$^{-1}$: 2970, 2880, 1704, 1651, 1583, 1564, 1461, 1423, 1385.

Compound 53

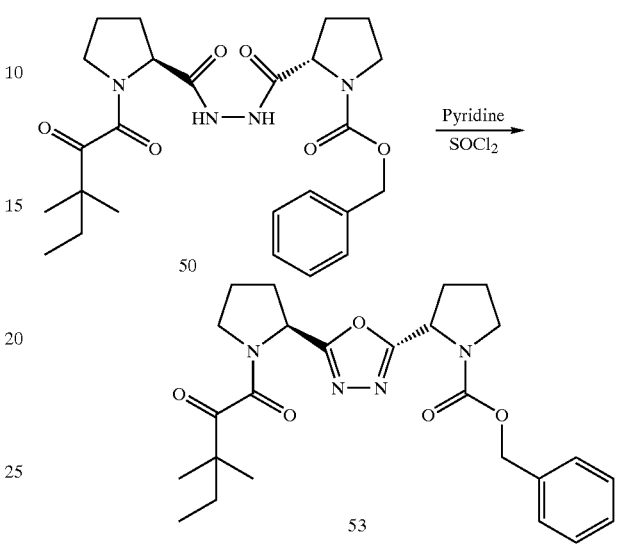

Utilizing the procedure of Method D with Compound 50 as the substrate, Compound 53 was obtained as a colorless viscous oil (89% yield). CIMS 469 (MH$^+$), 491 (M+Na$^+$). [α]=−92.7° (c=0.246, CHCl$_3$). $^1$H NMR (CDCl$_3$, mixture of rotamers) δ (for the major trans rotamer) 7.36–7.20 (m, 5H), 5.20–5.03 (m, 2H), 3.70–3.50 (m, 2H), 2.40–1.80 (m, 4H), 1.80–1.60 (m, 2H). IR (neat) cm$^{-1}$: 2968, 2881, 1702, 1641, 1584, 1411, 1356. Anal. Calcd. for C$_{25}$H$_{32}$N$_4$O$_5$: C, 64.09; H, 6.88; N, 11.96. Found: C, 64.20; H, 6.87; N, 11.83.

Compound 54

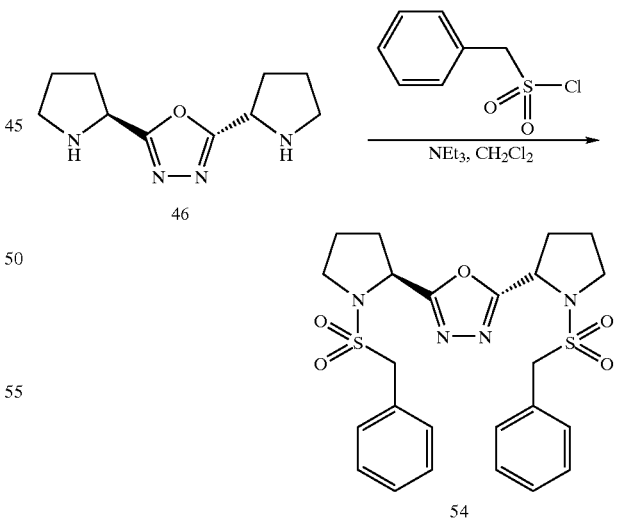

Utilizing the procedure of Method I, but with α-toluenesulfonyl chloride in place of methyl chlorooxoacetate, Compound 54 (59% yield) was obtained as a colorless solid, mp 144–145° C. CIMS 517 (MH$^+$), 539 (M+Na$^+$). $^1$H NMR (CDCl$_3$, mixture of rotamers) δ (for the major trans rotamer) 7.49–7.46 (m, 4H), 7.40–7.37 (m, 6H), 5.04 (q, 2H), 4.41 (q, 4H), 3.39–3.31 (9 m, 2H), 3.14–3.07 (m, 2H), 2.33–2.12 (m, 4H), 2.09–1.94 (m, 4H). IR (KBr) cm$^{-1}$: 1574, 1554, 1495, 1455, 1410, 1332, 1140. Anal Calcd. for: $C_{24}H_{28}N_4O_5S_2$: C, 55.80; H, 5.46; N, 10.84. Found: C, 55.73; H, 5.42; N, 10.76.

Compound 55

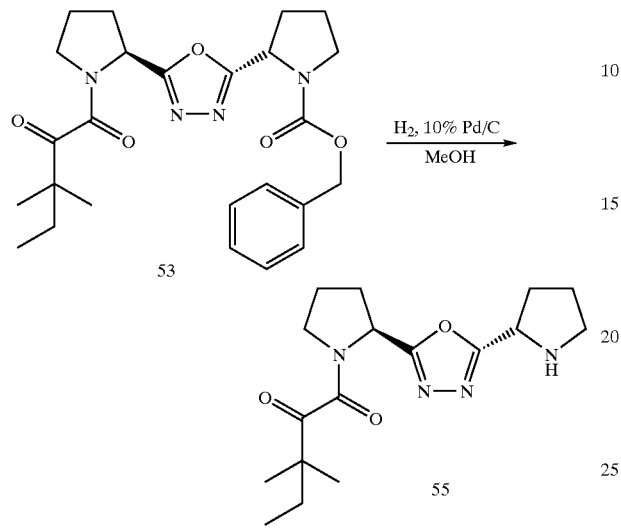

Utilizing the procedure of Method G with Compound 53 as the substrate, Compound 55 was obtained as a colorless viscous oil (90% yield). [α]=–35.5° (c=0.414, CHCl$_3$). CIMS 335 (MH$^+$), 357 (M+Na$^+$). $^1$H NMR (CDCl$_3$, mixture of rotamers) δ (for the major trans rotamer) 5.32 (dd, 2H), 4.46 (m, 2H), 3.61 (dt, 4H), 3.36–3.03 (m, 4H), 2.40–1.60 (m, 6H), 1.24 and 1.21 (each s, each 3H), 0.86 (t, 3H). IR (neat) cm$^{-1}$: 3342, 2969, 2880, 1703, 1642, 1586, 1586, 1428. Anal Calcd. for $C_{17}H_{26}N_4O_3$: C, 61.06; H, 7.84; N, 16.75. Found: C, 60.75; H, 7.64; N, 16.68.

Compound 56

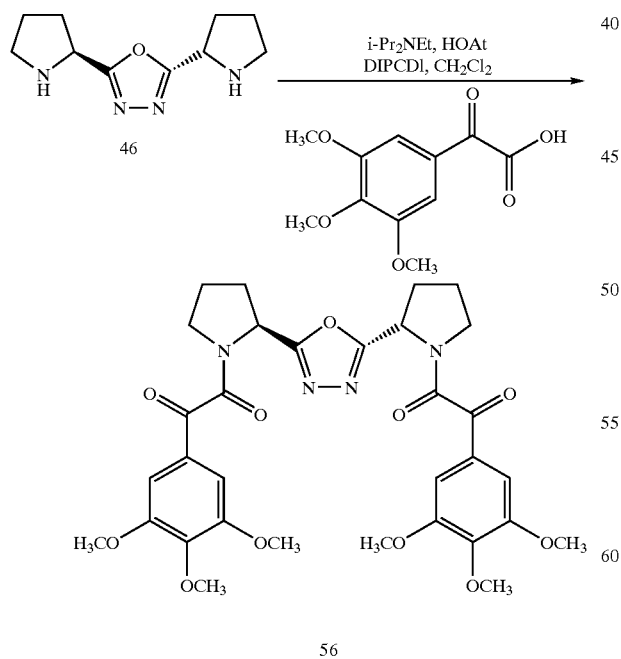

Utilizing the procedure of Method H, but with 3,4,5-trimethoxyphenylglyoxylic acid in place of thiophene-2-glyoxylic acid, Compound 56 was obtained as a colorless solid, mp 79–83° C. (56% yield). [α]=–0.90 (c=0.260, CHCl$_3$). CIMS 653 (MH$^+$), 675 (M+Na$^+$). $^1$H NMR (CDCl$_3$, mixture of rotamers) δ (for the major trans rotamer) 7.34 (s, 4H), 5.41 (d,d, 2H), 3.95 (s, 6H), 3.93 (s, 12H), 3.68 (t, 4H), 3.48–2.20 (m, 8H). IR (KBr) cm$^{-1}$: 2944, 2839, 1770, 1715, 1677, 1650, 1583, 1416, 1330, 1126. Anal. Calcd. for $C_{32}H_{36}N_4O_{11}$: C, 58.89; H, 5.56; N, 8.58. Found: C, 58.64; H, 5.75; N, 8.35.

Compound 57

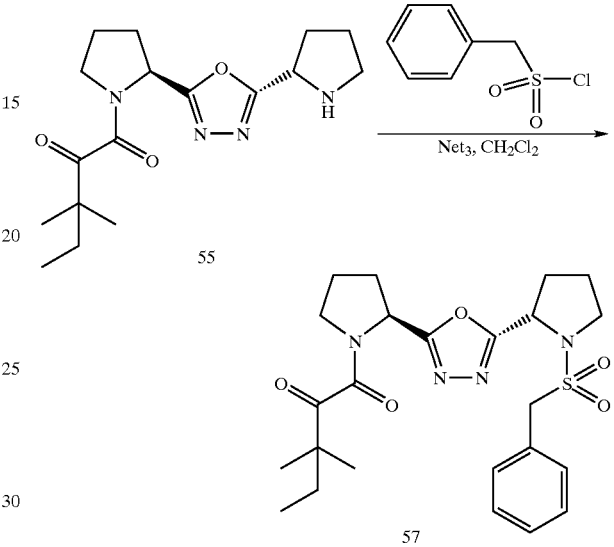

Utilizing the procedure of Method I, but with Compound 55 as the substrate and with α-toluenesulfonyl chloride in place of methyl chlorooxoacetate, Compound 57 was obtained as a viscous oil (72% yield). [α]=–28.6° (c=0.49, CHCl$_3$). CIMS 489 (MH$^+$), 511 (M+Na$^+$). $^1$H NMR (CDCl$_3$, mixture of rotamers) δ (for the major trans rotamer) 7.49–7.46 (m, 2H), 7.38–7.36 (m, 4H), 5.39–5.32 (m, 1H), 5.10–5.06 (m, 1H), 4.39 (q, 2H), 3.71–3.58 (m, 2H), 3.40–3.31 (m, 1H), 3.11–3.00 (m, 1H), 2.38–1.92 (m, 9H), 1.79–1.59 (m, 2H), 1.23 and 1.20 (each s, each 3H), 0.84 (t, 3H). IR (Neat) cm$^{-1}$: 2971, 2881, 1703, 1644, 1584, 1562, 1427, 1342. Anal. Calcd. for $C_{24}H_{32}N_4O_5S$: C, 59.00; H, 6.60; N, 11.47. Found: C, 59.24; H, 6.58; N, 11.39.

Compound 58

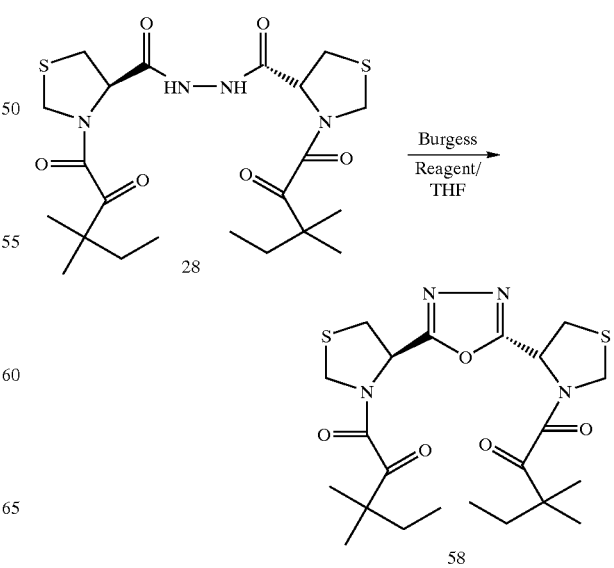

Utilizing the procedure of Method F with Compound 28 as the substrate, Compound 58 was obtained (44% yield) as a colorless viscous oil. [α]=−12° (c=0.308, CHCl₃). CIMS 497 (MH⁺), 519 (M+Na⁺). ¹H NMR (CDCl₃, mixture of rotamers) δ (for the major trans rotamer) 5.90–5.83 (m, 2H), 4.644.48 (m, 4H), 3.53–3.34 (m, 4H), 1.74 (m, 4H), 1.26 and 1.23 (each s, each 6H), 0.88 (t, 6H); IR cm⁻¹ 2966, 1798, 1651. Anal. Calcd. for $C_{22}H_{32}N_4O_5S_2$: C, 53.20; H, 6.49; N, 11.28. Found: C, 53.36; H, 6.58; N, 10.64.

Compound 59

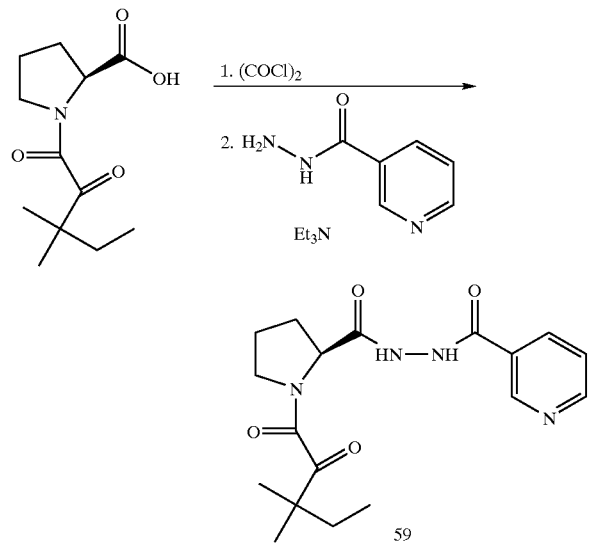

Utilizing the procedure of Method C, but with (2S)-1-(1,2-dioxo-3,3-dimethylpentyl)-2-pyrrolidinecarboxylic acid (prepared as described in WO 96/40633) in place of (4R)-3-(1,2-dioxo-3,3-dimethylpentyl)-4-thiazolidinecarboxylic acid and nicotinic hydrazide in place of hydrazine, Compound 59 was obtained as a colorless solid, mp 161–163° C. (42% yield). CIMS 361 (MH⁺), 383 (M+Na⁺). ¹H NMR (CDCl₃) δ9.06 (d, 1H), 8.74 (m, 1H), 8.14 (d, 1H), 7.37 (m, 1H), 4.68 (m, 1H), 3.52 (t, 2H), 2.39 (m, 1H), 2.14 (m, 2H), 2.00 (m, 1H), 1.81–1.61 (m, 4H). IR (KBr) cm⁻¹: 3296, 2965, 2883, 1702, 1664, 1640, 1590, 1518. Anal. Calcd. for $C_{18}H_{24}N_4O_4$: C, 59.99; H, 6.71; N, 15.55. Found: C, 59.88; H, 6.63; N, 15.38.

Compound 60

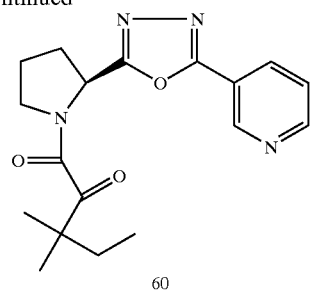

Utilizing the procedure of Method F with Compound 59 as the substrate, Compound 60 was obtained as a colorless solid (79% yield), mp 96–97° C. CIMS 343 (MH⁺), 365 (M+Na⁺). ¹H NMR (CDCl₃, mixture of rotamers) δ (for the major trans rotamer) 9.25 (d, 1H), 8.78 (m, 1H), 8.34 (dd, 1H), 7.47 (m, 1H), 5.43 (d,d, 1H), 3.67 (t, 2H), 2.47–2.08 (m, 2H), 1.85–1.73 (m, 2H), 1.26 and 1.23 (each s, each 3H), 0.87 (t, 3H). IR (KBr) cm⁻¹: 2969, 2883, 1701, 1638, 1431. Anal. Calcd. for $C_{18}H_{22}N_4O_3$: C, 63.14; H, 6.48; N, 16.36. Found: C, 62.91; H, 6.37; N, 16.27.

Compound 61

Utilizing the procedure of Method A with (2S)-1-(1,2-dioxo-3,3-dimethylbutyl)-2-pyrrolidinecarboxylic acid (prepared essentially as described for (2S)-1-(1,2-dioxo-3,3-dimethylpentyl)-2-pyrrolidinecarboxylic acid in WO 96/40633) as the substrate, Compound 61 was obtained as a colorless solid (28% yield), mp 108–110° C. CIMS 451 (MH⁺), 473 (M+Na⁺), 449 (M−H). [α]=−116.1° (c=0.274, CHCl₃). ¹H NMR (CDCl₃, mixture of rotamers) δ (for the major trans rotamer) 9.11 (s, 2H), 4.62 (m, 2H), 3.47 (t, 4H), 2.50–2.37 (m, 2H), 2.15–1.85 (m, 4H), 1.29 (s, 18H). IR (KBr) cm⁻¹: 3279, 2976, 2879, 1707, 1639, 1446. Anal. Calcd for $C_{22}H_{34}N_4O_6 \cdot 0.35H_2O$: C, 57.84; H, 7.66; N, 12.26. Found: C, 58.10; H, 7.75; N, 11.98.

Compound 61

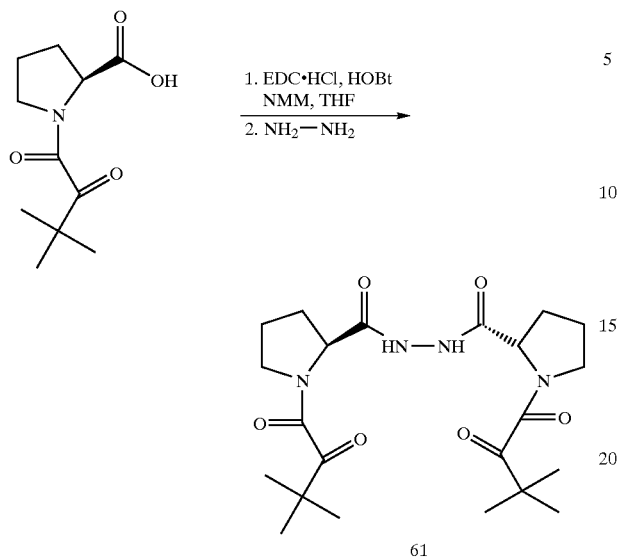

Utilizing the procedure of Method B with (2S)-1-(1,2-dioxo-3,3-dimethylbutyl)-2-pyrrolidinecarboxylic acid (prepared essentially as described for (2S)-1-(1,2-dioxo-3,3-dimethylpentyl)-2-pyrrolidinecarboxylic acid in WO 96/40633) as the substrate and using N-methylmorpholine (NMM) as a base in place of triethylamine, "Et$_3$N," Compound 61 was obtained (73% yield), identical in all respects with that obtained by Method A.

Compound 62

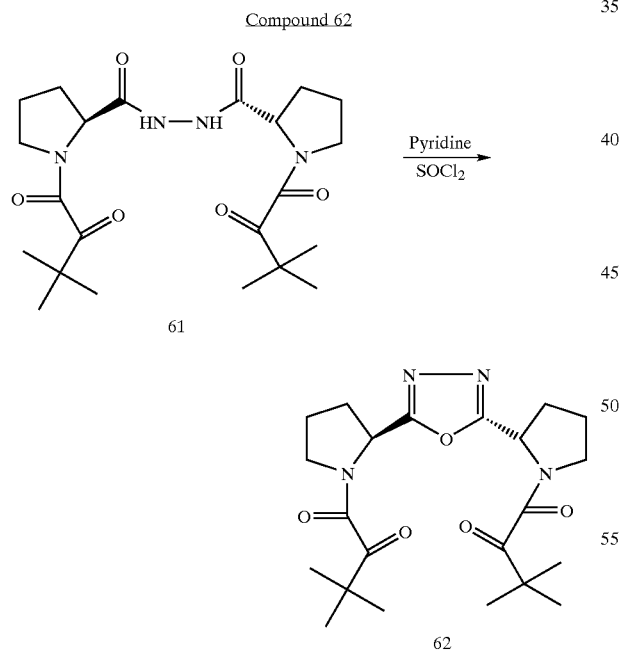

Utilizing the procedure of Method D with Compound 61 as the substrate, Compound 62 was obtained (42.5% yield), mp 138–141° C. [α]=−82.5° (c=0.282, CHCl$_3$). $^1$H NMR (CDCl$_3$, mixture of rotamers) δ (for the major trans rotamer) 5.34–5.29 (m, 2H), 3.63–3.55 (m, 4H), 2.40–2.00 (m, 8H), 1.27 (s, 18H). IR (KBr) cm$^{-1}$: 2958, 1705, 1636, 1582, 1560, 1438. Anal. Calcd. for C$_{22}$H$_{32}$N$_4$O$_5$: C, 61.09; H, 7.46; N, 12.95. Found: C, 61.05; H, 7.44; N, 12.88.

Compound 62

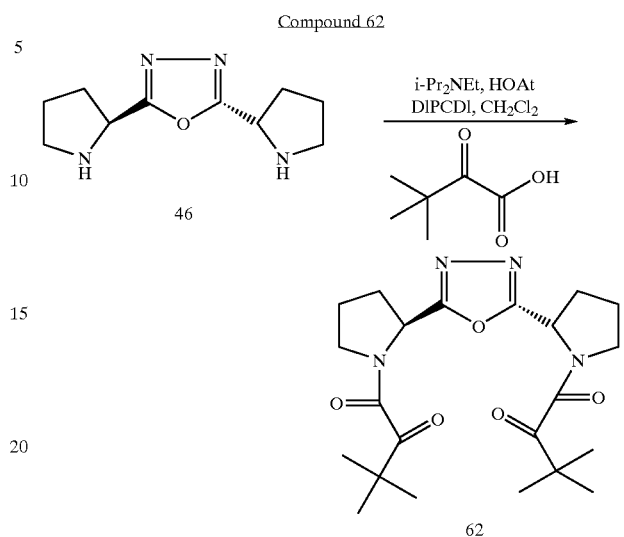

Utilizing the procedure of Method H, but with dimethylpyruvic acid in place of thiophene-2-glyoxylic acid, Compound 62 was obtained (0.030 g, 13.5% yield), identical in every respect with that obtained by Method D.

Compound 63

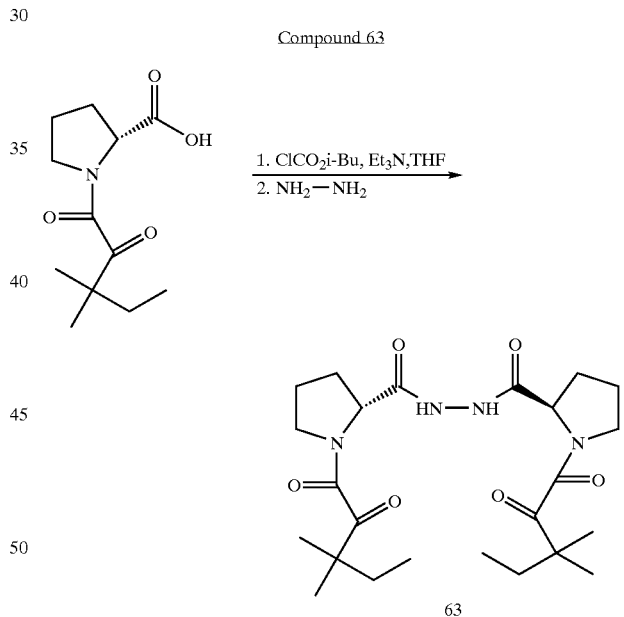

Utilizing the procedure of Method A, but with (2R)-1-(1,2-dioxo-3,3-dimethylpentyl)-2-piperidinecarboxylic acid as the substrate (prepared essentially as described for (2S)-1-(1,2-dioxo-3,3-dimethylpentyl)-2-pyrrolidinecarboxylic acid in WO 96/40633) in place of (2S)-1-(1,2-dioxo-3,3-dimethylpentyl)-2-pyrrolidinecarboxylic acid and isobutylchloroformate in place of ethyl chloroformate, Compound 63 was obtained as a colorless foamy solid (37% yield), mp 179–180° C. [α]=+101° (c=0.474, CHCl$_3$). CIMS 479 (MH$^+$), 501 (M+Na$^+$). $^1$H NMR (CDCl$_3$, mixture of rotamers) δ (for the major trans rotamer) 9.13 (br s, 2H), 4.61 (dd, 2H), 3.49 (m, 4H), 2.39–2.34 (m, 2H), 2.16–1.86 (m, 6H), 1.84–1.61 (m, 4H), 1.25 and 1.21 (each s, each 6H), 0.87 (t, 6H). IR (KBr) cm$^{-1}$: 3263, 2970, 2880, 1705, 1684, 1636, 1614, 1567, 1444. Anal Calcd. for $C_{24}H_{38}N_4O_5$: C, 60.23; H, 8.00; N, 11.71. Found: C, 59.96; H, 7.92; N, 11.55.

Compound 64

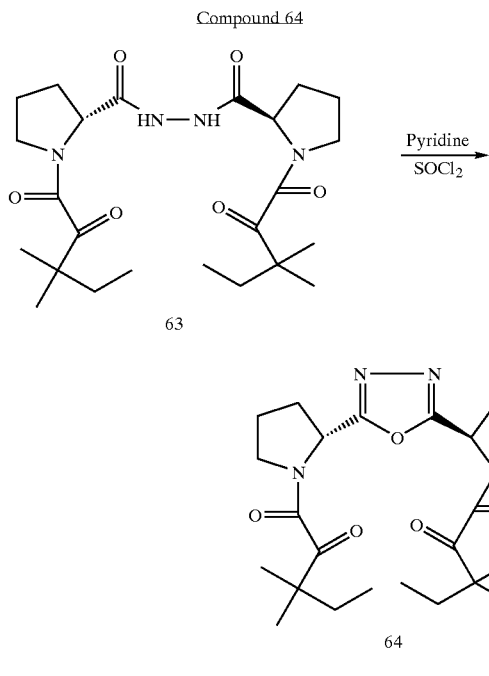

Utilizing the procedure of Method D with Compound 63 as the substrate, Compound 64 was obtained as an ivory solid (85% yield), mp 123–124° C. [α]=+72.2° (c=0.248, CHCl$_3$). CIMS 461 (MH$^+$), 483 (M+Na$^+$). $^1$H NMR (CDCl$_3$, mixture of rotamers) δ (for the major trans rotamer) 5.32 (dd, 2H), 3.68–3.53 (m, 4H), 2.41–2.02 (m, 8H), 1.83–1.58 (m, 4H), 1.23 and 1.20 (each s, each 3H), 0.86 (t, 6H). IR (KBr) cm$^{-1}$: 2973, 1705, 1639, 1574, 1463, 1432, 1383, 1096. Anal Calcd. for $C_{24}H_{36}N_4O_5$: C, 62.59; H, 7.88; N, 12.16. Found: C, 62.74; H, 7.81; N, 12.10.

Compound 65

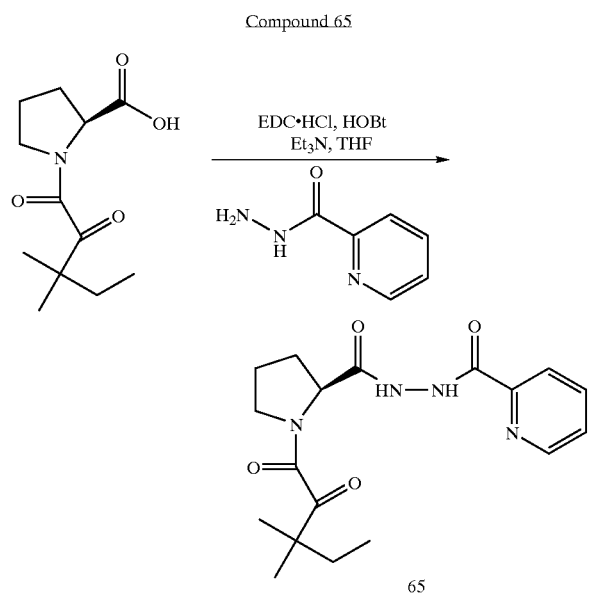

Utilizing the procedure of Method B, but with picolylhydrazide in place of hydrazine, Compound 65 was obtained as an ivory solid (71% yield), mp 182–185° C. [α]=−67.0° (c=0.26, CHCl$_3$). CIMS 361 (MH$^+$), 383 (M+Na$^+$). $^1$H NMR (CDCl$_3$, mixture of rotamers) δ (for the major trans rotamer) 10.00 (br s, 1H), 9.39 (br s, 1H), 8.57 (d, 1H), 8.15 (d, 1H), 7.86 (dt, 1H), 7.48–7.44 (m, 1H), 4.75–4.71 (m, 1H), 3.53–3.47 (m, 2H), 2.52–2.39 (m, 1H), 2.34–1.88 (m, 4H), 1.85–1.67 (m, 4H), 1.28 and 1.24 (each s, each 3H), 0.89 (t, 3H). IR (KBr) cm$^{-1}$: 3270, 2972, 2880, 1703, 1640. Anal. Calcd. for: $C_{18}H_{24}N_4O_4 \cdot 0.5H_2O$: C, 58.52; H, 6.82; N, 15.17. Found: C, 58.53; H, 6.44; N, 14.90.

Compound 66

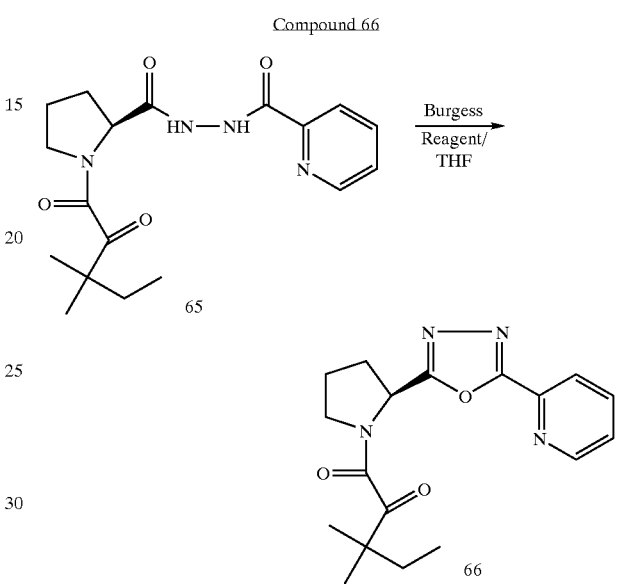

Utilizing the procedure of Method F with Compound 65 as the substrate, Compound 66 was obtained as a colorless crystalline solid (75% yield), mp 70–72° C. CIMS 343 (MH$^+$), 365 (M+Na$^+$). [α]=−36.8° C. (c=0.280, CHCl$_3$). $^1$H NMR (CDCl$_3$, mixture of rotamers) δ (for the major trans rotamer) 8.77 (d, 1H), 8.23 (d, 1H), 7.89 (d,t 1H), 5.45 (dd 1H), 3.76–3.62 (m, 2H), 2.44–2.05 (m, 4H), 1.86–1.63 (m, 2H), 1.27 and 1.23 (each s, each 3H), 0.87 (t, 3H). IR (KBr) cm$^{-1}$: 2973, 1701, 1636, 1588, 1562, 1552, 1463, 1441. Anal. Calcd. for $C_{18}H_{22}N_4O_3 \cdot 0.25H_2O$: C, 62.32; H, 6.54; N, 16.15. Found: C, 62.24; H, 6.38; N, 16.36.

IV. Biological Assays and Activity

Examples 1 and 4 in vitro activity results are shown in Table 2. Examples 2 and 3 detail the methods used for preparation of the cell cultures used in Example 4. Example 5 in vitro activity results are compiled in Table 3. Example 6 in vivo activity results are shown in FIG. 1.

A. In vitro Biological Activity

Example 1

Dorsal Root Ganglion (DRG) Culture

DRG are dissected from newborn or 1-day-old CD rats and placed into PBS on ice. After rinsing twice with sterile plating medium, DRG are transferred to empty wells of a 6-well plate coated with polyomithine/laminin (Becton Dickinson Labware) using #7 curved forceps. Three ml/well of plating medium are then added very gently, so as not to disturb the DRG. Plating medium is Leibovitz's L-15 medium (Gibco), plus 0.6% glucose, 33 mM KCl, 10% FCS, 10 mM Hepes and penicillin/streptomycin/glutamine. After overnight incubation at about 37° C. in 5% $CO_2$, this medium is replaced with 3 mL/well of assay medium [Leibovitz's L-15 medium plus 0.6% glucose, 1% FCS, 1%

N-2 supplement (Gibco), 10 μM ara-C, 10 mM Hepes, and penicillin/streptomycin/glutamine] containing either vehicle (DMSO, 1/200,000), positive control (2–4 ng/mL NGF) or test compound (50–250 nM). All media are prepared fresh daily. DRG are microscopically examined for neurite outgrowth on days 1–5. Under optimal conditions, vehicle treatment does not induce neurite outgrowth from DRG. An experiment is considered positive (+) if the instant compound induced neurites of ≧1 diameter of the DRG.

B. Cell Culture Assays

Example 2
Primary Rat Hippocampal Cells

Hippocampal cells are dissected from the brains of embryonic day 18 rat pups and dissociated with trypsin (1 mg/mL) and trituration. Cells are seeded at 30,000 cells/well in 96-well plates filled with 100 μL MEM and 10% FBS. At 7 days in culture, cells are fixed with 4% paraformaldehyde and immuno-fluorescence is performed.

Example 3
Human M17 Neuroblastoma Cells

M17 human neuroblastoma cells are cultured in 1:1 ratio of EMEM and Ham's F12 with 1×NEM and 10% FBS. The culture media contains 1×PSN antibiotic and is exchanged every other day, and the cells are passed in log phase near confluence.

TABLE 2

In Vitro Neurotrophic Activity

| Cmpd | DRG | Rat Hippocampal Cell Response | M17 Cell Response |
|---|---|---|---|
| 1 | – | NA | 103 |
| 3 | – | NA | NA |
| 4 | + | 111, 123 | 134, 111 |
| 8 | NT | NA | NA |
| 9 | NT | NA | NA |
| 10 | NT | NA | NA |
| 11 | + | NA | NA |
| 13 | – | NA | 102 |
| 14 | NT | 116 | 112, 108 |
| 15 | NT | NA | NA |
| 19 | NT | 109 | 110 |
| 24 | +, +, +, +, – | 119, 104, 108 | 123 |
| 25 | NT | 108 | 111 |
| 26 | NT | 133 | NA |
| 27 | NT | NA | NA |
| 28 | NT | NA | NT |
| 29 | NT | NA | NA |
| 30 | +, +, +, +, + | 161, 118, 130 | 112, 103 |
| 31 | +, +, +, +, +, +, – | 124 | 111 |
| 32 | NT | NA | 103 |
| 33 | NT | 112 | 104 |
| 34 | NT | 113 | 106 |
| 35 | NT | 126 | 106 |
| 36 | NT | NA | 110 |
| 37 | NT | 130 | 111 |
| 38 | NT | 129 | 105 |
| 39 | NT | NA | 112 |
| 43 | NT | 120 | 108 |
| 44 | NT | NA | 118 |
| 45 | NT | NA | NA |
| 46 | NT | NA | NA |
| 47 | NT | NA | NT |
| 48 | NT | 113 | NT |
| 49 | NT | NA | NT |
| 50 | NT | 110 | NT |
| 51 | NT | 107 | NT |
| 52 | NT | 110 | NT |
| 53 | NT | NA | NT |
| 54 | NT | 113 | NT |
| 55 | NT | 116 | NT |
| 56 | NT | 118, 116 | NT |
| 57 | NT | NA | NT |
| 58 | NT | 142 | NT |
| 59 | NT | 116 | NT |
| 60 | NT | 114 | NT |
| 62 | NT | 120 | NT |
| 63 | NT | 110 | NT |
| 64 | NT | 122 | NT |

+ = Positive results for each experiment
– = Negative results for each experiment
NA = Not active
NT = Not tested

Example 4
Neurite Outgrowth Assay

Cultures are incubated with normal horse serum (1:50; Vector Labs) for about 20 min, rinsed and then incubated with primary antibody, microtubule associated-protein 2 (anti-mouse MAP-2; 1:1000; Chemicon) for about 2 h at about RT. Following primary antibody, cultures are rinsed and incubated with fluorescein anti-mouse IgG (rat absorbed; 1:50; Vector Labs) for about 1 h. After fluorescein incubation, the cultures are rinsed and read in PBS on a fluorescent plate reader (excitation: 485 nm; emission: 530 nm). A compound is regarded as active if the neurite outgrowth response is greater than the mean DMSO-treated control response on the same plate. The response to test compound is reported as percent of DMSO-treated control. The signal-to-noise separation is consistent: the fluorescence from DMSO control wells is at least two-fold greater than blank wells.

Example 5
Nicotinic Acetylcholine Receptor Binding Assay

Binding of $^3$H-cytisine to neuronal nicotinic acetylcholine receptors is accomplished using crude synaptic membrane preparations from rat cerebral cortex, striatum and hippocampus. Either fresh or frozen membranes are homogenized in 50 volumes of 10 mM HEPES (N-2-hydroxyethylpiperazine-N'-2-ethanesulfonic acid, pH 7.4) and centrifuged at 42,000 g. The $P_2$ fraction is resuspended in 40 volumes of 10 mM HEPES and centrifuged at 42,000 g. This step is repeated and the $P_2$ fraction was resuspended in 25 volumes (e.g., 1 g of tissue into 25 mL) of a medium comprised of $Na^+$-HEPES buffer (10 mM, pH 7.4), 5 mM $MgCl_2$, 0.01% powdered bovine serum albumin (BSA) and 100 mM NaCl. To initiate the binding reaction, a compound of the instant invention (100 μL), Na-HEPES buffered incubation medium (400 μL), $^3$H-cytisine (250 μL) and the suspension of biological membranes (250 μL) is pipetted into a test tube, the contents mixed and then incubated at about 23° C. for about 40 min. The binding reaction is terminated by filtration using a Brandel Cell Harvester; the amount of bound $^3$H-cytisine for each sample is quantitated using a Wallac LKB 1205 Betaplate liquid scintillation counter. All compounds are screened at 10 μM in quadruplicate. Nonspecific binding is determined using 10 μM (+)-epibatidine to block all binding of $^3$H-cytisine to the α-4,β-2 nicotinic acetycholine receptor (α4β2nAChR). The activity of each test compound is calculated as follows: after correcting for nonspecific binding, the percent inhibition of specific binding (total binding minus nonspecific) is calculated. Each active compound is further tested at five concentrations to generate a concentration-inhibition curve. The $IC_{50}$ values are calculated by performing a nonlinear regression analysis of the data using a standard regression program.

TABLE 3

Binding Affinity ($IC_{50}$ nM) of Test Compounds to Nicotinic Acetylcholine Receptor

| Cmpd | $IC_{50}$ (nM) |
|---|---|
| 6 | 801 |
| 17 | 63.8 |

This invention provides methods of using Compounds 6 and 17 and pharmaceutical compositions comprising same to treat Parkinson's and Alzheimer's disease, anxiolysis, attention deficit hyperactivity disorder, "ADHD," Turret's Syndrome, smoking addiction and pain.

C. In vivo Biological Activity

Example 6

Rat Facial Nerve Compression Model

Long-Evans rats are anesthetized under ketamine (60 mg/kg)/xylazine (6mg/kg). The facial nerve is exposed and mechanically compressed with forceps near the stylomastoid foramen unilaterally with the opposite, non-lesioned side serving as an internal control. Nerve compression causes paralysis of the whisker muscle, hence the reduced whisker movement on the lesioned side which is observed immediately after recovery from anesthesia. Rats received test compound p.o. at about 20 mg/kg twice a day for 15 days after the surgery. Control rats received vehicle only. Three to eight rats are tested in each group. Restoration of whisker movement after the treatment with compounds of the present invention is recorded at different post-operative time points daily, up to two weeks, and is shown in FIG. 1.

What is claimed is:

1. A compound having the structure

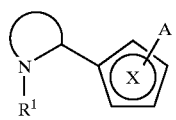

or a pharmaceutically acceptable salt thereof, wherein
(a) $R^1$ is selected from the group consisting of H, $COCOR^2$, $COOR^3$ and $SO_2R^3$,
 (i) $R^2$ being selected from the group consisting of $C_{1-6}$ straight or branched alkyl, $C_{1-6}$ straight or branched alkenyl, $C_{5-7}$ cycloalkyl, 2-thienyl, 3-thienyl or phenyl, the phenyl having one to three substituents independently selected from the group consisting of H, lower alkyl, lower alkoxyl, hydroxyl and halogen, and
 (ii) $R^3$ being phenylalkyl, wherein the phenyl has one to three substituents independently selected from the group consisting of H, lower alkyl, lower alkoxyl, hydroxyl and halogen;

(b)

is either a saturated five-membered nitrogen containing heterocyclic ring, said ring containing one nitrogen atom, or a benzo-fused saturated six-membered nitrogen containing heterocyclic ring;

(c)

is an oxazole, an oxadiazole or a thiazole; and (d) A is attached to a carbon of the five-membered heteroaromatic ring and is selected from the group consisting of $COO(CH_2)_m Ar$,

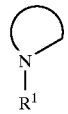

(such $R^1$ being the same as or different than the $R^1$ described in part (a)), $CONR^4(CH_2)_m Ar$, and $(CH_2)_m O(CH_2)_n Ar$ (wherein $R^1$ cannot be $COCOR^2$ or $SO_2R^3$),
 (i) $R^4$ being H or $C_{1-4}$ alkyl;
 (ii) Ar being selected from the group consisting of 2-pyridyl, 3-pyridyl, and 4 pyridyl;
 (iii) m being 1–4; and
 (iv) n being 0–4.

2. The compound of claim 1 having the structure

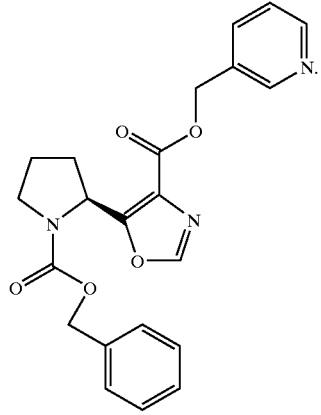

3. The compound of claim 1 having the structure

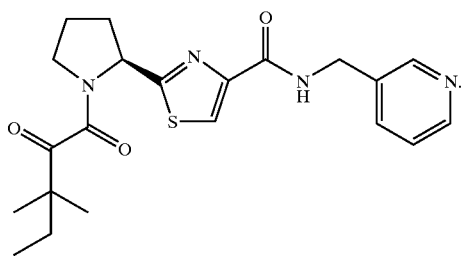

4. The compound of claim 1 having the structure

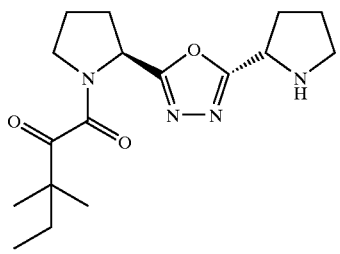

5. The compound of claim 1 having the structure

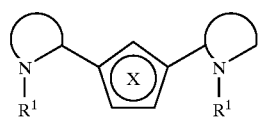

wherein each $R^1$ is either the same as, or different than, the other.

6. The compound of claim 5 having the structure

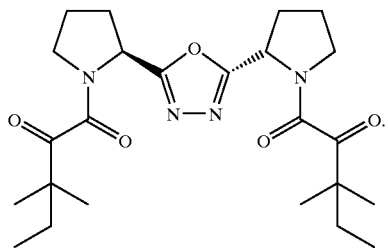

7. The compound of claim 5 having the structure

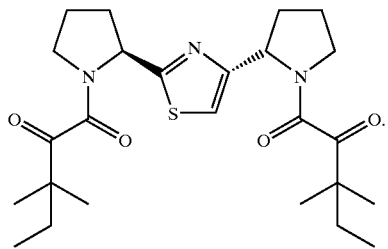

8. The compound of claim 5 having the structure

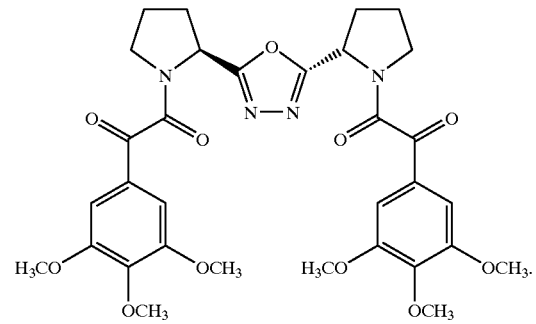

9. The compound of claim 5 having the structure

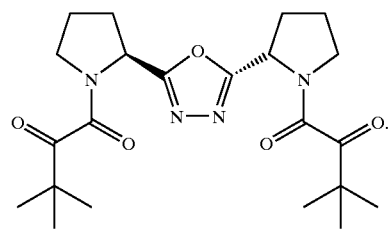

10. The compound of claim 5 having the structure

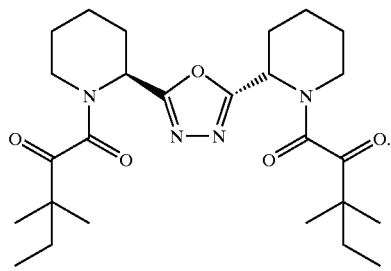

11. The compound of claim 5 having the structure

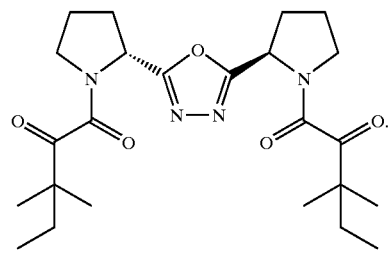

12. A compound having the structure

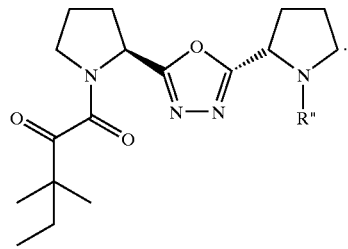

13. A method of treating in a subject, Parkinson's disease, Alzheimer's disease, stroke, multiple sclerosis, amyotrophic lateral sclerosis, diabetic neuropathy or Bell's palsy, comprising administering to the subject a prophylactically effective amount of the compound of claim 1.

* * * * *